US010107813B2

(12) United States Patent
Halford

(10) Patent No.: US 10,107,813 B2
(45) Date of Patent: Oct. 23, 2018

(54) RAPID AND SENSITIVE SEROLOGICAL ASSAY TO DETERMINE IF PATIENTS ARE INFECTED WITH HERPES SIMPLEX VIRUS TYPE 1 HSV-1 AND/OR TYPE 2 HSV-2

(71) Applicant: Board of Trustees, Southern Illinois University, Carbondale, IL (US)

(72) Inventor: William Halford, Springfield, IL (US)

(73) Assignee: Board of Trustees, Southern Illinois University, Carbondale, IL (US)

( * ) Notice: Subject to any disclaimer, the term of this patent is extended or adjusted under 35 U.S.C. 154(b) by 0 days.

(21) Appl. No.: 15/104,562

(22) PCT Filed: Dec. 17, 2014

(86) PCT No.: PCT/US2014/070915
§ 371 (c)(1),
(2) Date: Jun. 15, 2016

(87) PCT Pub. No.: WO2015/095366
PCT Pub. Date: Jun. 25, 2015

(65) Prior Publication Data
US 2016/0313331 A1 Oct. 27, 2016

Related U.S. Application Data

(60) Provisional application No. 61/917,584, filed on Dec. 18, 2013.

(51) Int. Cl.
*G01N 33/569* (2006.01)
(52) U.S. Cl.
CPC . *G01N 33/56994* (2013.01); *G01N 2333/035* (2013.01); *G01N 2469/20* (2013.01)
(58) Field of Classification Search
None
See application file for complete search history.

(56) References Cited

U.S. PATENT DOCUMENTS 5,965,354 A 10/1999 Burke et al.
2011/0059553 A1 3/2011 Su et al.

FOREIGN PATENT DOCUMENTS

WO 2005098051 A2 10/2005

OTHER PUBLICATIONS

Hamper et al. Enzyme-Linked Immunosorbent Assay for Determination of Antibodies Against Herpes Simplex Virus Types 1 and 2 in Human Sera. Journal of Clinical Microbiology, Apr. 1985, 21(4): 496-500.*
Caruso et al. Flow Cytometrlc Indirect Immunofluorescence Assay With High Sensitivity and Specificity for the Detection of Antibodies to HSV-1 and HSV-2. Eur. J. Epidemiol. 1993. 9(5): 547-552.*
Jordan et al. Detection of Herpes Simplex Virus (HSV) Type-1 IgG and IgM Antibodies by Enzyme-Linked Immunosorbent Assay (ELISA). Am J Clin Pathol. Oct. 1981;76(4):467-71.*
Allen, et al., "Role of Coexpression of IL-2 and Herpes Simplex Virus Proteins in Recombinant Vaccinia Virus Vectors on Levels of Induced Immunity," Viral Immunology, Mar. 13, 2009, vol. 3, No. 3, pp. 207-215.
Ashley et al., "Comparison of Western Blot (Immunoblot) and Glycoprotein GSpecific Immunodot Enzyme Assay for Detecting Antibodies to Herpes Simplex Virus Types 1 and 2 in Human Sera," Journal of Clinical Microbiology, Apr. 1988, vol. 26, No. 4, pp. 662-667.
Belshe et al., "Efficacy Results of a Trial of a Herpes Simplex Vaccine," The New England Journal of Medicine, Jan. 5, 2012, vol. 366, No. 1, pp. 34-43.
Bernstein, "Glycoprotein D Adjuvant Herpes Simplex Virus Vaccine," Expert Review Vaccines, 2005, vol. 4, pp. 615-627.
Bernstein et al., "The Adjuvant CLDC Increases Protection of a Herpes Simplex Type 2 Glycoprotein D Vaccine in Guinea Pigs," Vaccine, May 7, 2010, vol. 28, pp. 3748-3753.
Bernstein et al., "Effects of Herpes Simplex Virus Type 2 Glycoprotein Vaccines and CLDC Adjuvant on Genital Herpes Infection in the Guinea Pig," Vaccine, Mar. 3, 2011, vol. 29, Issue 11, pp. 2071-2078.
Bourne et al., "Herpes Simplex Virus (HSV) Type 2 Glycoprotein D Subunit Vaccines and Protection against Genital HSV-1 or HSV-2 Disease in Guinea Pigs," Journal of Infectious Disease, Feb. 15, 2003, vol. 187, Issue 4, pp. 542-549.
Bourne et al. "Impact of Immunization with Glycoprotein D2/AS04 on Herpes Simplex Virus Type 2 Shedding into the Genital Tract in Guinea Pigs That Become Infected," Journal of Infectious Disease, 2005:192, Dec. 15, pp. 2117-2123.
Brans, Richard, and Feng Yao. "Immunization with a dominant-negative recombinant Herpes Simplex Virus (HSV) type 1 protects against HSV-2 genital disease in guinea pigs." BMC Microbiology 10.1 (2010): 163.
MMWR Morbidity and Mortality Weekly Report, Seroprevalence of Herpes Simplex Virus Type 2 Among Persons Aged 14-49 Years—United States, 2005-2008, Apr. 23, 2010, vol. 29, No. 15, pp. 456-459.

(Continued)

*Primary Examiner* — Nianxiang Zou
(74) *Attorney, Agent, or Firm* — Husch Blackwell LLP

(57) ABSTRACT

An assay for infection with one or more herpes simplex viruses that comprises a) dividing an antibody-containing serum sample into at least three serum subsamples, and b) separately incubating each with a physical matrix of cell antigens from i) uninfected cells, (ii) HSV-1-infected cells, or (iii) HSV-2-infected cells to form at least three serum subsample admixtures so that antibodies present in each admixture can immunoreact to form matrix-bound antibodies and at least three preadsorbed serum subsample portions. Each preadsorbed serum subsample portion is incubated with a mixture of matrix-bound antigens from cells uninfected by HSV-1 or HSV-2, infected by each of HSV-1 and by HSV-2 to permit antibodies to immunoreact with antigens present to form three matrix-bound immunoreactants. The amount of each immunoreaction is determined, and reaction amounts are prognostic for whether the subject whose serum was tested is infected by one, both, or neither of HSV-1 and HSV-2.

20 Claims, 49 Drawing Sheets

(56) References Cited

OTHER PUBLICATIONS

Chentoufi et al., "A Novel HLA (HLA-Ap0201) Transgenic Rabbit Model for Preclinical Evaluation of Human CD8+ T Cell Epitope-Based Vaccines against Ocular Herpes," The Journal of Immunology, Mar. 1, 2010, 184(5), pp. 2561-2571.
Chu et al., "Antibody-mediated Protection Against Genital Herpes Simplex Virus Type 2 Disease in Mice by Fc Gamma Receptor-dependent and -independent Mechanisms," Journal of Reproductive Immunology, Jun. 2008, vol. 78, Issue 1, pp. 58-67.
Corey et al., "Recombinant Glycoprotein Vaccine for the Prevention of Genital HSV-2 Infection," JAMA, Jul. 28, 1999, vol. 281, No. 4, pp. 331-340.
Corey et al., "Once-Daily Valacyclovir to Reduce the Risk of Transmission of Genital Herpes," The New England Journal of Medicine, Jan. 1, 2004, vol. 350, No. 1, pp. 11-20.
DeJesus et al., "Valacyclovir for the Suppression of Recurrent Genital Herpes in Human Immunodeficiency Virus-Infected Subjects," The Journal of Infectious Diseases, Oct. 1, 2003, 188(7), pp. 1009-1016.
Divito et al., "A Triple Entente: Virus, Neurons, and CD8+ T Cells Maintain HSV-1 Latency," Immunologic Research, Sep. 2006, vol. 36, Issue 1, pp. 119-126.
Dudek et al., "Replication-defective Viruses as Vaccines and Vaccine Vectors," Virology, Jan. 5, 2006, vol. 344, Issue 1, pp. 230-239.
Eing et al., "Evaluation of Confirmatory Strategies for Detection of Type-Specific Antibodies against Herpes Simplex Virus Type 2," Journal of Clinical Microbiology, Feb. 2002, vol. 40, No. 2, pp. 407-413.
Eo et al., "Prime-Boost Immunization with DNA Vaccine: Mucosal Route of Administration Changes the Rules," The Journal of Immunology, May 1, 2001, 166.9, pp. 5473-5479.
Gilman et al., "Antibody Responses in Humans to Individual Proteins of Herpes Simplex Viruses," Infection and Immunity, Dec. 1981, vol. 34, No. 3, pp. 880-887.
Golden et al., "Herpes Simplex Virus Type 2 (HSV-2) Western Blot Confirmatory Testing Among Men Testing Positive for HSV-2 Using the Focus Enzyme-Linked Immunosorbent Assay in a Sexually Transmitted Disease Clinic," Sexually Transmitted Diseases, Dec. 2005, vol. 32, No. 12, pp. 771-777.
Gupta et al., "Genital Herpes," Lancet, Dec. 22/29, 2007, vol. 370, pp. 2127-2137.
Halford et al., "Mathematical Analysis Demonstrates that Interferons-b and -g Interact in a Multiplicative Manner to Disrupt Herpes Simplex Virus Replication," Journal of Theoretical Biology, Jun. 7, 2005, vol. 234, Issue 3, pp. 439-454.
Halford et al., "Re-Evaluating the Role of Natural Killer Cells in Innate Resistance to Herpes Simplex Virus Type 1," Virology Journal, Jul. 17, 2005, 2:56, 15 pgs.
Halford et al., "Herpes Simplex Virus 2 ICP02 Mutant Viruses Are Avirulent and Immunogenic: Implications for a Genital Herpes Vaccine," PloS ONE, Aug. 17, 2010, vol. 5, Issue 8, 17 pgs.
Halford et al., "A Live-Attenuated HSV-2 ICP02 Virus Elicits 10 to 100 Times Greater Protection against Genital Herpes than a Glycoprotein D Subunit Vaccine," PLOS ONE, Mar. 2011, vol. 6, Issue 3, 18 pgs.
Halford et al., "Pan-HSV-2 IgG Antibody in Vaccinated Mice and Guinea Pigs Correlates with Protection against Herpes Simplex Virus 2," PLOS ONE, Jun. 2013, vol. 8, Issue 6, 15 pgs.
Handsfield et al., "Suppressive Therapy With Valacyclovir in Early Genital Herpes: A Pilot Study of Clinical Efficacy and Herpes-Related Quality of Life," Sexually Transmitted Diseases, Jun. 2007, vol. 34, Issue 6, pp. 339-343.
Hosken et al., "Diversity of the CD8 T-Cell Response to Herpes Simplex Virus Type 2 Proteins among Persons with Genital Herpes," Journal of Virology, Jun. 2006, vol. 80, No. 11, pp. 5509-5515.
Johnston et al., "HSV-2: in Pursuit of a Vaccine," The Journal of Clinical Investigation, Dec. 2011, vol. 121, No. 12, pp. 4600-4609.
Karem et al., "Protective immunity against herpes simplex virus (HSV) type 1 following oral administration of recombinant *Salmonella typhimurium* vaccine strains expressing HSV antigens," Journal of General Virology, 1997, 18, pp. 427-434.
Khanna et al., "Herpes Simplex Virus-Specific Memory CD8 T Cells Are Selectively Activated and Retained in Latently Infected Sensory Ganglia," Immunity, May 2003, vol. 18, pp. 593-603.
Khodai et al., "Single and Combination Herpes Simplex Virus Type 2 Glycoprotein Vaccines Adjuvanted with CpG Oligodeoxynucleotides or Monophosphoryl Lipid A Exhibit Differential Immunity That Is Not Correlated to Protection in Animal Models," Clinical and Vaccine Immunology, Oct. 2011, vol. 18, No. 10, pp. 1702-1709.
Knickelbein et al., "Noncytotoxic Lytic Granule-Mediated CD8+ T Cell Inhibition of HSV-1 Reactivation from Neuronal Latency," Science, Oct. 10, 2008, vol. 322, pp. 268-271.
Koelle et al., "Herpes Simplex: Insights on Pathogenesis and Possible Vaccines," Annual Review of Medicine, Feb. 2008, vol. 59, pp. 381-395.
Kuklin et al., "Induction of Mucosal Immunity against Herpes Simplex Virus by Plasmid DNA Immunization," Journal of Virology, Apr. 1997, vol. 71, No. 4, pp. 3138-3145.
Laing et al., "Diversity in CD8+ T Cell Function and Epitope Breadth Among Persons with Genital Herpes," Journal of Clinical Immunology, 2010, vol. 30, No. 5, pp. 703-722.
Laing et al., "Immunology in the Clinic Review Series; Focus on Host Responses: T cell responses to herpes Simplex," Clinical and Experimental Immunology, Dec. 1, 2011, vol. 167, Issue 1, pp. 47-58.
Lingappa et al., "Clinical and Therapeutic Issues for Herpes Simplex Virus-2 and HIV Co-Infection," Drugs, Feb. 2007, vol. 67, Issue 2, pp. 155-174.
Liu et al., "CD8 1 T Cells Can Block Herpes Simplex Virus Type 1(HSV-1) Reactivation from Latency in Sensory Neurons," J. Exp. Med., May 1, 2000, vol. 191, No. 9, pp. 1459-1466.
Mackay et al., "Long-lived epithelial immunity by tissue-resident memory T (TRM) cells in the absence of persisting oval antigen presentation," PNAS, May 1, 2012, vol. 109, No. 18, pp. 7037-7042.
Manickan et al., "Vaccination with Recombinant Vaccinia Viruses Expressing ICP27 Induces Protective Immunity against Herpes Simplex Virus through CD41 Th11 T Cells," Journal of Virology, Aug. 1995, pp. 4711-4716.
McClements et al., "Immunization with DNA vaccines encoding glycoprotein D or glycoprotein B, alone or in combination, induces protective immunity in animal models of herpes simplex virus-2 disease," Proc. Natl. Acad. Sci., Oct. 1996, vol. 93, pp. 11414-11420.
Meignier et al., "In Vivo behavior of Genetically Engineered Herpes Simplex Viruses R7017 and R7020: Construction and Evaluation in Rodents," The Journal of Infectious Disease, Sep. 1988, vol. 158, No. 3, pp. 602-614.
Mertz et al., "Double-Blind, Placebo-Controlled Trial of a Herpes Simplex Virus Type 2 Glycoprotein Vaccine in Persons at High Risk fore Genital Herpes Infection," JID, Apr. 1990, 161, pp. 653-660.
Morrison et al., "Vaccine-Induced Serum Immunoglobin Contributes to Protection from Herpes Simplex Virus Type 2 Genital Infection in the Presence of Immune T Cells," Journal of Virology, Feb. 2001, vol. 75, No. 3, pp. 1195-1204.
Morrison et al., "Vaccines Against Genital Herpes Progress and Limitations," Drugs, Jun. 2002, vol. 62, Issue 8, pp. 1119-1129.
Nagafuchi et al., "Mechanism of Acquired Resistance to Herpes Simplex Virus Infection as Studied in Nude Mice," J. Gen. Virol, 1979, 44, pp. 715-723.
Natuk et al., "Recombinant Vesicular Stomatitis Virus Vectors Expressing Herpes Simplex Virus Type 2 gD Elicit Robust CD4 Th1 Immune Responses and Are Protective in Mouse and Guinea Pig Models of Vaginal Challenge," Journal of Virology, May 2006, vol. 80, No. 9, pp. 4447-4457.
Ng'ayo et al., "Performance of HSV-2 Type Specific Serological Tests in Men in Kenya," J. Virol. Methods, Feb. 2010, 163(2): 276, 14 pgs.

(56) References Cited

OTHER PUBLICATIONS

Nicola et aL., "Structure-Function Analysis of Soluble Forms of Herpes Simplex Virus Glycoprotein D," Journal of Virology, Jun. 1996, vol. 70, No. 6, pp. 3815-3822.

Norrild et al., "Immunological Reactivity of Herpes Simplex Virus 1 and 2 Polypeptides Electrophoretically Separated and Transferred to Diazobenzyloxymethyl Paper," Infection of Immunity, Feb. 1981, vol. 31, No. 2, pp. 660-667.

Oakes et al., "Role for Cell-Mediated Immunity in the Resistance of Mice to Subcutaneous Herpes Simplex Virus Infection," Infection of Immunity, Jul. 1975, vol. 12, No. 1, pp. 166-172.

Orr et al, "Cutting Edge: Recombinant Listeria monocytogenes Expressing a Single Immune-Dominant Peptide Confers Protective Immunity to Herpes Simplex Virus-1 Infection," The Journal of Immunology, Apr. 15, 2007, 178(8), pp. 4731-4735.

Bailey et al., "Herpes simplex virus type 2: epidemiology and management options in developing countries," Sexually Transmitted Infections, Feb. 1, 2007, vol. 83, Issue 1, pp. 16-22.

Posavad et al., "Detailed Characterization of T Cell Responses to Herpes Simplex Virus-2 in Immune Seronegative Persons," The Journal of Immunology, Mar. 15, 2010, 184, pp. 3250-3259.

Preacher et al., "Calculation for Fisher's Exact Test: An interactive calculation tool for Fisher's exact probability test for 2×2 tables [Computer software]," May 2001, http://quantpsy.org. 2 pgs.

Pyles et al, :Use of Immunostimulatory Sequence-Containing Oligonucleotides as Topical Therapy for Genital Herpes Simplex Virus Type 2 Infection, Journal of Virology, Nov. 2002, vol. 76, No. 22, pp. 11387-11396.

Rana et al, "Sexual behaviour and condom use among individuals with a history of symptomatic genital herpes," Sex Transm Infect, 2006, vol. 82, Issue 1, pp. 69-74.

Rattray et al, "Recurrent genital herpes among women: symptomatic v. asymptomatic viral shedding," British Journal of Venereal Diseases, Aug. 1, 1978, vol. 54, Issue 4, pp. 262-265.

Roizman et al., "Identification and Preliminary Mapping with Monolonal Antibodies of a Herpes Simplex Virus 2 Glycoprotein Lacking a Known Type 1 Counterpart," Virology, Feb. 1984, vol. 133, Issue 1, pp. 242-247.

Rouse et al., "A Tale of Two -Herpesviruses: Lessons for Vaccinologists," Clinical Infectious Diseases, Mar. 15, 2006; 42(6), pp. 810-817.

Samaniego et al., "Persistence and Expression of the Herpes Simplex Virus Genome in the Absence of Immediate-Early Proteins," Journal of Virology, vol. 72, No. 4, Apr. 1988, pp. 3307-3320.

Sanchez-Martinez et al., "Evaluation of a Test Based Baculovirus-Expressed Glycoprotein G for Detection of Herpes Simplex Virus Type-Specific Antibodies," JID, Dec. 1, 1991, 164(6), pp. 1196-1199.

Shin et al, A vaccine strategy that protects against genital herpes by establishing local memory T cells, Nature, Nov. 15, 2012, vol. 491, pp. 463-468.

Shlapobersky, et al., "Vaxfectin-adjuvanted plasmid DNA vaccine improves protection and immunogenicity in a murine model of genital herpes infection," Journal of General Virology, Jun. 1, 2012, 93(6), pp. 1305-1315.

Simmons et al, "Anti-CD8 Impairs Clearance of Herpes Simplex Virus from the Nervous System: Implications for the Fate of Virally Infected Neuronsm," J. Exp. Med., May 1992, vol. 175, pp. 1337-1344.

Sperling et al., "The Effect of Daily Valacyclovir Suppression on Herpes Simplex Virus Type 2 Viral Shedding in HSV-2 Seropositive Subjects Without a History of Genital Herpes," Sexually Transmitted Diseases, Mar. 2008, vol. 35, No. 3, pp. 286-290.

St. Leger et al, "Defining the Herpes Simplex Virus-Specific CD8+ T Cell Repertoire in C57BL/6 Mice," The Journal of Immunology, Apr. 1, 2011, 186(7), pp. 3927-3933.

Staats et al., "Anti-Glycoprotein D Monoclonal Antibody Protects against Herpes Simplex Virus Type 1-Induced Diseases in Mice Functionally Depleted of Selected T-Cell Subsets or Asialo GM1+ Cells," Journal of Virology, Nov. 1991, vol. 65, No. 11, pp. 6008-6014.

Stanberry et al., "Glycoprotein-D—Adjuvant Vaccine to Prevent Genital Herpes," The New England Journal of Medicine, vol. 347, No. 21, pp. 1652-1661.

Straus et al., "Placebo-controlled trial of vaccination with recombinant glycoprotein D of herpes simplex virus type 2 for immunotherapy of genital herpes," The Lancet, Jun. 1, 994, vol. 343, Issue 8911, pp. 1460-1463.

Straus et al., "Immunotherapy of Recurrent Genital Herpes with Recombinant Herpes Simplex Virus Type 2 Glycoproteins D and B: Results of a Placebo-Controlled Vaccine Trial," The Journal of Infectious Diseases, Nov. 1997, vol. 176, Issue 5, pp. 1129-1134.

Theil et al., "Latent Herpesvirus Infection in Human Trigeminal Ganglia Causes Chronic Immune Response," American Journal of Pathology, Dec. 2003, vol. 163, No. 6, pp. 2179-2184.

Tirabassi et al., "A Mucosal Vaccination Approach for Herpes Simplex Virus Type-2," Vaccine, Jan. 29, 2011, vol. 29, Issue 5, pp. 1090-1098.

Tronstein et al., "Genital Shedding of Herpes Simplex Virus Among Symptomatic and Asymptomatic Persons With HSV-2 Infection," JAMA, Apr. 13, 2011, vol. 305, No. 14, pp. 1441-1449.

Vergidis et al., "Meta-analytical Studies on the Epidemiology, Prevention, and Treatment of Human Immunodeficiency Virus Infection," Infectious Disease Clinics of North America, 2009, vol. 23, Issue 2, pp. 295-308.

Wald et al, "Reactivation of Genital Herpes Simplex Virus Type 2 Infection in Asymptomatic Seropositive Persons," The New England Journal of Medicine, Mar. 23, 2000, vol. 342, No. 12, pp. 844-850.

Wald et al., "Effect of Condoms on Reducing the Transmission of Herpes Simplex Virus Type 2 From Men to Women," JAMA, Jun. 27, 2001, vol. 285, No. 24, pp. 3100-3106.

Warren, "Getting Tested for Herpes," FDA Consumer, Mar.-Apr. 2002, p. 40.

Warren et al. "Counseling the patient who has genital herpes or genital human papillomavirus infection." Infectious disease clinics of North America, Jun. 30, 2005, 19.2, pp. 459-476.

Warren et al, "Availability of Serologic and Virologic Testing for Herpes Simplex Virus in the Largest Sexually Transmitted Disease Clinics in the United States," Apr. 2011, vol. 38, Issue 4, pp. 267-269.

Weir et al., "Recombinant Vaccinia Virus Expressing the Herpes Simplex Virus Type 1 Glycoprotein C Protects Mice against Herpes Simplex Virus Challenge," Journal of General Virology, Oct. 1, 1989, vol. 70, Issue 10, pp. 2587-2594.

Whittington et al, "Use of a Glycoprotein G-Based Type-Specific Assay to Detect Antibodies to Herpes Simplex Virus Type 2 Among Persons Attending Sexually Transmitted Disease Clinics," Sexually Transmitted Diseases, Feb. 2001, vol. 28, Issue 2, pp. 99-104.

Xu et al, "Trends in Herpes Simplex Virus Type 1 and Type 2 Seroprevalence in the United States," JAMA, Aug. 23/30, 20016, 296(8), pp. 964-973.

Zhu et al, "Virus-specific CD8+ T cells accumulate near sensory nerve endings in genital skin during subclinical HSV-2 reactivation," Mar. 19, 2007, 204)3), pp. 595-603.

Bernstein et al., "Serologic Analysis of First-Episode Nonprimary Genital Herpes Simplex Virus Infection, Presence of Type 2 Antibody in Acute Serus Samples," The American Journal of Medicine, vol. 77, Dec. 1984, pp. 1055-1060.

Jani et al., "Multiplexed Immunoassays by Flow Cytometry for Diagnosis and Surveillance of Infectious Diseases in Resource-Poor Settings," The Lancet Infectious Diseases, vol. 2, Apr. 2002, pp. 243-250.

Sherlock et al., "Type Specificity of Complement-Fixing Antibody against Herpes Simplex Virus Type 2 AG-4 Early Antigen in Patients with Asymptomatic Infection," Journal of Clinical Microbiology, Dec. 1986, pp. 1093-1097.

EPO Communication regarding EP application No. 14 872 357.0, dated Jan. 18, 2018 (3pgs.).

EPO Communication regarding EP application No. 14 872 357.0, dated Apr. 26, 2017 (5pgs.).

Supplemental European Search Report regarding EP application No. 14 872 357.0, dated Apr. 18, 2017 (3pgs.).

(56) References Cited

OTHER PUBLICATIONS

International Search Report regarding PCT/US2014/070915, dated Apr. 10, 2015 (2 pgs.).
Written Opinion of the International Searching Authority regarding PCT/US2014/070915, dated Apr. 10, 2015 (4 pgs.).
International Preliminary Report on Patentability regarding PCT/US2014/070915, dated Jun. 21, 2016 (6 pgs.).

* cited by examiner

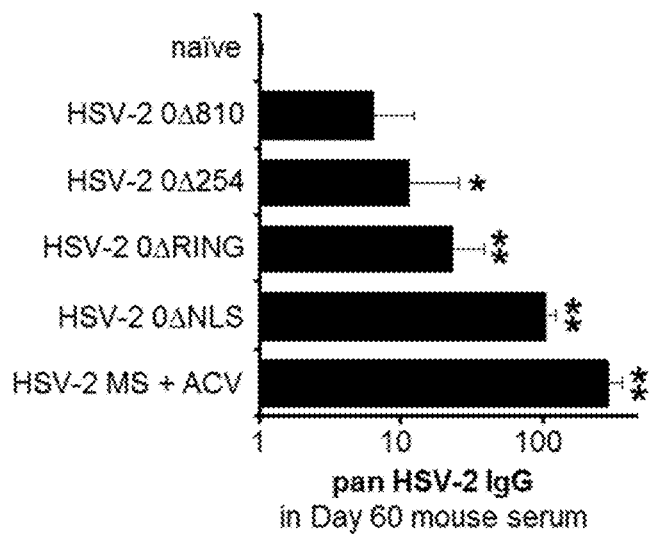
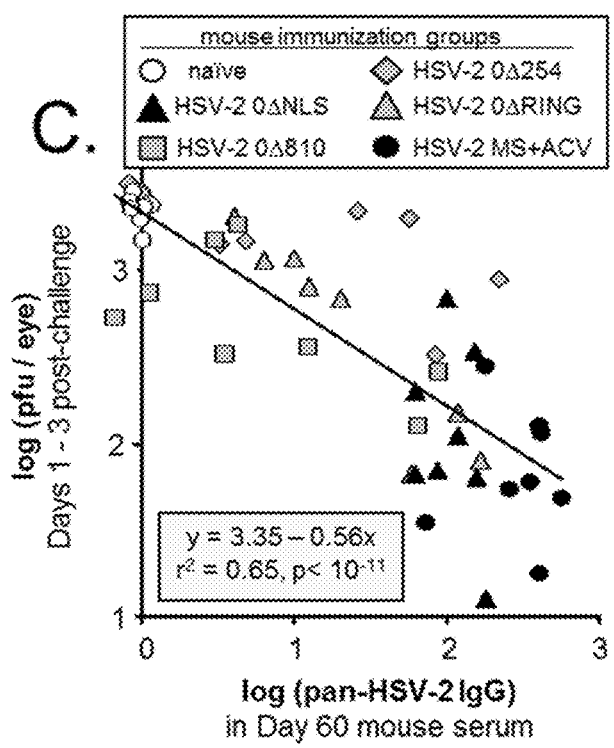
FIG. 2 Cont'd.

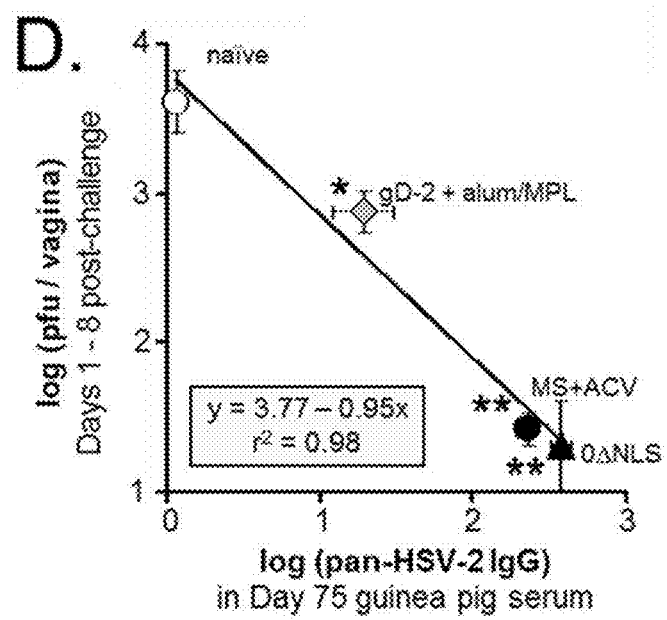
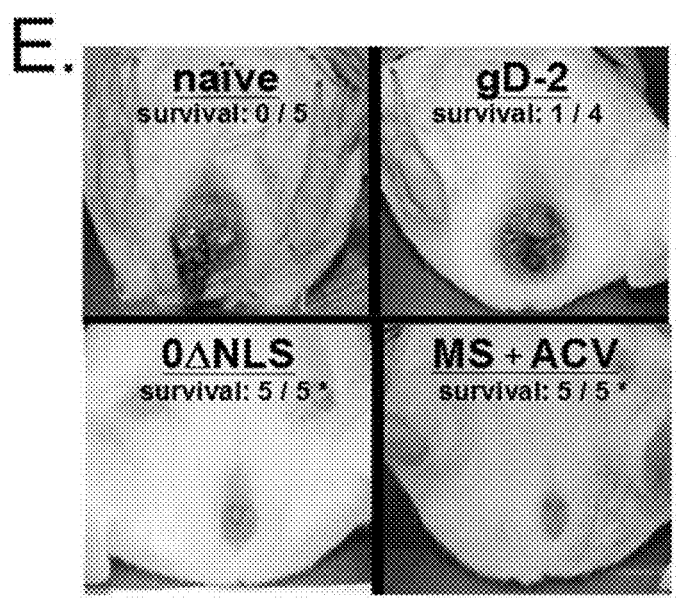
FIG. 4 Cont'd.

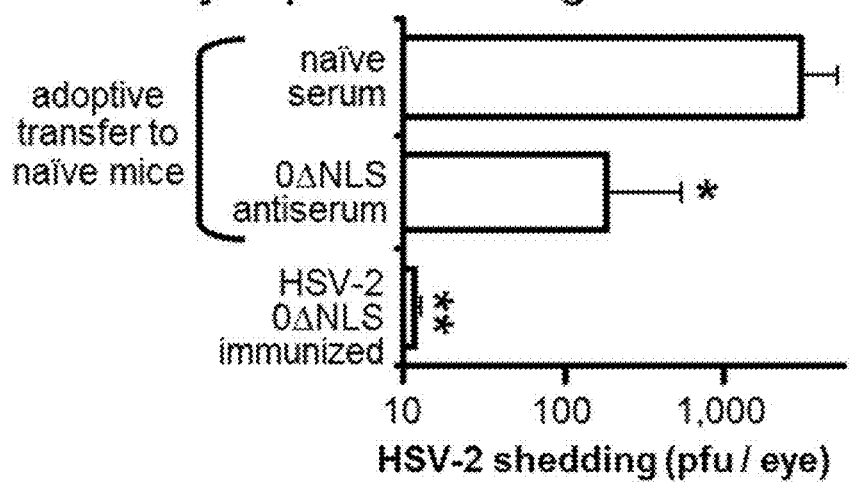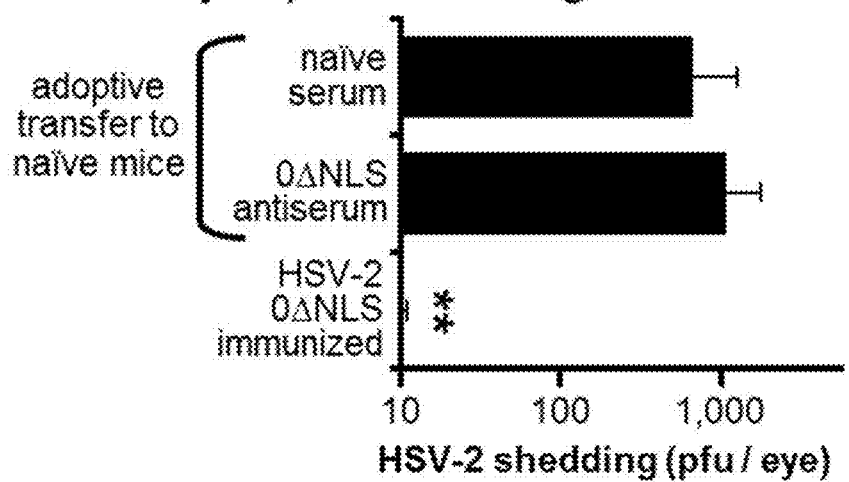
FIG. 5

| | Neutralization Assay | ELISA (total HSV-2 Ag) | Flow Cytometry Assay |
|---|---|---|---|
| Linear range [a] | 1:21 – 1:1,000 | 1:100 – 1:100,000 | 1:6,000 – 1:6,000,000 |
| Coefficient of variation [b] | 16 ± 8% | 13 ± 3% | 5 ± 1% |
| Goodness-of-fit [c] (linear regression) | $r^2 = 1.00$ ($p < 10^{-5}$) | $r^2 = 1.00$ ($p < 10^{-10}$) | $r^2 = 1.00$ ($p < 10^{-12}$) |

FIG. 6

| Immunogen [a] | Species [b] | log (pan-HSV-2 IgG) [c] | log decrease in vaginal HSV-2 shedding [d] | Survival frequency [e] |
|---|---|---|---|---|
| Medium (naïve) | mice | -0.1 ± 0.1 | 0.0 ± 0.1 | 0 / 10 |
| | guinea pigs | 0.1 ± 0.1 | 0.0 ± 0.2 | 0 / 5 |
| GFP + alum/MPL | mice | -0.1 ± 0.1 | -0.4 ± 0.3 | 0 / 10 |
| | guinea pigs | ND [f] | ND | ND |
| gD-2 + alum/MPL | mice | 1.0 ± 0.1 ** | 0.7 ± 0.1 * | 1 / 10 |
| | guinea pigs | 1.3 ± 0.2 ** | 0.7 ± 0.1 * | 1 / 4 |
| HSV-2 MS (ACV-restrained) | mice | 2.6 ± 0.1 ** | 1.9 ± 0.2 ** | 10 / 10 †† |
| | guinea pigs | 2.4 ± 0.1 ** | 2.2 ± 0.1 ** | 5 / 5 † |
| HSV-2 0ΔNLS | mice | 2.8 ± 0.1 ** | 2.2 ± 0.2 ** | 10 / 10 †† |
| | guinea pigs | 2.6 ± 0.1 ** | 2.3 ± 0.3 ** | 5 / 5 † |

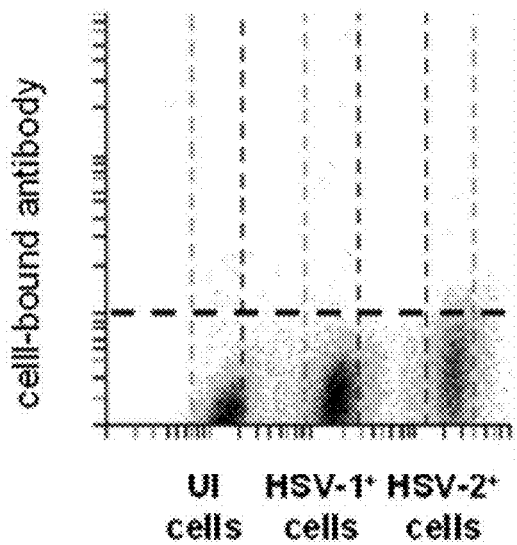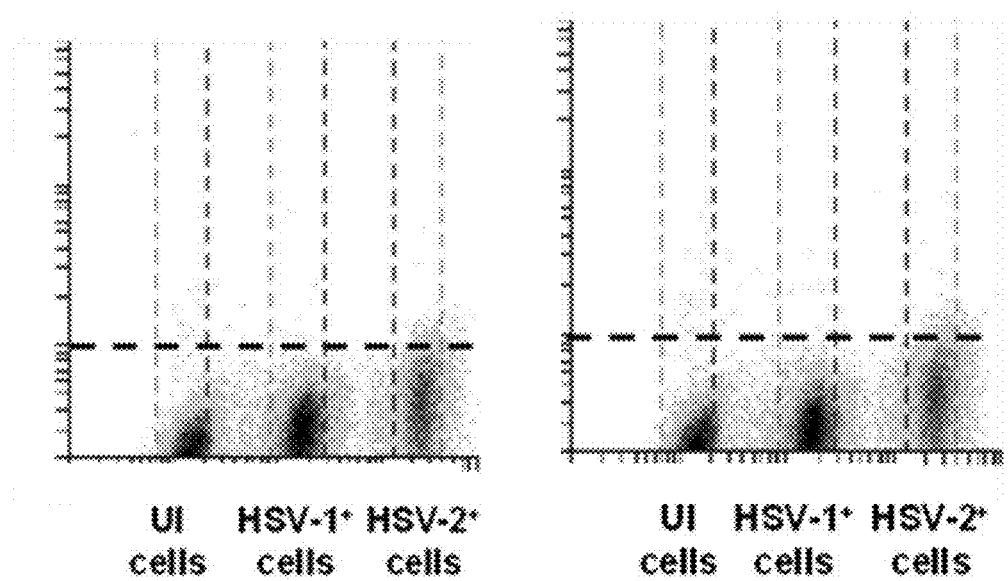
FIG. 15 Cont'd.

RAPID AND SENSITIVE SEROLOGICAL ASSAY TO DETERMINE IF PATIENTS ARE INFECTED WITH HERPES SIMPLEX VIRUS TYPE 1 HSV-1 AND/OR TYPE 2 HSV-2

CROSS-REFERENCE TO RELATED APPLICATIONS

This application claims priority to Patent Cooperation Treaty application PCT/US14/70915, filed Dec. 14, 2014, which claims priority from U.S. Provisional Patent application Ser. No. 61/917,584 that was filed on Dec. 18, 2013, whose disclosures are incorporated herein by reference.

BACKGROUND OF THE INVENTION

Fifty million Americans are infected with herpes simplex virus type 2 (HSV-2), but 80-90% of those infected are unaware that they carry HSV-2 [CDC, 2010; Paz-Bailey et al., 2007; Xu et al., 2006]. Regardless of whether patients have visible symptoms or not, they may shed infectious virus and transmit HSV-2 to sexual partners [Rattray et al., 1978; Tronstein et al:, 2011; Wald et al., 2000]. Antiviral drugs reduce, but do not eliminate, the risk of HSV-2 transmission [Sperling et al., 2008; Handsfield et al., 2007; Corey et al., 2004; DeJesus et al., 2003]. Patients who know they carry HSV-2 may take proactive steps to reduce the risk of transmission including antiviral drugs, condoms, disclosure to partners and awareness of subtle symptoms, all of which are effective tools in transmission reduction [Gupta et al., 2007; Rana et al., 2006; Warren, 2002; Wald et al., 2001].

The serological tests used to confirm a diagnosis of HSV-2 infection are imperfect. The most significant problems include (1) the HerpeSelect® HSV type-specific serological ELISA assay (Focus Diagnostics, a wholly-owned subsidiary of Quest Diagnostics, Inc.) may return false-positive results and (2) the confirmatory HSV Western blot test (i.e., the gold standard of HSV serology tests [Warren et al., 2011]) may return "indeterminate" results.

Patients with the potential for false-positives on the HSV-2 ELISA often score as "low-positives" with an index value of 1.1 to 3.5; 50% of these patients prove to be false-positive on the confirmatory HSV Western blot. However, confirmatory Western blot testing fails to resolve the serological status of about 50% of patients who obtained HSV-2 "low-positive" results from the HerpeSelect® ELISA test. Rather, Western blot testing typically returns indeterminate results for these patients. Thus, current HSV-2 serological testing leaves 2-4% of patients with ambiguous results [Ng'ayo et al., 2011; Golden et al., 2005], which for the purposes of this document are referred to as a "HSV-2 indeterminate" diagnosis.

Having an indeterminate diagnosis leaves patients wondering if they are infected with HSV-2, and causes needless anguish in patients who are not infected [Warren, 2002; Warren and Ebel, 2005]. Patients with an indeterminate diagnosis are forced to deal with the ramifications of a bona fide HSV-2 infection; specifically, they feel compelled to disclose their "HSV-2 status" to potential sex partners, risking possible rejection; they may take daily antiviral therapy to reduce the risk of infecting others; and they believe themselves to be 3 times more likely to acquire HIV infection than someone who does not have HSV-2 [Vergidis et al., 2009; Lingappa and Celum, 2007]. Repeat testing often fails to resolve their diagnosis, and thus patients may not know their HSV-2 infection status for months or years; this can have a profoundly negative impact on patients' self-perception and their quality of life.

There is thus an unmet need for an improved serological assay for diagnosis of HSV-2 infection that minimizes, or eliminates, HSV-2 indeterminate diagnoses. The present invention is a novel, flow cytometry-based serological assay that measures the affinity of serum antibody-binding to virus-infected cells (ABVIC) and is believed to be a more definitive HSV-2 serological test.

BRIEF SUMMARY OF THE INVENTION

The present invention provides a serological assay for determining whether a subject is infected with one or the other or neither of herpes simplex -1 or -2 viruses. Broadly, the assay comprises the steps of providing an antibody-containing serum or plasma (collectively, "serum") sample from the subject to be assayed. The serum sample contains antibodies that immunoreact with cell antigens present on HSV-1-infected (HSV-1$^+$) cells, or HSV-2-infected (HSV-2$^+$) cells, or cells infected with both HSV-1 and HSV-2, or cells infected with neither HSV-1 nor HSV-2.

The serum sample is divided into at least three subsample portions. A separate serum subsample portion is contacted and contact is maintained (incubated) of with each of: (a) antigens of cells uninfected with either HSV-1 or HSV-2 (HSV-1$^-$ or HSV-2$^-$), (b) antigens of cells infected with HSV-1 and (c) antigens of cells infected with HSV-2, thereby binding antibodies present in each subsample to one or more of the recited cell antigens. Each such incubated subsample portion is separated from the antibody-bound antigens, to form at least three preadsorbed serum samples, wherein the preadsorbed serum subsample incubated with uninfected cell antigens (a) contains a reduced amount of antibodies that immunoreact with uninfected cells, the preadsorbed serum subsample incubated with antigens of cells infected with HSV-1 (b) contains a reduced amount of antibodies that immunoreact with HSV-1-infected cells when those antibodies were present in the provided serum sample, and the preadsorbed serum subsample incubated with antigens of cells infected with HSV-2 (c) contains a reduced amount of antibodies that immunoreact with HSV-2-infected cells when those antibodies were present in the provided serum sample. Each of the preadsorbed subsample portions is admixed and incubated with a mixture of antigens from cells uninfected by either HSV-1 or HSV-2, cells infected by HSV-1 and cells infected by HSV-2, and determining to which one or more antigens the antibodies present in each subsample portions bound, and thereby whether the subject was infected with HSV-1, HSV-2, both or neither.

The assay in one embodiment comprises the steps of providing a serum or plasma (collectively, "serum") sample from the subject to be assayed, dividing the serum sample into at least three serum subsamples, preadsorbing the serum subsamples to at least three populations of antigens, preferably in the form of fixed cells, incubating the serum subsamples with at least three populations of free cells, incubating the serum subsamples with a detection antibody, and analyzing the serum subsamples with a cell sorting device or a flow cytometer.

A serological assay kit for determining whether a subject is infected with one, both or neither of herpes simplex -1 and -2 viruses is also contemplated. The kit comprises a) three separate vessels for serum preadsorption that separately contain i) antigens from uninfected cells in a physical matrix, (ii) antigens from HSV-1-infected cells in a same or different physical matrix, or (iii) antigens from HSV-2- infected cells in a same or different physical matrix from that of (i) or (ii). A fourth component of the kit are the test antigens, which may be provided in a variety of forms. In one embodiment, a fourth vessel is included in the kit that contains a mixture of three populations of uninfected cells, HSV-1-infected cells, and HSV-2 infected cells that have been (1) fixed and permeabilized and (2) differentially labeled with a fluorophore such that a cell sorting device or flow cytometer can differentiate each of the three populations. In this embodiment, preadsorbed serum separated from the antigen-containing matrices provided in kit vessels 1, 2, and 3, are separated from each matrix and combined with the test cells provided in kit vessel 4 to determine the relative abundance of HSV-1- and/or HSV-2-specific antibody in a cell sorting device or flow cytometer. Each of those four vessels contains a sufficient amount of the recited ingredient to carry out at least one assay. Instructions for carrying out an assay are preferably also be present in the kit.

The above-described serological assay kit further preferably includes a fifth vessel that contains labeled anti-human antibodies in an amount sufficient to carry out at least one assay. The label of the anti-human antibodies is preferably a fluorescent material whose fluorescence is distinguishable from the fluorescence of any other material present. It is also preferred that the mixture of fixed test cells of the fourth vessel-further include an exogenously-introduced fluorescent colorant by which cells containing uninfected, HSV-1, or HSV-2 antigens are distinguishable from each other by fluorescence, and are also distinguishable from any other fluorescent species utilized in the assay.

The present invention has several benefits and advantages.

One benefit is that many antibody assays are sufficient to distinguish HSV-seronegative from HSV-seropositive samples, but do not differentiate whether a person is infected with HSV-1, HSV-2, or both.

An advantage of the invention is that the HSV-1-specific antibody assay portion of the invention differentiates whether or not a person is infected with HSV-1, and corroborates the results of a Herpes Western Blot.

Another benefit of the invention is that the HSV-2-specific antibody assay portion differentiates whether or not a person is infected with HSV-2, and corroborates the results of a Herpes Western Blot.

Another advantage of the invention is that the preferred Type-Specific ABVIC assay combines (i) an uninfected control assay, (ii) a HSV-1-specific antibody assay, and (iii) a HSV-2-specific antibody assay.

A further benefit of the invention is that the preferred Type-Specific ABVIC assay is highly quantitative and permits for statistical interpretation of the probability that a person is HSV-1 and/or HSV-2 seropositive.

A further advantage is that the quantitative and statistical power of a preferred Type-Specific ABVIC assay permits the assay to resolve Indeterminate Test Results of Herpes Western Blot tests.

An additional benefit of the invention is that the increased sensitivity and quantitative power of the Type-Specific ABVIC assay relative to the Herpes Western Blot can permit a preferred Type-Specific ABVIC assay to be carried out more rapidly than the usual Western blot-formatted assay, while maintaining the ability to distinguish infection by HSV-1 from infection by HSV-2.

An additional advantage of the invention is that it can provide more sensitive results than the commercial HerpeSelect® test ELISA assay because a preferred type-specific ABVIC assay screens for the presence of antibodies against up to 75 HSV-1 or HSV-2 proteins that can be present in the fixed and permeabilized test cells described above. In contrast, the HerpeSelect® ELISA tests for antibodies against only 1 of 75 HSV-1 or HSV-2 proteins; namely, glycoprotein G.

Still further benefits and advantages will be apparent to the skilled worker from the description that follows.

BRIEF DESCRIPTION OF THE DRAWINGS

FIGS. 1A and 1B show immunofluorescent labeling of fixed HSV-2 plaques with a 1:6,000 dilution of (A) naïve mouse serum or (B) HSV-2 antiserum obtained from mice immunized with HSV-2 0ΔNLS [Halford et al., 2010]. Mouse IgG binding was visualized with AlexaFluor594-labeled goat anti-mouse IgG (H+L).

FIGS. 1C and 1D show two-color flow cytometric analysis of a fixed, single-cell suspension of CFSE-labeled, HSV-2-infected (HSV-2$^+$) Vero cells mixed with uninfected (UI) Vero cells. Fixed cells were incubated with a 1:6,000 dilution of (C) naïve mouse serum or (D) mouse HSV-2 antiserum and APC-labeled goat anti-mouse IgG, and were analyzed for CFSE (FL1) and APC (FL4) fluorescent intensity.

FIG. 1E shows pan-HSV-2 IgG levels in the serum of n=6 naïve mice versus n=6 HSV-2 0ΔNLS-immunized mice, as determined by the ΔMFI between HSV-2$^+$ and UI cells.

FIG. 2A shows the design of the vaccine-ocular HSV-2 challenge experiment in mice. Mice were initially inoculated in their right eye on Day 0 with culture medium or $10^5$ plaque-forming units (pfu) per eye of one of the five indicated viruses (n=8 per group). Mice inoculated with HSV-2 MS were treated with acyclovir from Days 0 to 20 post-immunization to restrict viral pathogenesis. On Day 60, blood was harvested, and on Day 70, mice were challenged in the left eye with $10^5$ pfu of wild-type HSV-2 MS.

FIG. 2B shows the mean±sem pan-HSV-2 IgG levels in pre-challenge serum, as determined by a flow cytometry-based assay.

FIG. 2C shows for each mouse (one symbol per mouse), the average amount of infectious HSV-2 shed on Days 1, 2, and 3-post ocular challenge (y-axis) plotted as a function of the pre-challenge HSV-2 IgG levels observed in the same mouse (x-axis). The solid black line represents the best-fit linear regression model, y=3.35−0.56x, for the 48 matched datum pairs.

FIG. 2D shows the mean±sem of log (pan-HSV-2 IgG) in each immunization group plotted on the x-axis versus mean±sem ocular HSV-2 shedding on the y-axis. The solid black line represents the best-fit linear regression model, y=3.44−0.64x, for these 6 matched averages ($r^2$=0.86). Groups of immunized mice that exhibited a significant reduction in ocular HSV-2 shedding relative to naïve mice are indicated by a single asterisk (*p<0.05) or double-asterisk (**p<0.001), as determined by one-way ANOVA and Tukey's post-hoc t-test.

FIG. 2E shows the survival frequency in each group plotted as a function of the mean±sem pan-HSV-2 IgG antibody level observed in each group. Groups of immunized mice that exhibited a significant difference in survival frequency relative to naïve mice are indicated by a single asterisk (*p<0.05) or double-asterisk (**p<0.0001), as determined by Fisher's Exact Test.

FIG. 3A shows the design of the mouse vaccine-challenge experiment. Mice were immunized in their right, rear footpads on Day 0 with gD-2, GFP, culture medium (mock), HSV-2 0ΔNLS, or HSV-2 MS, as described in the Results (n=10 per group). Mice immunized with HSV-2 MS received 1 mg/ml acyclovir in drinking water from Days 0 to 20 post-immunization to restrain the pathogenesis of a primary exposure to wild-type HSV-2. All mice were boosted in their left, rear footpads on Day 30 with an equivalent, booster immunization with the exception that MS-immunized mice did not require acyclovir during the boost. On Day 60, blood was harvested, and on Days 90 or 100, mice were challenged with 500,000 pfu per vagina of wild-type HSV-2 MS. Seven and 3 days prior to HSV-2 MS challenge, each mouse received a subcutaneous injection of 2 mg DepoProvera® (medoxyprogesterone) to render mouse vaginas susceptible to HSV-2 challenge.

FIG. 3B shows the mean±sem pan-HSV-2 IgG levels in pre-challenge serum, as determined by a flow cytometry-based assay. The frequency with which mice survived until Day 30 post-challenge is indicated.

FIG. 3C shows the average amount of infectious HSV-2 shed on Days 1, 3, 5, and 7 post-vaginal challenge for each mouse (one symbol per animal; y-axis) plotted as a function of pre-challenge pan-HSV-2 IgG levels observed in the same mouse (x-axis). The solid black line represents the best-fit linear regression model, y=3.85−0.76x, for the 50 matched datum pairs.

FIG. 3D shows the mean±sem of log (pan-HSV-2 IgG) in each immunization group plotted on the x-axis versus mean±sem vaginal HSV-2 shedding on the y-axis. The solid black line represents the best-fit linear regression model, y=3.89−0.79x, for these 5 matched averages ($r^2$=0.98). Groups of immunized mice that exhibited a significant reduction in vaginal HSV-2 shedding relative to naïve mice are indicated by a single asterisk (*$p<0.05$) or double-asterisk. (**$p<0.001$), as determined by one-way ANOVA and Tukey's post-hoc t-test.

FIG. 4A shows the design of the guinea pig vaccine-challenge experiment. Guinea pigs were immunized in their right, rear footpads on Day 0 with gD-2, culture medium (mock), HSV-2 0ΔNLS, or HSV-2 MS (n=5 per group). Guinea pigs immunized with HSV-2 MS received 1 mg/ml acyclovir in drinking water from Days 0 to 20 post-immunization to restrain the pathogenesis of a primary exposure to wild-type HSV-2. All guinea pigs were boosted in their left, rear footpads on Day 30 with an equivalent, booster immunization. MS-immunized guinea pigs did not receive acyclovir during the secondary boost. On Day 75, blood was harvested, and on Day 90, guinea pigs were challenged with 2×10⁶ pfu per vagina of wild-type HSV-2 MS.

FIG. 4B shows the mean±sem pfu of HSV-2 shed per vagina between Days 1 and 8 post-challenge in guinea pigs that were naïve (n=5) or were immunized with gD-2+alum/MPL (n=4), HSV-2 0ΔNLS (n=5), or an acyclovir (ACV)-restrained HSV-2 MS infection (n=5). A single asterisk (*) denotes $p<0.05$ and a double asterisk (**) denotes $p<0.0001$ that HSV-2 MS vaginal shedding was equivalent to naïve guinea pigs on that day, as determined by one-way ANOVA and Tukey's post hoc t-test.

FIG. 4C shows for each guinea pig (one symbol per animal), the average amount of infectious HSV-2 shed on Days 1, 2, 3, 4, 6, and 8 post-vaginal challenge (y-axis) plotted as a function of pre-challenge pan-HSV-2 IgG levels observed in the same guinea pig (x-axis). The solid black line represents the best-fit linear regression model, y=3.77−0.95x, for these 19 matched datum pairs.

FIG. 4D shows the mean±sem of log (pan-HSV-2 IgG) in each immunization group plotted on the x-axis versus mean±sem vaginal HSV-2 shedding on the y-axis. The solid black line represents the best-fit linear regression model, y=3.77−0.95x, for these four matched averages ($r^2$=0.98). Groups of immunized guinea pigs that exhibited a significant reduction in vaginal HSV-2 shedding relative to naïve guinea pigs are indicated by a single asterisk (*$p<0.05$) or double-asterisk (**$p<0.001$), as determined by one-way ANOVA and Tukey's post-hoc t-test.

FIG. 4E shows the worst case of perivaginal disease in each group of naïve or immunized guinea pigs on Day 7 post-challenge. Survival frequency refers to the frequency with which animals in each immunization group survived until Day 30 post-challenge.

FIGS. 5A and 5B show the mean±sem of HSV-2 shedding from mouse eyes on (A) Day 1 and (B) Day 3 post-challenge (n=5 per group).

FIG. 5C shows the mean±sem duration of survival of each group of mice. Numbers over each bar report the frequency of 'survival' and 'disease incidence' in each group of mice. Significant increases in the duration of survival relative to naïve mice are indicated by a single asterisk (*$p<0.05$) or double asterisk (**$p<0.001$), as determined by one-way ANOVA and Tukey's post-hoc t-test.

FIG. 6 shows a comparison of three methods used to measure serum levels of HSV-2-specific antibodies. [a]Range of HSV-2 antiserum dilutions in which estimates of anti-HSV-2 antibody abundance changed in linear relation to changes in serum dilution. [b]Mean±sem coefficient of variation of triplicate measurements for each serum dilution in the linear range of each assay. For each serum dilution considered, the coefficient of variation=100×standard deviation÷mean. [c]Goodness-of-fit ($r^2$) of observed data relative to values predicted by a regression model within the linear range. The p-value refers to the probability that the quantity measured by each assay (i.e., neutralizing titer, $OD_{405}$, or ΔMFI) did not vary as a function of HSV-2 antiserum dilution.

FIG. 7 shows that pan-HSV-2 IgG antibody levels correlate with protection against vaginal HSV-2 MS challenge in mice and guinea pigs. [a]Animals were immunized with each immunogen, as described in FIGS. 3A and 4A. [b]Naïve and immunized mice correspond to animals presented in FIG. 3. Guinea pigs correspond to animals presented in FIG. 4. [c]Mean±sem of log (pan-HSV-2 IgG) correspond to x-variables in FIG. 3C for mice, and correspond to x-variables in FIG. 4C for guinea pigs. [d]Mean±sem of log (reduction in vaginal HSV-2 shedding) was derived from the y-variables presented in FIG. 3C for mice, and was derived from the y-variables presented in FIG. 4C for guinea pigs. [e]Frequency of animals that survived until Day 30 post-HSV-2 vaginal challenge. [f]Not determined. *$p<0.05$, as determined by one-way ANOVA and Tukey's post-hoc t-test comparing immunized versus naïve animals of the same species. **p<0.001, as determined by one-way ANOVA and Tukey's post-hoc t-test comparing immunized versus naïve animals of the same species. †p=0.01, as determined by Fisher's Exact Test comparing the frequency of survival of immunized versus naïve animals of the same species. \\p=0.00001, as determined by Fisher's Exact Test comparing the frequency of survival of immunized versus naïve animals of the same species.

FIG. 8A shows HSV-2 neutralizing activity in a 0.33-log dilution series of mouse HSV-2 antiserum. Neutralizing antibody titer is reported as the mean±sem of n=3 replicates per dilution.

FIG. 8B shows antibody capture ELISA-based measurement of pan-HSV-2 IgG antibody levels in a 0.33-log dilution series of HSV-2 antiserum (mean±sem of n=3 replicates per dilution).

FIG. 8C shows flow cytometry-based measurement of pan-HSV-2 IgG antibody levels in a 0.33-log dilution series of HSV-2 antiserum (mean±sem of n=3 replicates per dilution). The dashed lines represent the lower limit of detection of each assay.

FIG. 9A shows the standard curve of antibody-capture ELISA. Open circles indicate the colorimetric development ($OD_{405}$) observed in ELISA wells that received 0.33-log dilutions of HSV-2 antiserum (mean±sd; n=4 per dilution). The sigmoidal relationship between $OD_{405}$ and log (pan-HSV-2 IgG) was precisely described using the hyperbolic tangent equation shown ($r^2=1.00$), and a reciprocal hyperbolic arctangent equation (defined in Methods) was used to derive pan-HSV-2 IgG levels in test serum samples from the $OD_{405}$ values observed in ELISA.

FIG. 9B shows for each mouse (one symbol per mouse), the average amount of infectious HSV-2 shed on Days 1, 2, and 3-post ocular challenge (y-axis) plotted as a function of the pre-challenge pan-HSV-2 IgG levels, as estimated by ELISA (x-axis). The solid black line represents the best-fit linear regression model, y=3.05×0.57x, for the 48 matched datum pairs.

FIG. 9C shows ELISA-versus flow cytometry-estimates of log (pan-HSV-2 IgG) plotted as x,y-datum pairs relative to a 0-log "line of equivalence." Datum points beyond the "+1 log" reference line indicate serum samples in which flow cytometry estimates of pan-HSV-2 IgG levels were 1 logarithm greater than the ELISA estimate of pan-HSV-2 IgG for the same serum sample.

FIG. 10A shows a seronegative individual.

FIG. 10B shows a HSV-2 genital herpes patient.

FIG. 10C shows indeterminate serum sample 1.

FIG. 10D shows indeterminate serum sample 3. Human IgG binding to test cells (y-axis) was detected with APC-conjugated anti-human γ-chain.

FIG. 12A shows cells stained with seronegative serum.

FIG. 12B shows cells stained with HSV-2 seropositive serum.

FIG. 12C shows cells stained with indeterminate serum sample 3. Patient serum samples were preadsorbed to UI Vero cells (left), HSV-1+ cells (center); and HSV-2+ cells (right). Boxes in the center column indicate the predicted position of HSV-2+ cells if serum contains HSV-2-specific antibodies. Boxes in the right column indicate the predicted position of HSV-1+ cells if serum contains HSV-1-specific antibodies.

FIG. 13A is a pie chart representing all possible HSV-specific antibodies in a person infected with HSV-1 and/or HSV-2.

FIG. 13B illustrates that HerpeSelect® ELISAs test for gG-specific antibodies.

FIG. 13C illustrates that gG-specific antibodies represent only 3-10% of total repertoire of HSV-1 or HSV-2 specific-antibodies that could be used to measure a patient's HSV serological status.

FIG. 21A shows a normal distribution of the calculated "Normalized Cell-Bound Antibody" value, and indicates that at an abscissa value of about 3.6 and above, the probability, p, is less than 0.05 that a patient is HSV-seronegative for the particular population of antibodies being tested (i.e., UI preadsorbed tests for total HSV-antibody; HSV-1 preadsorbed tests for HSV-2-specific antibody; and HSV-2 preadsorbed tests for HSV-1-specific antibody).

FIG. 21B shows that because "Normalized Cell-Bound Antibody" is normally distributed, one can calculate the probability of a given sample being X-fold above the average of seronegative samples, which by the definitions used for these calculations, always have a mean "Normalized Cell-Bound Antibody" value of 1.0. Per this graph and the underlying math, a sample whose "Normalized Cell-Bound Antibody" value=5.0 only has a probability, p,=0.005 of being a seronegative sample that yielded a higher value due to random sampling variation. The $p<0.05$ cutoff is shown as a dashed line.

FIG. 22A, illustrates serum that was preadsorbed to a HSV-1 antigen matrix, and therefore should contain HSV-2-specific antibodies if they were originally present in the patient sample. None of the 7 "Indeterminate" samples tested were significantly different from the normal distribution of known HSV-seronegative samples (i.e., $p>0.05$), whereas all of the known HSV-2$^+$ were highly significant ($p<0.0001$). FIG. 22A also illustrates that preadsorption works well, and so sera of HSV-1$^+$ patients are negative for HSV-2-specific antibodies (same as seronegatives) after being preadsorbed to a HSV-1 cell antigen matrix. FIG. 22 B illustrates analogous results to those of FIG. 22A when data for HSV-2-specific antibodies is plotted rather than data for HSV-1-specific antibodies.

DETAILED DESCRIPTION OF THE INVENTION

Figure 1:
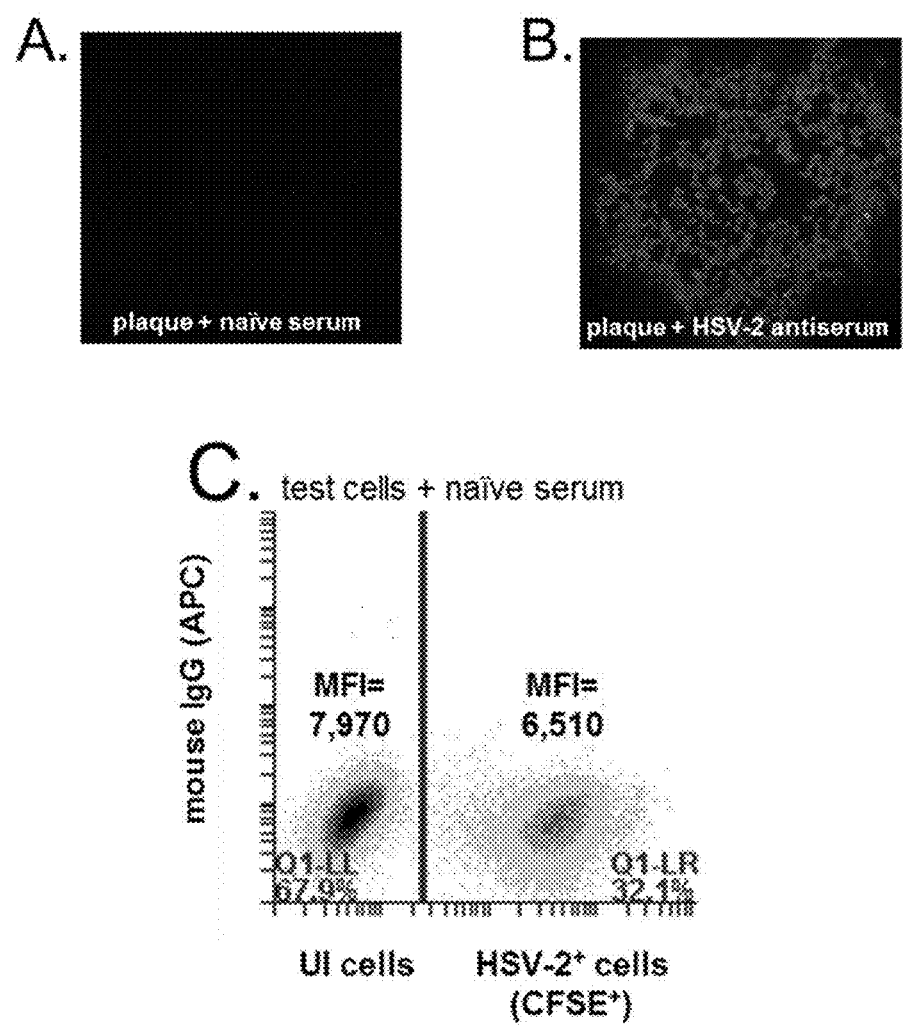
FIG. 1 shows flow cytometry-based measurement of pan-HSV-2 IgG antibody levels.
Figure 1:
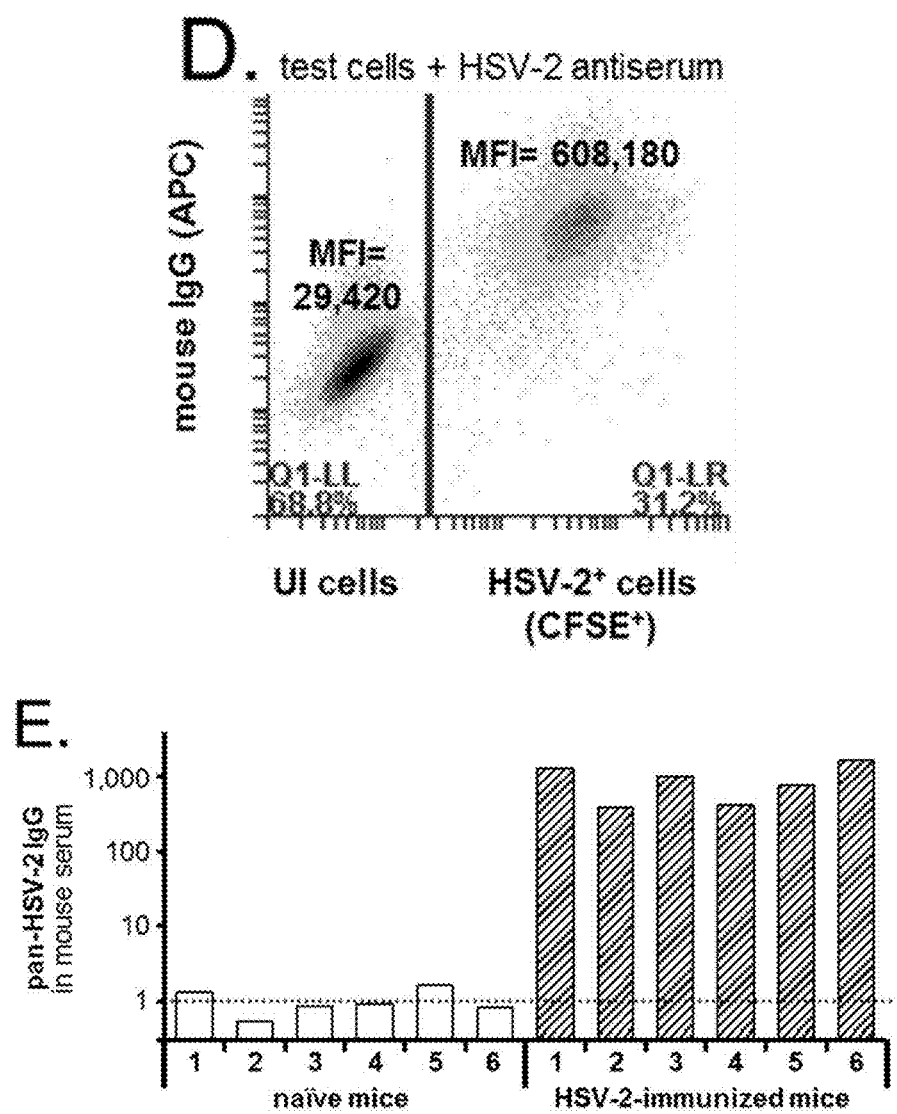

The present invention contemplates an assay that can detect and differentiate between infection by one or both or neither of HSV-1 and HSV-2 for the purposes of disease diagnosis from a subject serum sample. One preferred illustrative embodiment contemplates a three cell population assay that is referred to herein as a flow cytometry-based serological assay that measures the virus type-specific affinity of serum antibody-binding to virus-infected cells (AB-VIC).

The present invention contemplates use of an antibody-containing sample from a patient whose infection status with one, the other, both or none of HSV-1 and HSV-2 is to be determined. Usually, that sample is in the form of serum or plasma from a blood draw sample. The sample can also be an antibody-enriched sample such as an ammonium sulfate precipitate from a blood or other sample as are well known, or from a dried, e.g. lyophilized, serum or plasma sample. For convenience and because of their similarity, serum and plasma are collectively referred to herein as serum.

The patient (subject) sample is divided into at least three portions or subsamples. Each portion (subsample) is separately admixed and contacted with (a) antigens from uninfected cells, (b) with antigens from HSV-1-infected cells and (c) with antigens from HSV-2-infected cells.

That contact is maintained for a time period sufficient for antibodies within the subsample that immunoreact with the recited antigens to immunoreact (bind) therewith. That contact and maintenance is also referred to herein as incubation. Maintenance times can range from a few minutes to about 96 hours. Usually, the maintenance time is about 1 to about 8 hours, and more preferably about 2 to about 6 hours.

The above-mentioned cell antigens are themselves part of a physical matrix so that the reacted antibodies form physical matrix-bound antibodies (also referred to as matrix-bound antibodies). Illustrative physical matrices include, for example, 1) a protein-coated solid matrix (e.g., ELISA plate); 2) a cell-coated solid matrix (e.g., culture plate coated with fixed cells); 3) free-floating particles (e.g., live or fixed cells in liquid suspension); 4) a column of particles (e.g., live or fixed cells in a capillary tube); 5) protein-coated magnetic beads; 6) a slurry of protein-coated matrix (e.g., antigen-reacted CNBr-activated Sepharose® 4B) suspended in liquid, or packed into a flow-through column.

Slurries of fixed and permeabilized uninfected (UI) cells, HSV-1$^+$ cells and HSV-2$^+$ cells were used illustratively herein. As is well known in the biological arts, cell fixation can be achieved by a wide variety of chemicals including, but not limited to treatment with one or more of formaldehyde, paraformaldehyde, methanol, ethanol, and acetone. It is preferred that the cells used as each of the physical matrices be of the same type. Illustrative cell types include 1) human SK—N—SH neuroblastoma cells; 2) human U2OS osteosarcoma cells; 3) human 293 embryonic kidney cells; 4) monkey CV-1 kidney cells (Vero cells); 5) monkey COS cells; 6) mouse 3T3 cells; 7) hamster BHK-21 cells; 8) bovine BIEC cells; 9) bovine BUVEC cells; 10) human Caco-2 cells; 11) human HeLa cells; 12) monkey MA104 cells; 13) canine MDCK cells; 14) pig PK-15 cells; and 15) human WiDr cells.

It is noteworthy that HSV ICP0$^-$ viruses form plaques with an efficiency that is indistinguishable from Vero cells in 11 of 15 other cell lines tested to date. Specifically, work by the inventor and co-workers indicates that 0.5-2% of HSV ICP0$^-$ viruses form plaques in monolayers of human 293 cells, mouse 3T3 cells, hamster BHK-21 cells, bovine BIEC cells, bovine BUVEC cells, human Caco-2 cells, human HeLa cells, monkey MA104 cells, canine MDCK cells, pig PK-15 cells, and human WiDr cells. Thus, any cell line in this list, by definition, supports replication of wild-type HSV-1 and HSV-2 as well as the mutant HSV-1 virus specifically discussed in the text. Vero cells are one preferred cell type and are used hereinafter as illustrative.

The cells used can themselves be attached to a solid, physical matrix (e.g., plastic dish, magnetic beads, agarose, etc.) or can be suspended in a liquid solution such as an aqueous medium like a buffer solution such as PBS. The physical matrix-bound (immunoreacted) antibodies are thereafter separated from any unreacted antibodies present in the reacted subsample. This separation can be carried out by centrifugation and decantation or pipetting out the supernatant liquid, pipette removal as where the antigen-bound antibody is on the walls of a culture plate, elution and the like.

The above-discussed admixing and incubation of each of three serum samples with a different one of the cell antigen-matrices is also referred to herein as preadsorption. That preadsorption is preferably carried out with fixed cells. It is preferred that the same cell type be used for each of the preadsorptions to minimize possible differing cross-reactivities.

Figure 19:
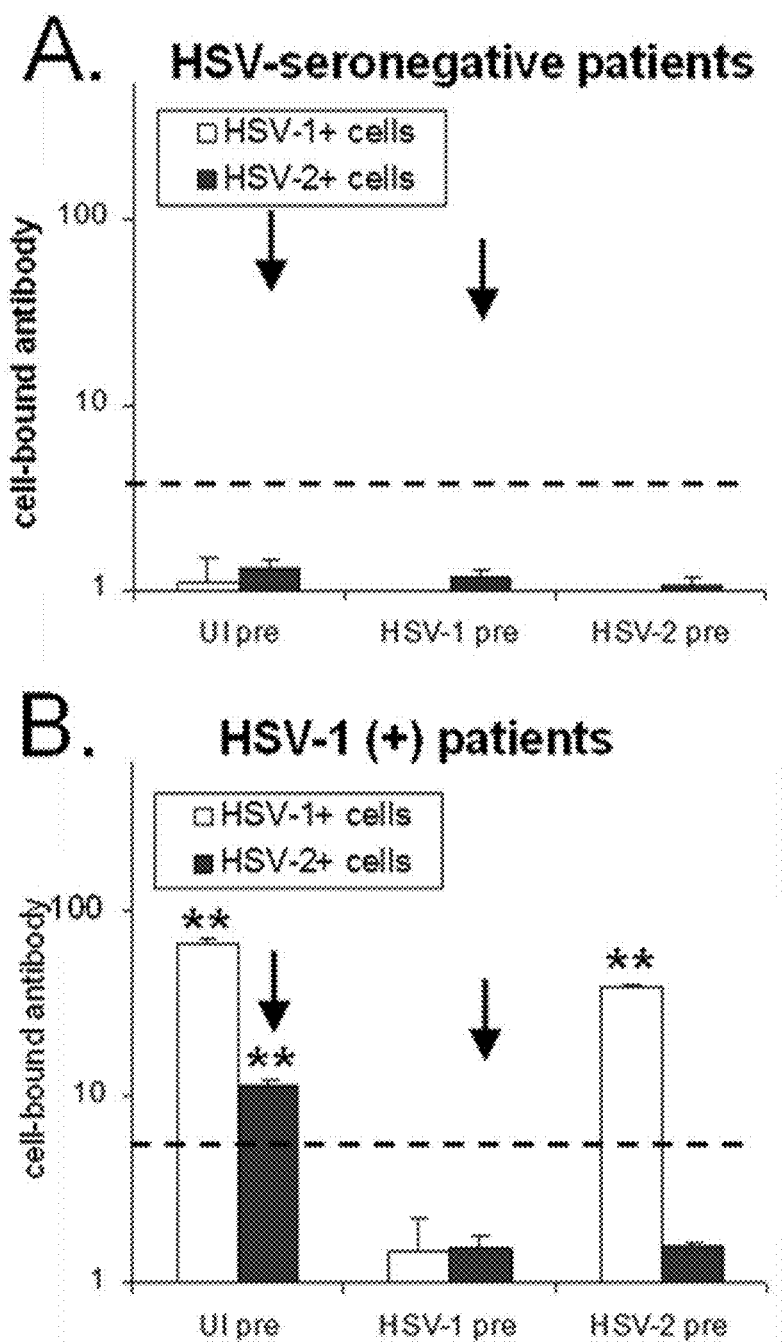
FIG. 19, in three panels as FIG. 19A, FIG. 19B, and FIG. 19C, is a graphical summary of the results of three of the control groups, namely n=5 HSV-seronegative patients (FIG. 19A), n=2 HSV-1$^+$ patients (FIG. 19B), and n=2 HSV-2$^+$ patients (FIG. 19C). The black arrows pointing down in each FIG. show the expected height of the red bars (i.e., antibody bound to HSV-2$^+$ cells) if the patient were indeed infected with HSV-2. These conditions are met in HSV-2$^+$ patients, but the type-specific ABVIC test easily discriminates people who are (A) seronegative or (B) HSV-1$^+$. Importantly, the dashed line indicates the cutoff for statistical significance ($p<0.05$), and the bars that are positive in these graphs represent highly significant differences ($p<0.0001$).
Figure 19:
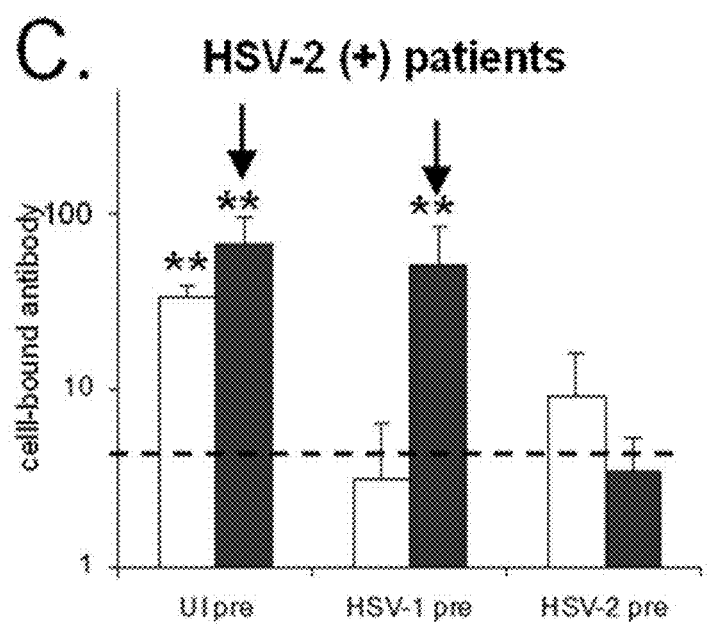
Figure 20:
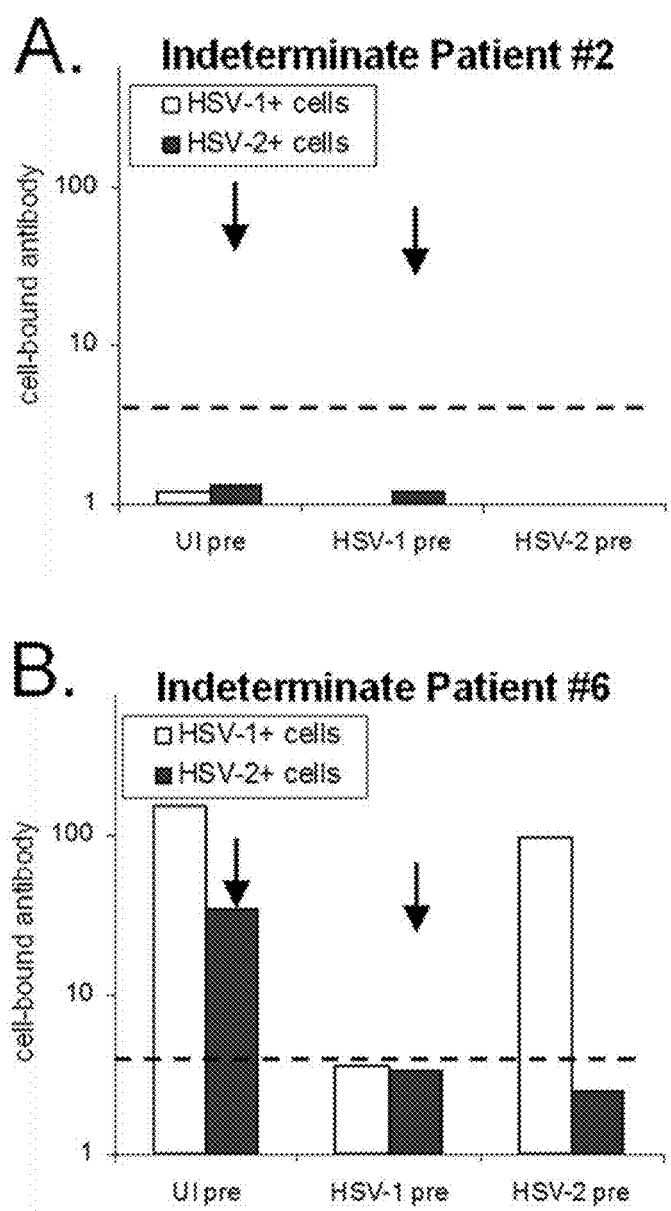
FIG. 20, in two panels as FIG. 20A and FIG. 20B, is a graphical summary of the results of two representative "Indeterminate Patients" as determined by the type-specific ABVIC Assay results shown in FIGS. 17 and 18. Out of n=7 Indeterminate Patients screened in this test, n=3 were HSV-seronegative like Patient #2 shown in FIG. 20A, and n=4 were HSV-1-seropositive like Patient #6 shown in FIG. 20B. The black arrows pointing down in each panel show the expected height of the red bars (i.e., antibody bound to HSV-2$^+$ cells) if the patient were indeed infected with HSV-2. The dashed line indicates the cutoff for statistical significance ($p<0.05$), so the test data indicate that the probability is very low that these individuals are HSV-2-seropositive (e.g., $p<0.0001$).

The purpose of the uninfected cell antigen matrix, in whichever specific form it is used, is to serve as a "PreAdsorption Treatment Control" that has little to no effect on the population of human serum antibodies in a test sample taken from a patient seeking to determine if they are infected with HSV-1 and/or HSV-2 (leftmost panels of raw data in FIGS. 15-18, and graphical summaries in FIGS. 19 and 20).

Similarly, the purpose of the HSV-1$^+$ cell antigen matrix, in whichever specific form it is used, is to remove (1) HSV-type-common antibodies and (2) HSV-1-specific antibodies from a patient's serum sample. Hence, the effluent that is removed after incubation with the HSV-1$^+$ cell antigen matrix yields a highly enriched population of HSV-2-specific antibodies, which may be used to determine if a patient has been infected with the HSV-2 virus (center panels of raw data in FIGS. 15-18, and graphical summaries in FIGS. 19 and 20).

Likewise, the purpose of the HSV-2$^+$ cell antigen matrix, in whichever specific form it is used, is to remove (1) HSV-type-common antibodies and (2) HSV-2-specific antibodies from a patient's serum sample. Hence, the effluent that is that is removed after incubation with the HSV-2$^+$ antigen matrix provides a highly enriched population of HSV-1-specific antibodies, which may be used to determine if a patient has been infected with the HSV-1 virus (rightmost panels of raw data in FIGS. 15-18, and graphical summaries in FIGS. 19 and 20).

As a result of the preadsorptions, at least three preadsorbed serum subsamples are formed. Thus, the preadsorbed serum subsample incubated with uninfected cell antigens (a) contains a reduced amount of antibodies that immunoreact with uninfected cells. The preadsorbed serum subsample incubated with antigens of cells infected with HSV-1 (b) contains a reduced amount of antibodies that immunoreact with HSV-1-infected cells when those antibodies were present in the provided serum sample, and thereby a relatively enhanced amount of antibodies that immunoreact with HSV-2, when those antibodies were present in the provided serum sample. Similarly, the preadsorbed serum subsample incubated with antigens of cells infected with HSV-2 (c) contains a reduced amount of antibodies that immunoreact with HSV-2-infected cells when those antibodies were present in the provided serum sample, and a relatively enhanced amount of antibodies that immunoreact with HSV-1, when those antibodies were present in the provided serum sample.

Each of the preadsorbed subsample portions is incubated (as discussed above) with a mixture of second matrix-linked test antigens from cells uninfected by either HSV-1 or HSV-2, test antigens from cells infected by HSV-1 and test antigens from cells infected by HSV-2 to permit antibodies present within each subsample to immunoreact with test antigens present. The amount of immunoreaction, including little or no immunoreaction, is then determined for each of the subsamples with the test antigen mixture to determine with which test antigens, if any, the antibodies from the preadsorbed subsamples immunoreacted.

The second matrix-linked test antigens utilized in this portion of the assay can be the same test antigen-physical matrix constructs discussed before, or different constructs. In one preferred embodiment, the mixture of the three test antigen-physical matrices is comprised of fixed and permeabilized cells that are (a) unstained, (b) weakly stained with a cellular dye, fluorophore, or colorant and (c) strongly stained with the same exogenously-provided cellular dye, fluorophore, or colorant, so that each population of test cells can be distinguished from each other on the basis of their relative amounts of dye color or fluorescence.

A particularly preferred exogenously-provided (not normally present as part of the cells) cellular colorant is fluorescent upon irradiation, typically with defined wavelengths of light in the ultraviolet, visible, or infrared range (200-800 nm), and its fluorescence can be detected by a flow cytometer. Illustrative useful exogenously-provided chemically reactive (covalently-linkable) fluorescent colorants include but are not limited to 5- (and 6)-carboxyfluorescein diacetate succinimidyl ester (CFSE), (CellTrace™ Violet), and 2,5-dioxopyrrolidin-1-yl-7-(2-(((1E,3E,4E)-1,5-dichloro-6-oxohexa-1,4-dien-3-ylidene)amino)-5-hydroxyphenyl)octanoate (CellTrace™ Far Red DDAO-SE) that couple to amino groups such as epsilon-amino groups of lysine residues via N-hydroxysuccinimide ester exchange, and chloromethyl reactive colorants such as (2,3,6,7-tetrahydro-9-bromomethyl-1H,5H-quinolizino(9,1-gh))-coumarin (CellTracker™ Violet BMQC), 7-amino-4-chloromethyl-coumarin (CellTracker™ Blue CMAC), 5-chloromethyl-fluorescein diacetate (CellTracker™ Green) and 5-chloromethylrhodamine (CellTracker™ Red) (all available from Life Technologies, Thermo Fisher Scientific) that stain the cells via reaction with cellular thiol groups. Cells can also be differentially labeled with one or more intracellularly-expressed fluorescent proteins including, but not limited to green fluorescent protein (GFP), mCherry, tdTomato, KeimaRed, yellow fluorescent protein (YFP), cyan fluoresent protein (CFP) as discussed for GFP in Chalfie et al., (1994) *Science* 263:802-805.

The exogenously-introduced fluorescent colorant provides a means by which each population of test cell antigens are distinguishable from each other by fluorescence. Fluorescence emission from the exogenously-provided cellular colorant of the test cell antigen-containing matrices is distinguishable from the fluorescence emission of the secondary antibodies discussed hereinafter, and fluorescence of any other material present in the assay.

In one preferred embodiment, the amount of immunoreaction is determined for each preadsorbed serum subsample that is combined with test cells, and human antibody binding to each population of test cells is detected by secondary labeling with anti-human antibodies that are admixed with test cells. A preferred label for the anti-human antibodies is a covalently-linked fluorescent compound whose fluorescence emission spectrum does not overlap with the fluorescence emission spectrum of the colorant used to differentially label (i) uninfected, (ii) HSV-1-infected, and (iii) HSV-2-infected antigen matrices. Illustrative covalently-linkable fluorescent dyes that can be conjugated to a secondary anti-human antibody include, but are not limited to, allophycocyanin (APC), phycoeryrthrin (PE), tetramethylrhodamine isothiocyanate (TRITC), and peridinin chlorophyll protein (PerCP).

It is preferred that any unreacted antibodies from the preadsorbed subsamples be separated from the immunoreaction products as previously discussed.

In addition to using a fluorescent label for the anti-human (secondary) antibodies, enzyme labels such as horseradish peroxidase (HRP), alkaline phosphatase and glucose oxidase can be covalently conjugated to the secondary antibodies as are often utilized in ELISA assays with an appropriate chromogenic substrate as are well known.

The anti-human (secondary) antibodies are themselves raised in an animal other than a human. Illustrative secondary antibodies include those raised in goats, donkeys, horses, rabbits, mice and rats. These anti-human antibodies preferably react with human Fc antibody portions.

On determining to which test cell antigens the antibodies present in each preadsorbed subsample portions bound, one can thereby ascertain whether the patient was infected with HSV-1, HSV-2, both or neither.

Any method of detecting immunofluorescence can be used to determine which, if any, of the preadsorbed subsamples bound to the test cell antigens including but not limited to fluorescent microscopy, a fluorescent plate reader, a flow cytometer, or a fluorescence-activated cell sorter. Preferably, a flow cytometer or FACS is utilized as such machines can measure both (1) the differential fluorescent color that indicated whether the test cell antigen-containing matrix were uninfected, HSV-1$^+$, or HSV-2$^+$, and the instrument simultaneously measures (2) a second fluorescent color that is indicative of the primary variable under study; namely, the amount of human antibody bound to uninfected versus HSV-1$^+$ versus HSV-2$^+$ test cell antigens.

The discussion hereinafter describes a particularly preferred assay that utilizes fixed cells as the test cell antigen-containing matrices.

The present invention also contemplates a serological assay kit for carrying out a before-described assay. An illustrative kit includes a) three separate vessels that separately contain one of i) cell antigens from uninfected cells in a physical matrix, (ii) cell antigens from HSV-1-infected cells in a same or different physical matrix, or (iii) cell antigens from HSV-2-infected cells in a same or different physical matrix from that of (i) or (ii).

A fourth vessel is also included. The fourth vessel contains a mixture of test cell antigens from cells uninfected by either HSV-1 or HSV-2, antigens from cells infected by HSV-1, and antigens from cells infected by HSV-2, each of those cell antigens linked to a second matrix that is the same or different from the first-named matrix. Each of those four vessels contains a sufficient amount of the recited ingredient to carry out at least one assay.

Instructions for carrying out an assay are also present in the kit. A contemplated kit is preferably provided as a container that holds the recited components.

The vessels of a contemplated assay kit are typically made of glass or a plastic to which the recited reagents adhere poorly such as to polyethylene glycol (PEG) coatings and coatings of polytetrafluoroethylene (PTFE).

The above-described serological assay kit further preferably includes a fifth vessel that contains labeled anti-human antibodies in an amount sufficient to carry out at least one assay. The label of the anti-human antibodies is preferably a fluorescent material whose fluorescence is distinguishable from the fluorescence of any other material present. It is also preferred that the mixture of fixed cells of the fourth vessel further include an exogenously-introduced fluorescent colorant by which each population of test cell antigen matrices is distinguishable from the others by the intensity of fluorescent emissions in a defined wavelength, and is also distinguishable from any other fluorescent species utilized in the assay.

Illustrative Three-Cell Population Type-Specific ABVIC Assay

In a preferred embodiment, the present invention is a serological assay for determining whether a subject is infected with HSV-1, HSV-2, both, or neither. The assay comprises the steps of dividing a serum sample obtained from a subject into at least three serum subsamples, preadsorbing the serum subsamples to at least three populations of fixed and permeabilized test cells, incubating the preadsorbed serum subsamples with a mixture of at least three populations of test cells in a suspension, incubating the serum subsamples with a detection antibody, and analyzing the cell-serum subsample admixture with a flow cytometer.

The one or more herpes simplex viruses are preferably selected from the group comprising herpes simplex virus type 1 (HSV-1) and herpes simplex virus type 2 (HSV-2).

The at least three populations of fixed and permeabilized cells are preferably Vero cells, wherein a first population is uninfected, a second population is infected with HSV-1, and a third population is infected with HSV-2.

The at least three populations of test cells in suspension are preferably Vero cells, wherein a first population is uninfected and unlabeled, a second population is infected with HSV-1 and labeled with a low concentration of a first fluorescent molecule, and a third population is infected with HSV-2 and labeled with a high concentration of that first-noted fluorescent molecule. Preferably, the first fluorescent molecule is carboxyfluorescein diacetate, succinimidyl ester (CFSE).

The detection antibody is preferably an anti-IgG antibody, and anti-human IgG where the subject whose serum is assayed is human. The detection antibody is also preferably labeled with a second fluorescent molecule. The second fluorescent molecule should have a fluorescence emission spectrum that does not overlap with the fluorescence emission spectrum of the first fluorescent molecule used to label each population of test cells. A suitable second fluorescent molecule is allophycocyanin (APC), but many other fluorophores described herein are suitable as well.

The flow cytometry device can be any device capable of quantitatively measuring the fluorescence associated with individual antigen-containing test matrices of an appropriate diameter for the instrument, about 1 to about 20 microns. Examples of such appropriately sized antigen-containing test matrices include, but are not limited to, (1) live uninfected Vero cells, (2) fixed and permeabilized uninfected Vero cells, (3) live HSV-1-infected Vero cells, (4) fixed and permeabilized HSV-1-infected Vero cells, (5) live HSV-2-infected Vero cells, or (6) fixed and permeabilized HSV-2-infected Vero cells. Preferably, the cell sorting device is a flow cytometer, but a fluorescence-activated cell sorter (FACS) can be used for the same purpose although generally such instruments are about 20-times more expensive and are thus reserved for the act of "sorting cells" (hence the name of the instrument) based on fluorescent intensity, as opposed to the more rudimentary task of measuring the fluorescent intensity associated with cells, which is generally performed with a flow cytometer.

Antibody-Binding to Virus-Infected Cells (ABVIC): A More Sensitive Method than ELISA to Measure Pan-HSV-2 IgG Antibodies-Two Cell Studies As discussed herein, the presence of serum IgG antibodies that bind all HSV-2 antigens (pan-HSV-2 IgG) can be visualized by red fluorescent immunostaining of HSV-2 plaques in Vero cell monolayers (FIGS. 1A and 1B). Naïve serum lacks HSV-2 antibodies, and thus red immunofluorescent staining of HSV-2$^+$ cells does not occur (FIG. 1A). Serum from HSV-2-immune animals contains HSV-2 antibodies that yield red immunofluorescent staining in this test (FIG. 1B). The novel ABVIC assay relies on this same principle, but this assay is far more quantitative because antibody testing is performed on populations of single cells in suspension that can be analyzed for red immunofluorescent staining in a flow cytometer (y-axis in FIGS. 1C and 1D).

This assay is referred to as the "ABVIC assay" because it measures antibody-binding to virus-infected cells. HSV-2-infected (HSV-2$^+$) cells are labeled with a green fluorophore, CFSE, whereas uninfected (UI) cells lack this label, which permits the two cell populations to be differentiated in a flow cytometer (x-axis of FIGS. 1C and 1D).

Test cell suspensions were incubated with serum from naïve mice or immunized mice, and the amount of IgG antibody bound to UI or HSV-2$^+$ cells was detected via an anti-mouse IgG secondary antibody bearing a red fluorescent label (allophycocyanin; APC) (y-axis of FIGS. 1C and 1D). When cells were incubated with naïve mouse serum, similar levels of IgG antibody bound HSV-2$^+$ and UI cells. Specifically, the mean fluorescent intensity (MFI) was about 7,000 in both populations (FIG. 1C). In contrast, when cell suspensions were incubated with serum from a HSV-2 vaccinated mouse, antibody binding to HSV-2$^+$ cells (MFI about 600,000) was about 20 times higher than UI cells (FIG. 1D).

Figure 9:
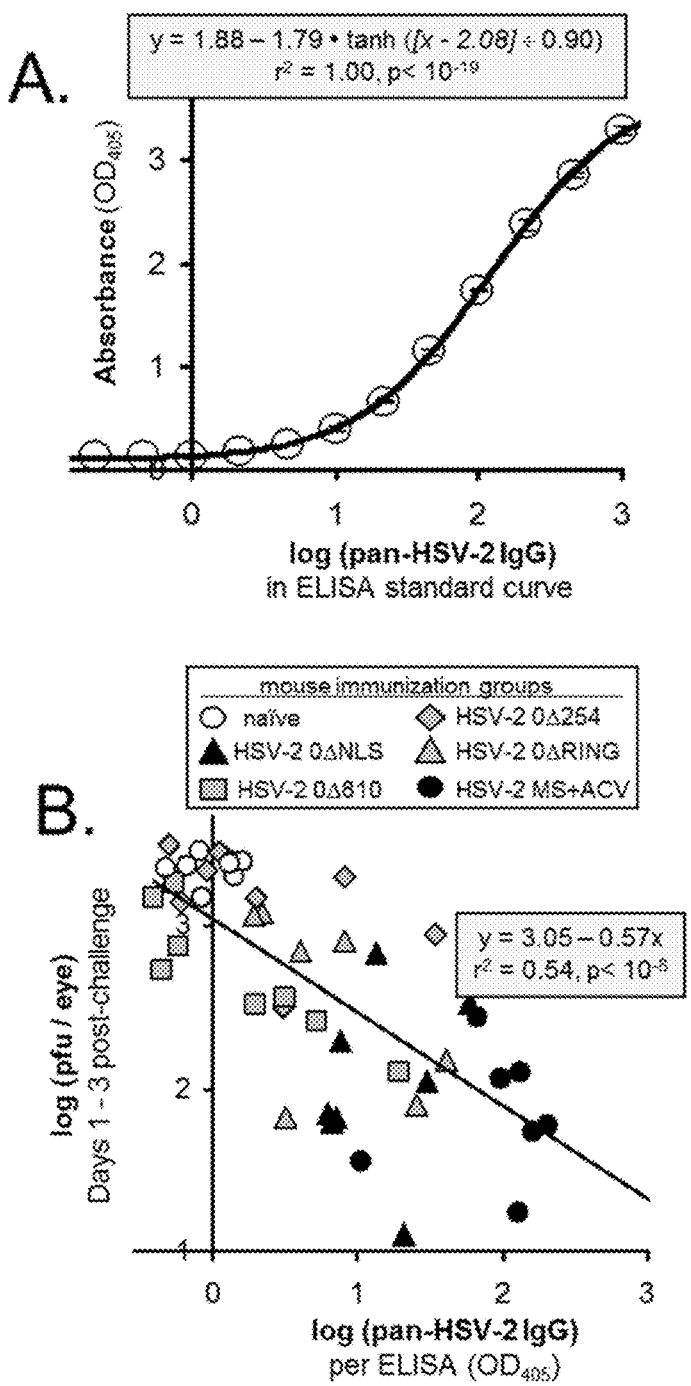
FIG. 9 shows antibody-capture ELISA versus flow cytometry measurement of pan-HSV-2 IgG levels in mouse serum.
Figure 9:
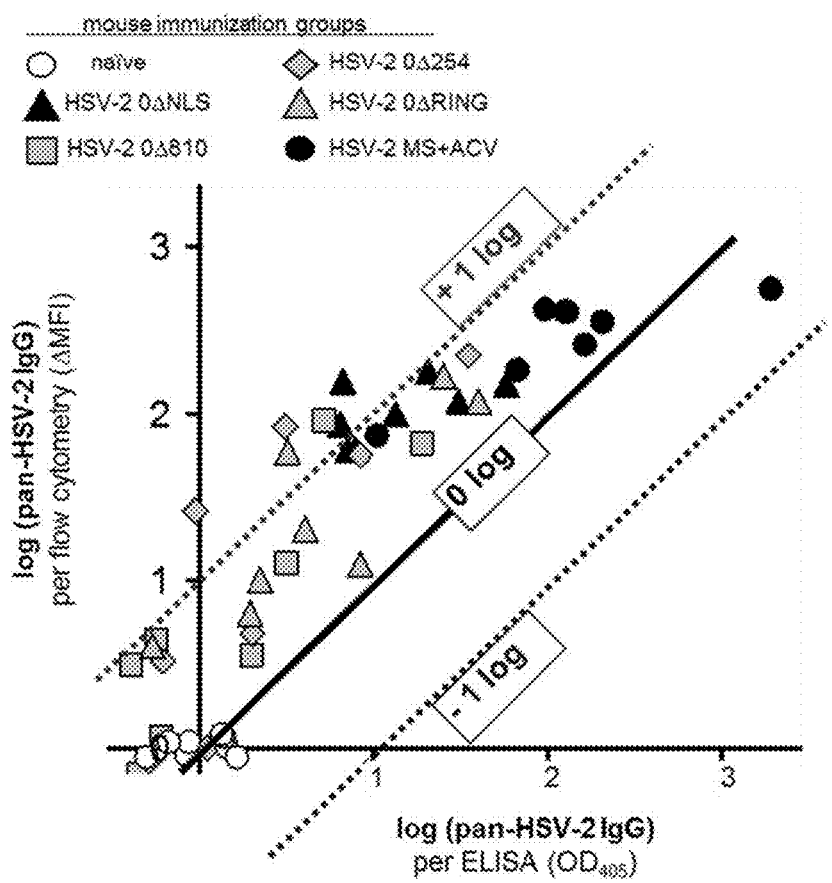

Antibody-capture ELISA and ABVIC were compared in a side-by-side manner to compare their relative sensitivity (FIG. 9C). ELISA estimates of log (pan-HSV-2 IgG) in n=48 mice were plotted on the x-axis, whereas ABVIC-estimates from the same mice were plotted on the y-axis (FIG. 9C). If the two methods were equally sensitive, then the datum points should scatter around a '0 log' line-of-equivalence. However, 35 of 36 positive samples fell above the line-of-equivalence and the ABVIC assay yielded 5±1-fold higher estimates of pan-HSV-2 IgG antibody abundance than ELISA (FIG. 9C). This is one of several analyses that supported a conclusion that the ABVIC assay was more sensitive and precise than ELISA-based estimates of HSV-specific antibody abundance.

Two Cell Population ABVIC Assay Demonstrates that Two of Four "HSV-2 Indeterminate" Patients are Seronegative Clinical serum samples have been obtained periodically from Terri Warren (Westover Heights Clinic) since 2011. Quorum IRB (Seattle, Wash.) and SIU School of Medicine's Springfield Committee for Research on Human Subjects both concluded the research was "exempt," as only de-identified sera were evaluated. An analysis of human sera using the ABVIC assay is described, as follows.

Figure 10:
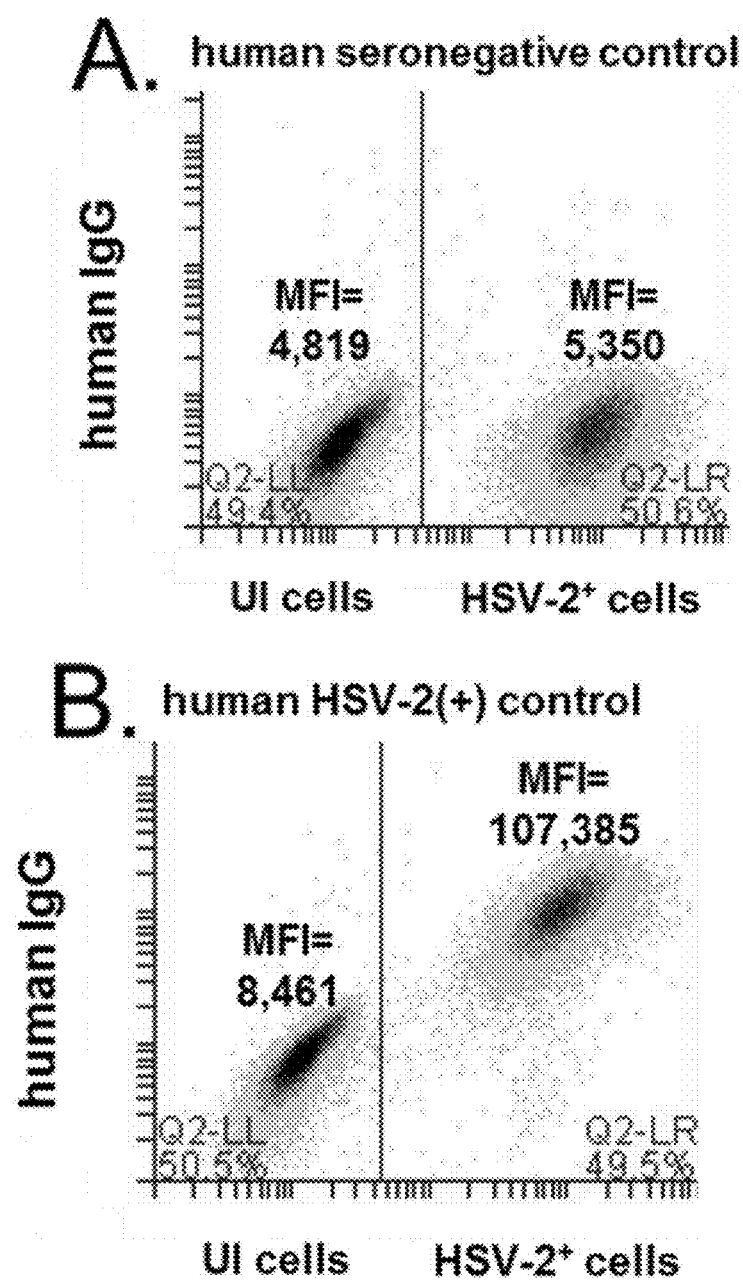
FIG. 10 shows that the two cell population ABVIC assay establishes that two of four "HSV-2 indeterminate" patients are seronegative. Human IgG antibody-binding to a fixed suspension of CFSE-labeled HSV-2+ cells and uninfected (UI) Vero cells stained with serum antibodies.
Figure 10:
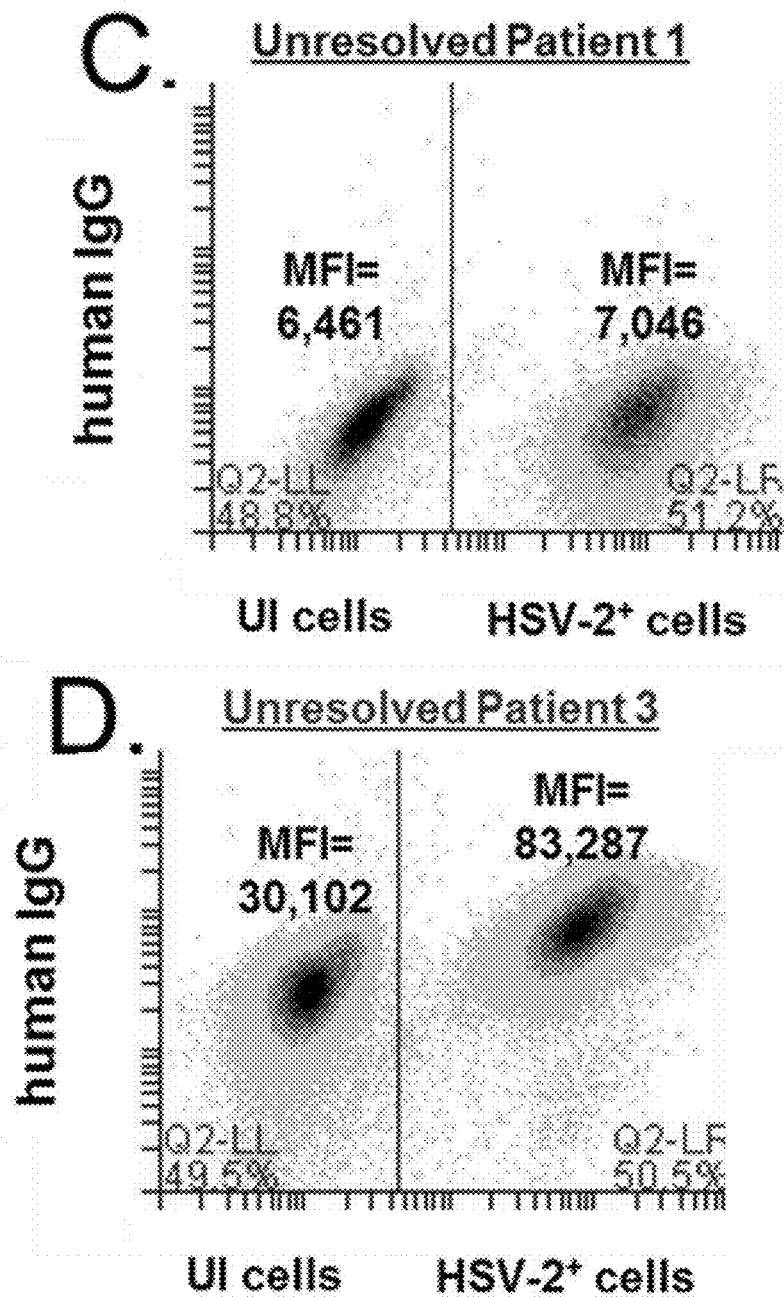

Sera from n=3 seronegative individuals defined the background level of antibody-binding to HSV-2⁺ cells and UI cells (FIG. 10A). Sera from n=3 HSV-2 genital herpes patients possessed antibodies that bound HSV-2⁺ cells to 10- to 20-fold higher levels than UI cells (FIG. 10B). Sera from four patients whose serological status was indeterminate by HerpeSelect® ELISA and HSV Western Blot were tested in the ABVIC assay. The ABVIC assay demonstrated that indeterminate serum samples 1 and 2 were actually HSV-2 seronegative (FIG. 10C). Sera from indeterminate serum samples 3 and 4 yielded a HSV positive result (FIG. 10D), but the ABVIC assay failed to discriminate whether these individuals were infected with HSV-1, HSV-2, or both viruses. Further steps were taken to overcome this limitation, and develop a HSV type-specific ABVIC assay.

The Illustrative Three Cell Population Type-Specific ABVIC Assay

Two modifications were employed to convert the two cell population ABVIC assay into the three cell population HSV type-specific ABVIC assay. These changes were: 1) serum preadsorption to UI cells, HSV-1⁺ cells, or HSV-2⁺ cells (FIG. 11); and 2) testing preadsorbed serum against three populations of UI cells vs HSV-1⁺-infected cells vs HSV-2⁺-infected cells (FIG. 12).

Figure 11:
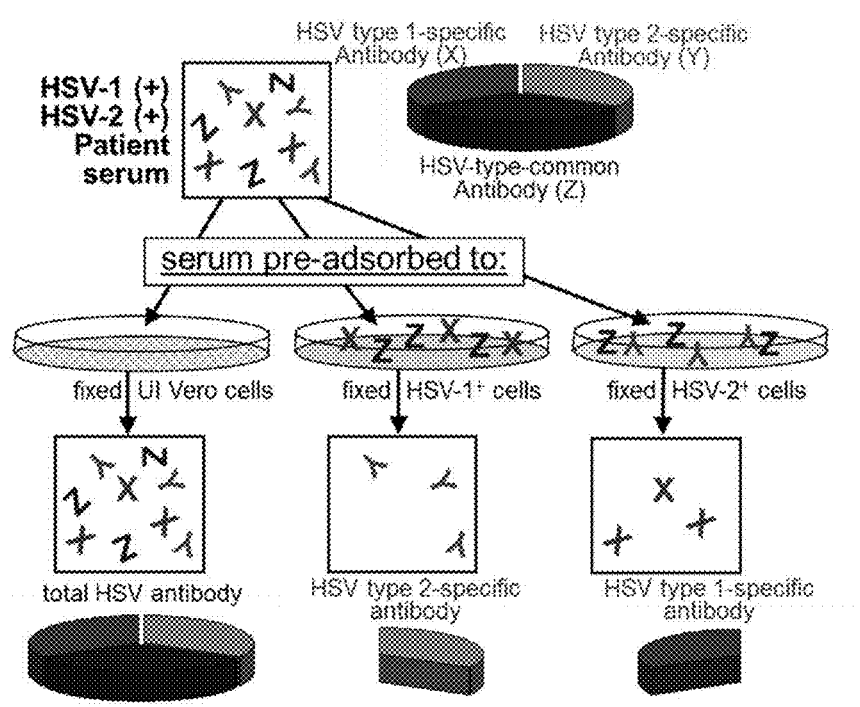
FIG. 11 shows that serum preadsorption yields enriched populations of HSV type-specific antibody. A seropositive patient's serum may contain three populations of antibody that are HSV type common, HSV-1 specific, or HSV-2 specific. Serum preadsorption to UI Vero cells does not remove HSV antibodies (left column). Preadsorption to HSV-1+ cells enriches for HSV-2-specific antibodies (center column). Preadsorption to HSV-2+ cells enriches for HSV-1-specific antibodies (right column).

Regarding serum preadsorption, patients infected with HSV-1 and/or HSV-2 possess up to three populations of HSV antibodies: 1) type-common antibodies that bind HSV-1 and HSV-2 antigen proteins (Z's in FIG. 11); 2) HSV-1-specific antibodies that only bind HSV-1 antigen proteins (X's in FIG. 11); and 3) HSV-2-specific antibodies that only bind HSV-2 antigen proteins (Y's in FIG. 11).

An enriched population of HSV-2-specific antibodies can be obtained by preadsorbing serum from a HSV-infected subject (human or other animal) to fixed HSV-1⁺ cells, which depletes type-common and HSV-1-specific antibodies (center column, FIG. 11), and enhances the relative concentration of any anti-HSV-2 antibodies that are present. Likewise, an enriched population of HSV-1-specific antibodies can be obtained by preadsorbing serum to HSV-2⁺ cells (right column, FIG. 11). Preadsorption to UI cells (left column, FIG. 11) controls for any effects of the procedure.

Figure 12:
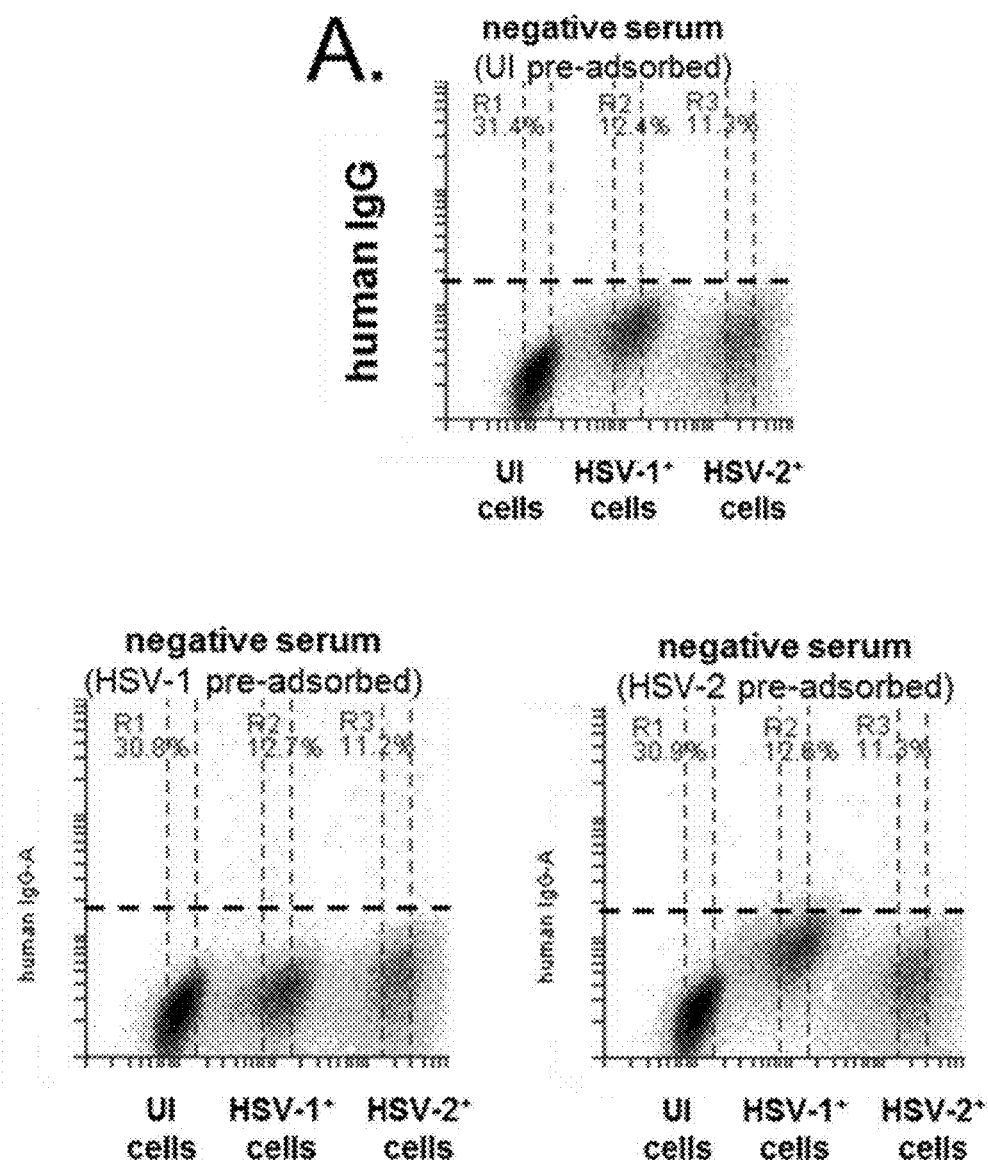
FIG. 12 shows that the three cell population type-specific ABVIC assay demonstrates that two of four "HSV-2 indeterminate" patients are HSV-2 seronegative, but HSV-1 seropositive. Human IgG antibody-binding to CFSE-labeled uninfected (UI) versus HSV-1+ versus HSV-2+ cells is shown.
Figure 12:
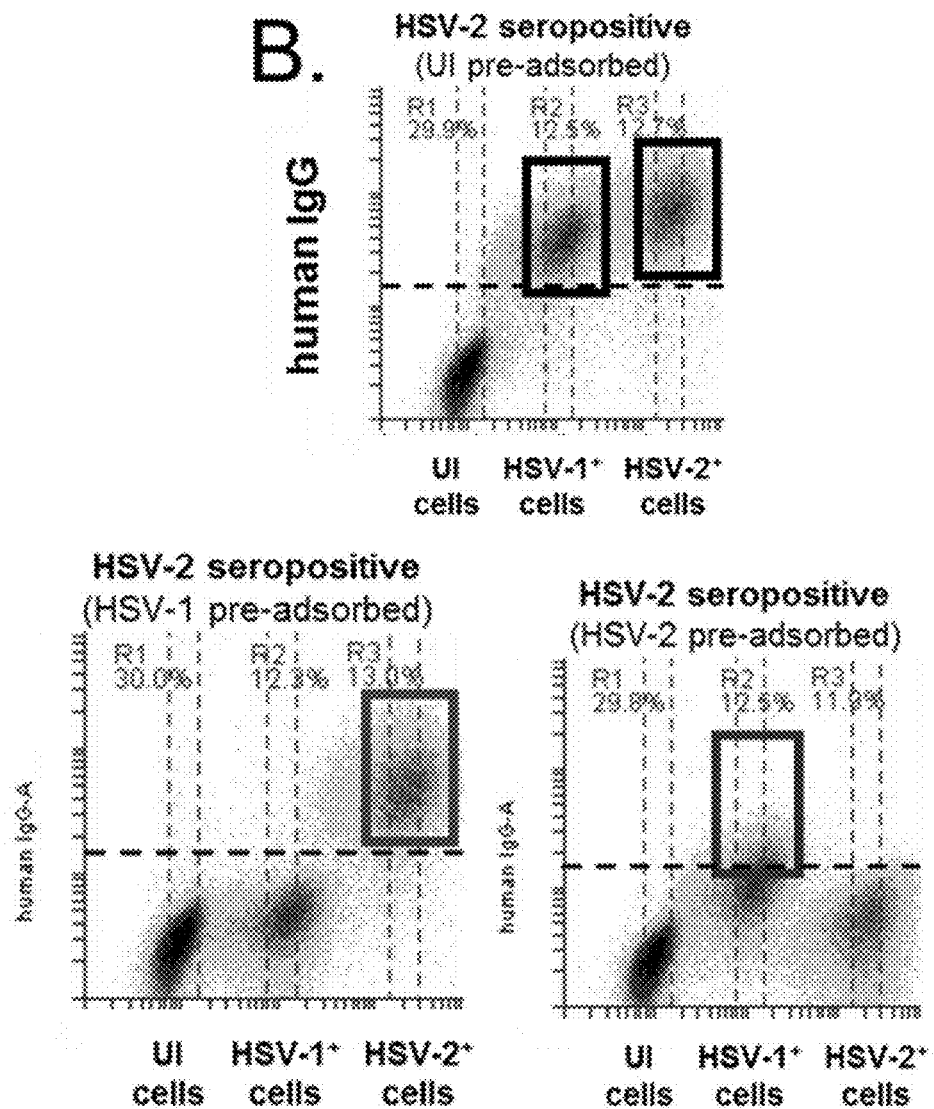
Figure 12:
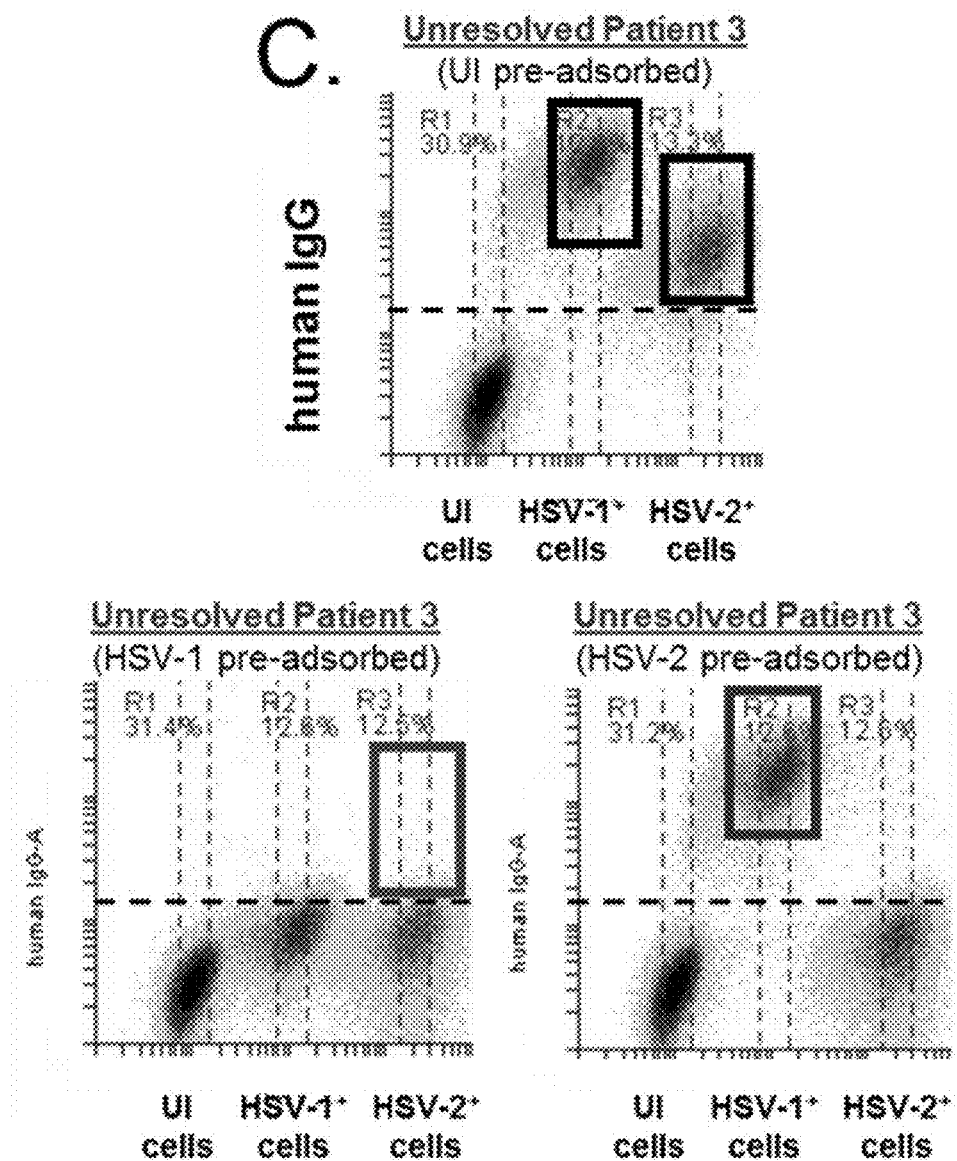

Regarding the three cell population assay, an optimized CFSE-labeling protocol was developed that yields populations of UI cells (no CFSE), HSV-1⁺ cells (CFSE$^{lo}$), and HSV-2⁺ cells (CFSE$^{hi}$), which can be resolved in a flow cytometer (FIG. 12). UI cells appear on the left of a two-color plot, whereas HSV-1⁺ cells and HSV-2⁺ cells are labeled with low (lo) and high (hi) CFSE levels, and thus appear as center and right populations, respectively (FIG. 12A). By combining serum preadsorption and this three cell population assay, a HSV type-specific antibody-binding to virus-infected cells (ABVIC) assay has been achieved. Representative results are presented, as follows.

A seronegative serum sample was incubated with test cells after preadsorption to each cell population. Following preadsorption to UI cells, negligible antibody binding to cells was noted (left graph, FIG. 12A). Similar results were obtained after preadsorption to HSV-1⁺ cells or HSV-2⁺ cells (center and right graphs, FIG. 12A).

Serum of a known HSV-2 seropositive individual was incubated with test cells after preadsorption to each cell population. Following preadsorption to UI cells, HSV-specific antibodies bound HSV-1⁺ and HSV-2⁺ cells to 10- and 15-fold higher levels than UI cells, respectively (left graph, FIG. 12B). When serum was preadsorbed to HSV-1⁺ cells, high levels of HSV-2-specific antibody remained and bound HSV-2⁺ cells (box, center graph, FIG. 12B); hence, this patient was HSV-2-seropositive. When this patient's serum was preadsorbed to HSV-2⁺ cells, antibody-binding to HSV-1⁺ cells was ablated (box, right graph, FIG. 12B); hence, this patient was HSV-1 seronegative. These results were consistent with earlier Western Blot testing.

Indeterminate serum sample 3 discussed previously was incubated with test cells after separate subsample preadsorptions to each of the three cell populations. Following preadsorption to UI cells, HSV-specific antibodies bound HSV-1⁺ and HSV-2⁺ cells to 100- and 20-fold higher levels than UI cells, respectively (left graph, FIG. 12C). When the serum was preadsorbed to HSV-1⁺ cells, antibody-binding to HSV-2⁺ cells was ablated (box, center graph, FIG. 12C); hence, this patient was HSV-2-seronegative. When the serum was preadsorbed to HSV-2⁺ cells, high levels of HSV-1-specific antibody remained (box, right graph, FIG. 12C); hence, this patient was HSV-1-seropositive.

These findings indicated that the patient who provided indeterminate serum sample 3 was infected with HSV-1, but not HSV-2 at the time the serum sample was obtained. Indeterminate serum sample 4 yielded equivalent results (not shown). Therefore, the three cell population type-specific ABVIC assay demonstrated that indeterminate serum samples 3 and 4 were both HSV-2 seronegative and HSV-1 seropositive.

HSV-2 indeterminate serum samples 1, 2, 3, and 4 represent four patients who could have been spared a great deal of anxiety and suffering if a better HSV serological assay were available to properly inform them that they were not infected with HSV-2 and thus could not transmit HSV-2 genital herpes to any sexual contacts.

Illustrative Three Cell Population Type-Specific ABVIC Assay is More Sensitive than HerpeSelect®

The HerpeSelect® assay (Quest Diagnostics, Inc.) is an antibody-capture ELISA that tests for the presence of antibodies specific for glycoprotein G of HSV-1 (gG-1) or HSV-2 (gG-2) [Whittington et al., 2001]. These are two of the most divergent HSV proteins known [Sanchez-Martinez et al., 1991; Roizman et al., 1984]. Patients infected with HSV-1 can mount an antibody response against 30 HSV-1 proteins including gG-1, and likewise HSV-2 infection can drive an antibody response against 30 HSV-2 proteins including gG-2 [Norrild et al., 1981; Gilman et al., 1981] (FIGS. 13A and 13C).

Figure 13:
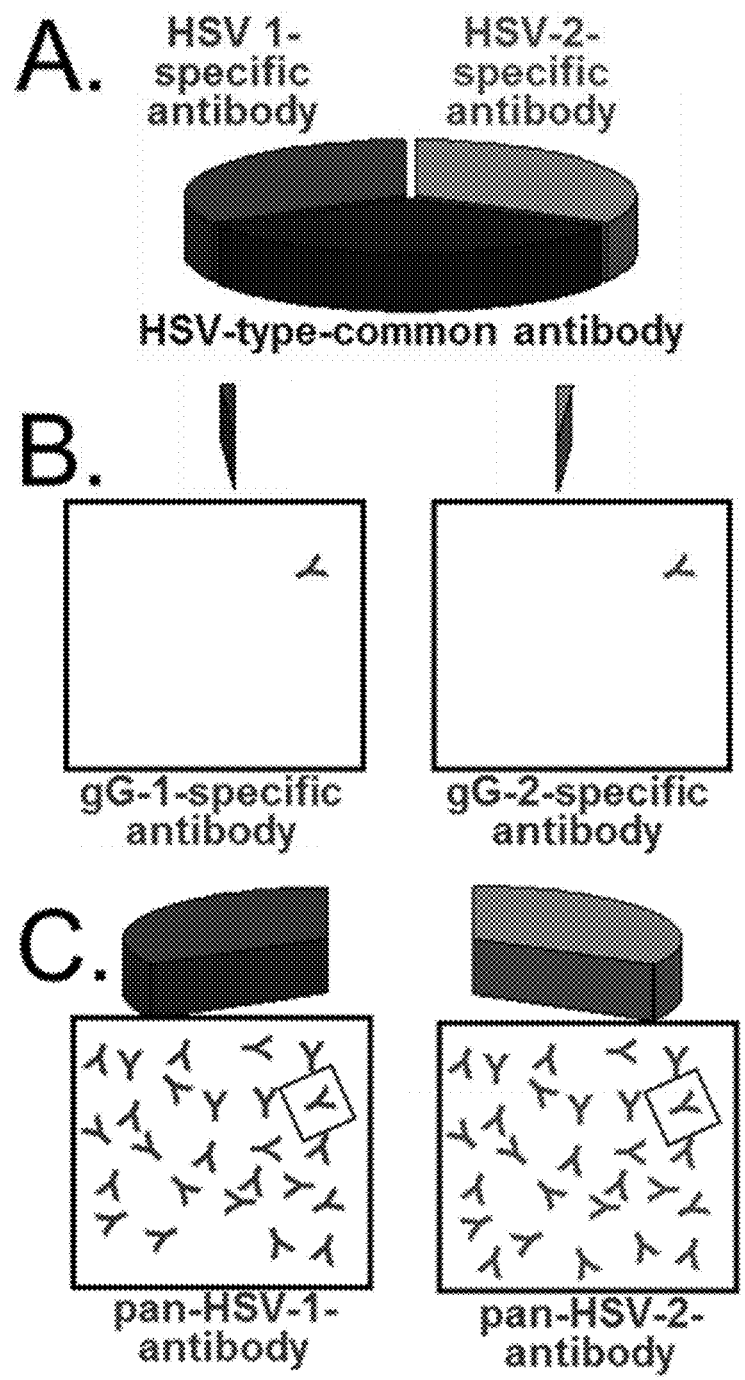
FIG. 13 shows that gG-specific ELISAs only test for 3-10% of all HSV-2 specific antibodies.

A critical weakness of the HSV-2 HerpeSelect® assay is that it only tests for antibodies against gG-2, which represent 3-10% of an infected person's total repertoire of HSV-2-specific antibodies (FIG. 13B vs 13C). The HerpeSelect® test does not consider the other 90-97% of HSV-2-specific antibodies directed against gB, gC, gE, gH, and 25 other major antigens of HSV-2. A test with the potential to detect all HSV-2 specific antibodies should offer a 10- to 30-fold increase in sensitivity relative to the HerpeSelect® test (FIG. 13B vs 13C). The illustrative three cell population type-specific ABVIC assay achieves this goal by using cell antigens from fixed and permeabilized HSV-2⁺ cells as a test reagent, which contain all about 75 HSV-2 proteins, and thus can bind all HSV-2-specific antibodies.

The Illustrative Three Cell Population Type-Specific ABVIC Assay is More Sensitive than Western Blot The illustrative three cell population type-specific ABVIC assay is unique amongst HSV serological assays in that it tests for pan-HSV-type-specific antibodies, is internally controlled, and is based on thousands of replicate measurements. In the ABVIC assay, the level of a patient's IgG antibodies that bind thousands of HSV-2⁺ cells versus UI cells is measured, and these quantities are compared to those produced by a panel of control seronegative and HSV-2 seropositive sera.

Thus, the cutoff between "seronegative" and "seropositive" can be set to any level of statistical significance deemed appropriate (e.g., the probability that the patient who provided indeterminate serum sample 3 was HSV-2-seropositive was less than 1 in a million; FIG. 12C; p<0.000001). In contrast, Western blot analysis is a qualitative assay and does not lend itself to assigning statistically determined probabilities to a diagnosis of "HSV-2 seronegative."

Figure 23:
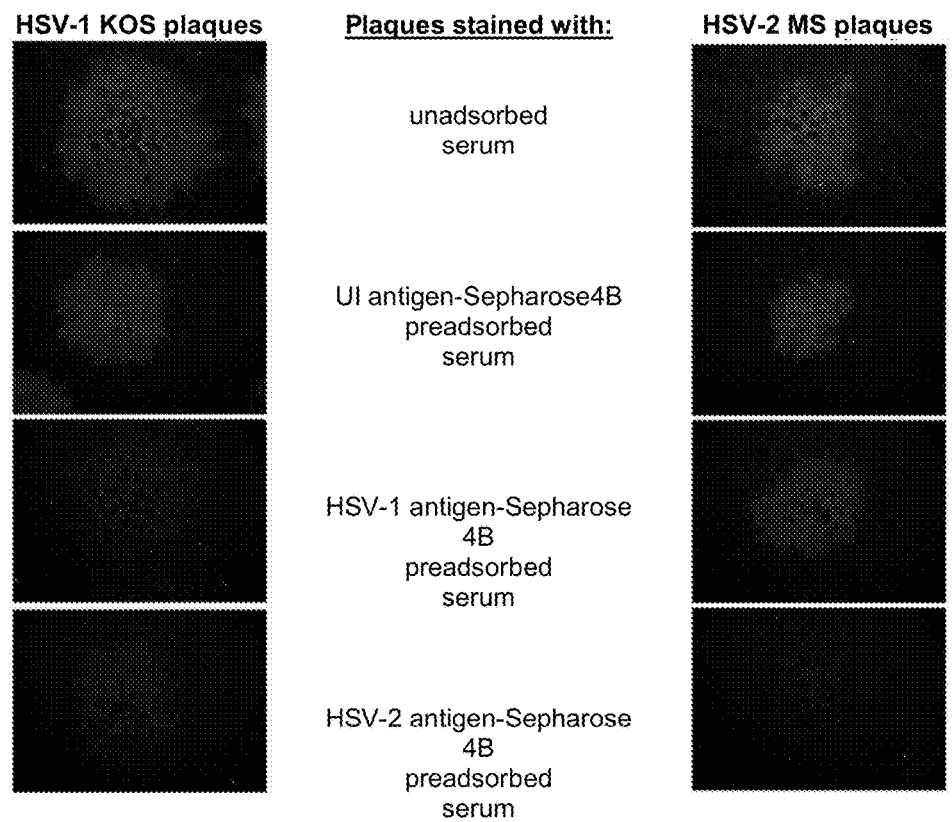
FIG. 23, in a series of eight portions in two vertical columns of four immunofluorescent micrographs each. Vero cell monolayers were infected with one or the other of HSV-1 and HSV-2 to form plaques, or nothing (uninfected-UI). Prior to addition of patient serum to these test cells (i.e., HSV-1 or HSV-2 plaques in a monolayer of fixed and permeabilized cells), patient serum was preadsorbed to a matrix of cyanogen bromide (CNBr)-activated Sepharose® 4B coated with the antigens of uninfected (UI) Vero cells, HSV-1+ Vero cells, or HSV-2+ Vero cells to provide a basis for preadsorption and removal of HSV-type-common antibodies and HSV-1- or HSV-2-specific antibodies. The uppermost micrographs show that diluted, but non-preadsorbed serum contained a mixture of HSV-type common antibodies and HSV-2-specific antibodies that collectively bound both (i) HSV-1 plaques shown on the left and (ii) HSV-2 plaques shown on the right. Hence, unadsorbed patient serum was insufficient to determine if this individual was infected with HSV-1 and/or HSV-2. The same dilution of the serum followed by preadsorption to an uninfected (UI) antigen matrix, still contained a mixture of HSV-type common antibodies and HSV-2-specific antibodies that collectively bound both (i) HSV-1 plaques shown on the left and (ii) HSV-2 plaques shown on the right of the second row down. Hence, UI cell antigen-preadsorbed patient serum was insufficient to determine if this individual was infected with HSV-1 and/or HSV-2. After preadsorption of the diluted serum with a matrix of HSV-1-infected (HSV-1$^+$) antigens, HSV-type common antibodies were depleted out but HSV-2-specific antibodies remained. Hence, the enriched population of HSV-2-specific antibodies only poorly bound to HSV-1 plaques on the left (almost completely dark), but bound strongly to HSV-2 plaques shown in the brighter micrograph on the right of the third row down. Hence, HSV-1 cell antigen-preadsorbed patient serum was sufficient to determine that this individual was HSV-2 seropositive, which is prognostic for an underlying HSV-2 infection. Diluted serum was preadsorbed to a matrix of HSV-2-infected (HSV-2$^+$) antigens, HSV-type common antibodies and HSV-2-specific antibodies were depleted out. Were this patient infected with HSV-1, and thus were this patient HSV-1 seropositive, HSV-1-specific antibodies would remain. However, the bottom-most two micrographs show that the HSV-2-preadsorbed serum did not possess antibodies that bound HSV-1 plaques on the left to a level higher than HSV-2 plaques shown on the right (both remaining dark). Hence, this HSV-2 antigen-preadsorbed patient serum was sufficient to determine that this individual was HSV-1 seronegative. Antibody binding was detected using Alexa Fluor® (Life Technologies) 594-conjugated goat-anti-human IgG antibody, which produces the red color captured in the photomicrographs.
Figure 24:
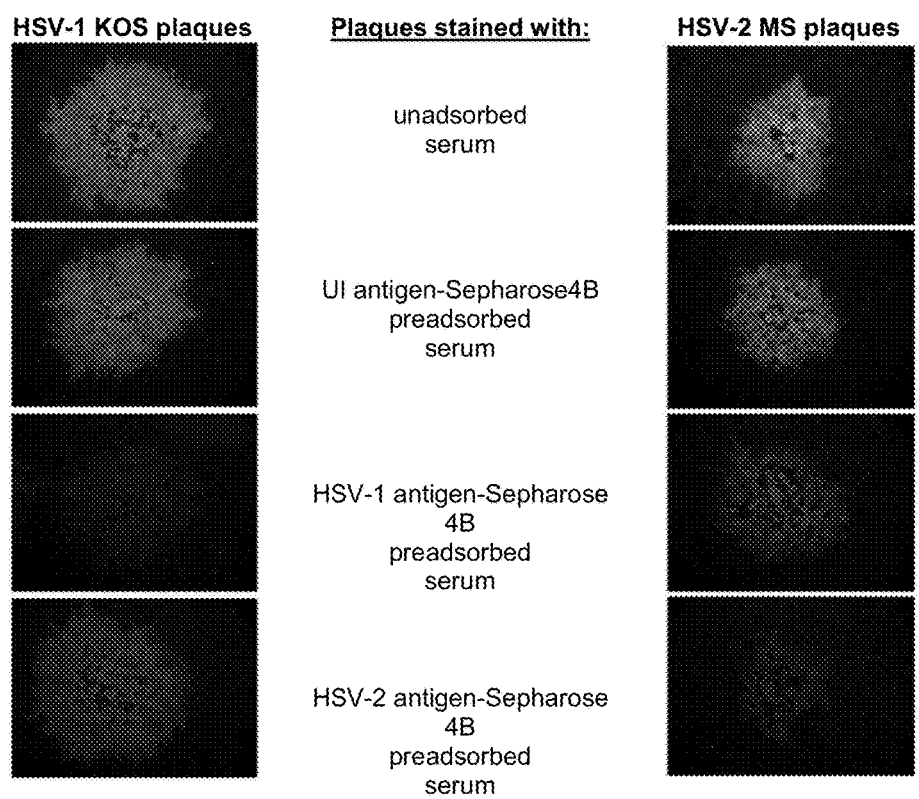
FIG. 24 shows a similar array of fluorescent micrographs to those of FIG. 23 obtained using the same reagents, but different serum from a patient known to be both HSV-1 seropositive and HSV-2 seropositive. Using the same rationale offered in FIG. 23, the data obtained with the patient's HSV-1 antigen-preadsorbed serum show that the individual is HSV-2 seropositive (third row down, left micrograph is dark, whereas the right micrograph is bright). Likewise, the data obtained with the patient's HSV-2 antigen-preadsorbed serum show that the individual is HSV-1 seropositive (fourth row down, left micrograph is bright, whereas the right micrograph is dark).

Detection of Human Antibody Binding to (i) Uninfected, (ii) HSV-1$^+$, and/or (iii) HSV-2$^+$ Test Cells A. Immunofluorescent microscopy. It is possible to determine if a patient serum sample contains HSV-2-specific antibody by comparing its ability to bind uninfected cells versus virus-infected cells in the context of monolayers of Vero cells that are infected with a small amount of HSV-1 or HSV-2 virus that is allowed to form small foci of infection (a.k.a. "plaques"). In this embodiment of the type-specific ABVIC test, human antibody binding to virus-infected cells could be visualized with a fluorescent microscope (FIGS. 23-24). To convert such an experimental system to a test for "HSV-2-specific antibody" could be achieved with three elements such as:

1. HSV-1 plaques in a monolayer of mammalian cells;
2. HSV-2 plaques in a monolayer of mammalian cells;
3. uninfected (UI) antigen-, HSV-1$^+$ antigen-, and HSV-2$^+$ antigen-matrices.

A specific example of such a test is illustrated in FIG. 23, where the mammalian cell line used is the African Green Monkey kidney cell line known as "Vero cells," and the matrix that was used to immobilize antigens for preadsorption was cyanogen-bromide (CNBr)-activated Sepharose 4B (GE Healthcare Life Sciences). It should be noted that both HSV-1 and HSV-2 plaques (i.e., areas of virus-infected cells) are surrounded by "black areas" of uninfected (UI) cells where the virus had not yet reached at the time of cell harvest and fixation.

Hence, the difference in "mean red fluorescent intensity" (ΔMFI) is what one's eye notes that tells one this individual must possess "HSV-specific antibody," and this is precisely the same quantity that is being compared in the more quantitative, flow-cytometry-based variation of the type-specific ABVIC test. In the images of FIG. 23, antibody-binding was visualized with "AlexaFluor594-conjugated goat-anti-human IgG" antibody, which produces the red color captured in the photomicrographs.

Specifically, serum of a patient who was known to be HSV-2-seropositive was used to validate that these three sets of reagents were useful to test for the presence of HSV-2-specific antibodies. Starting at the top of the panels shown in FIG. 23A, when this patient's serum sample was diluted 1:2,000 and was not preadsorbed to any antigen matrix, it contained a mixture of HSV-type common antibodies and HSV-2-specific antibodies that collectively bound both (i) HSV-1 plaques shown-on the left and (ii) HSV-2 plaques shown on the right. Hence, unadsorbed patient serum was insufficient to determine if this individual was infected with HSV-1 and/or HSV-2.

When this patient's serum sample was diluted 1:2,000 and was preadsorbed to a matrix of uninfected (UI) cell antigens, it still contained a mixture of HSV-type common antibodies and HSV-2-specific antibodies that collectively bound both (i) HSV-1 plaques shown on the left and (ii) HSV-2 plaques shown on the right. Hence, UI cell antigen-preadsorbed patient serum was insufficient to determine if this individual was infected with HSV-1 and/or HSV-2 (FIG. 23B).

When this patient's serum sample was diluted 1:2,000 and was preadsorbed to a matrix of HSV-1-infected (HSV-1$^+$) cell antigens, HSV-type common antibodies were depleted out but HSV-2-specific antibodies remained. Hence, the enriched population of HSV-2-specific antibodies only poorly bound to HSV-1 plaques on the left, but bound strongly to HSV-2 plaques shown on the right. The HSV-1 cell antigen-preadsorbed patient serum was sufficient to determine that this individual was HSV-2 seropositive, which is prognostic for an underlying HSV-2 infection (FIG. 23C).

Finally, when this patient's serum sample was diluted 1:2,000 and was preadsorbed to a matrix of HSV-2-infected (HSV-2$^+$) cell antigen, HSV-type common antibodies and HSV-2-specific antibodies were depleted out. If this patient were infected with HSV-1, and thus were HSV-1 seropositive, HSV-1-specific antibodies present would remain. However, what is observed in the final panel is that the HSV-2-preadsorbed serum did not possess antibodies that bound HSV-1 plaques on the left to a level higher than HSV-2 plaques shown on the right. Hence, this HSV-2 cell antigen-preadsorbed patient serum was sufficient to determine that this individual was HSV-1 seronegative (FIG. 23D).

In FIG. 24, the results of an identical test are shown using a patient's serum who was known to be both HSV-1- and HSV-2-seropositive. Using the same rationale offered in FIG. 23, the data obtained with the patient's HSV-1 cell antigen-preadsorbed serum show that the individual is HSV-2 seropositive (FIG. 24C). Likewise, the data obtained with the patient's HSV-2 cell antigen-preadsorbed serum show that the individual is HSV-1 seropositive (FIG. 24D).

B. Flow cytometry. One can determine if a patient serum sample contains HSV-2-specific antibodies by comparing its ability to bind uninfected cells versus virus-infected cells in the context of suspensions of uninfected, HSV-1-infected, and HSV-2-infected mammalian cells. In this embodiment of the type-specific ABVIC assay, human antibody binding to virus-infected cells can be quantitatively measured using a flow cytometer (FIGS. 15-18).

Such an experimental system can be used to measure "HSV-2-specific antibody" using the three elements of:
1. HSV-1-infected mammalian cells;
2. HSV-2-infected mammalian cells; and
3. Three populations of uninfected (UI) test cell antigen-, HSV-1-infected test cell antigen-, and HSV-2-infected test cell antigen-matrices.

A specific example of such a test is illustrated in FIGS. 15-18, where the mammalian cell line used was Vero cells, and the antigen matrix that was used were formaldehyde- and methanol-fixed and permeabilized suspensions of Vero cells that were uninfected, HSV-1-infected, or HSV-2-infected.

In this particular embodiment of the ABVIC assay, a patient's antibody binding to the test cell suspension containing fixed and permeabilized UI cells, HSV-1$^+$ cells, and HSV-2$^+$ cells was measured using "allophycocyanin (APC)-conjugated goat-anti-human IgG" antibody, which produces a far-red color that is measured in the FL4 channel of a flow cytometer (y-axes in each sub-panel in FIGS. 15-18). Specifically, in each panel the comparison shown is the amount of human antibody bound to uninfected (UI) cells, which serve as a background control, versus antibody binding to HSV-1$^+$ cells or HSV-2$^+$ cells. In this particular embodiment of the type-specific ABVIC assay, the three populations of test cells are being differentiated in the FL1 channel of a flow cytometer by differential labeling with the green fluorophore carboxyfluorescein N-succinimidyl ester (CFSE).

Figure 14:
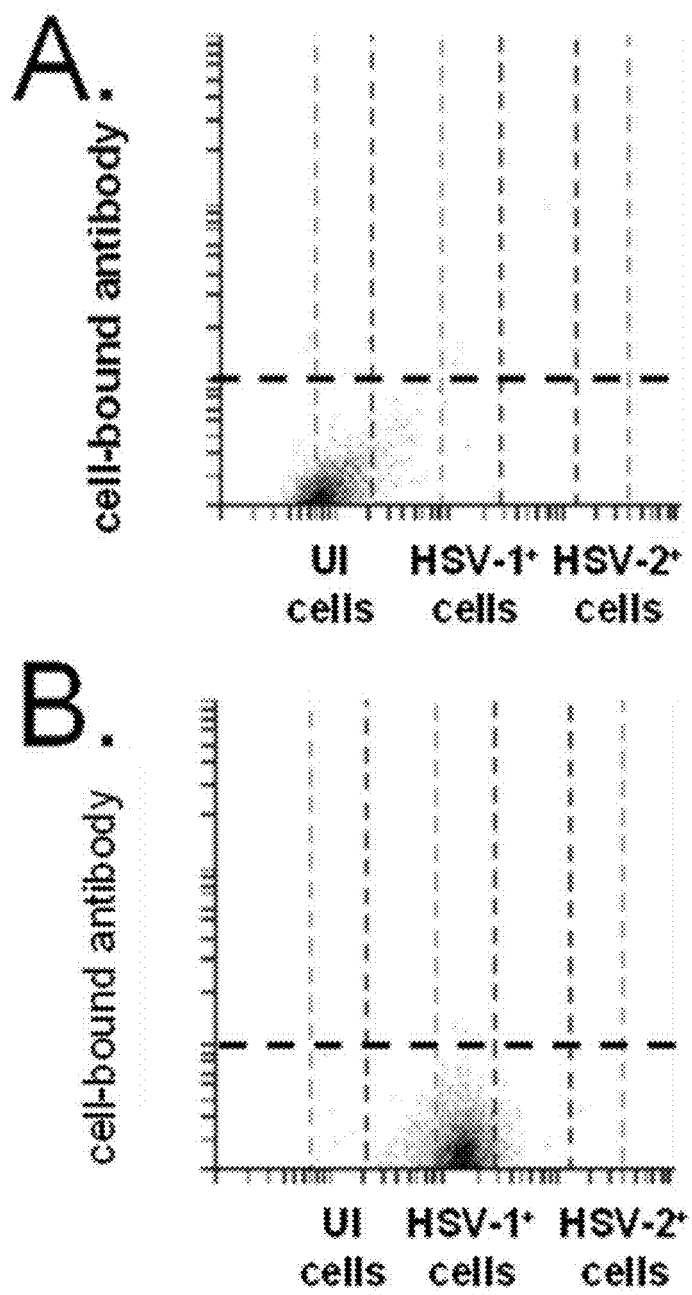
FIG. 14, in three panels as FIG. 14A, FIG. 14B, and FIG. 14C, shows that CFSE (carboxyfluorescein succinimidyl ester) provides a differential label that permits a flow cytometer to easily distinguish a (FIG. 14A) pure population of CFSE(−) uninfected cells from a (FIG. 14B) pure population of CFSE(lo) HSV-1+ cells, from a (FIG. 14C) pure population of CFSE(hi) HSV-2+ cells.
Figure 14:
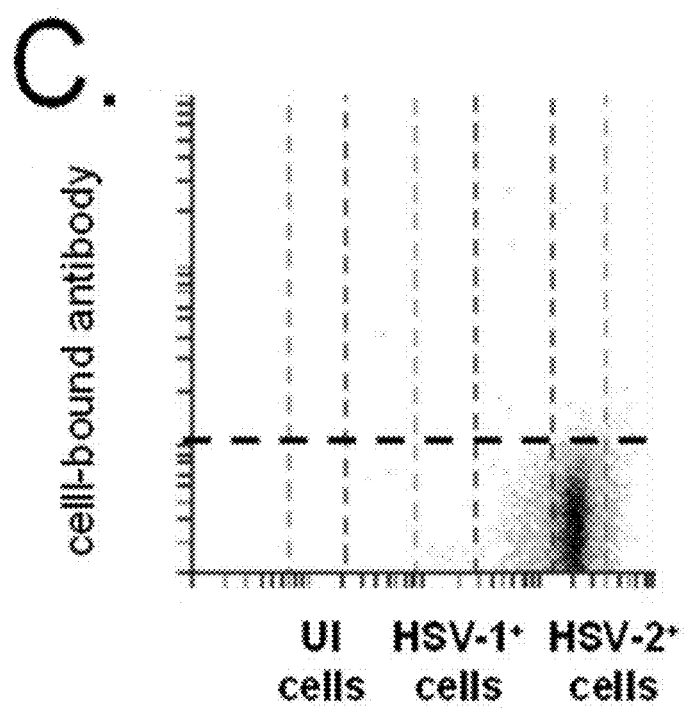

The data in FIG. 14 validates that pure populations of CFSE-differentially labeled UI cells (FIG. 14A), HSV-1⁺ cells (FIG. 14B), or HSV-2⁺ cells (FIG. 14C) are easily differentiated at a level of >99.7% confidence with a flow cytometer. Likewise, data in FIGS. 15-18 directly demonstrate that a mixture of all 3 populations of test cells are still easily differentiated in the FL1 channel, which leaves the FL4 channel (far-red color) free to measure the "difference in mean fluorescent intensity" (ΔMFI) between HSV cells versus UI cells, which directly correlates with the amount of HSV-specific antibody bound to sub-populations of HSV-infected cells versus UI background control cells (Halford, et al., 2013).

Figure 15:
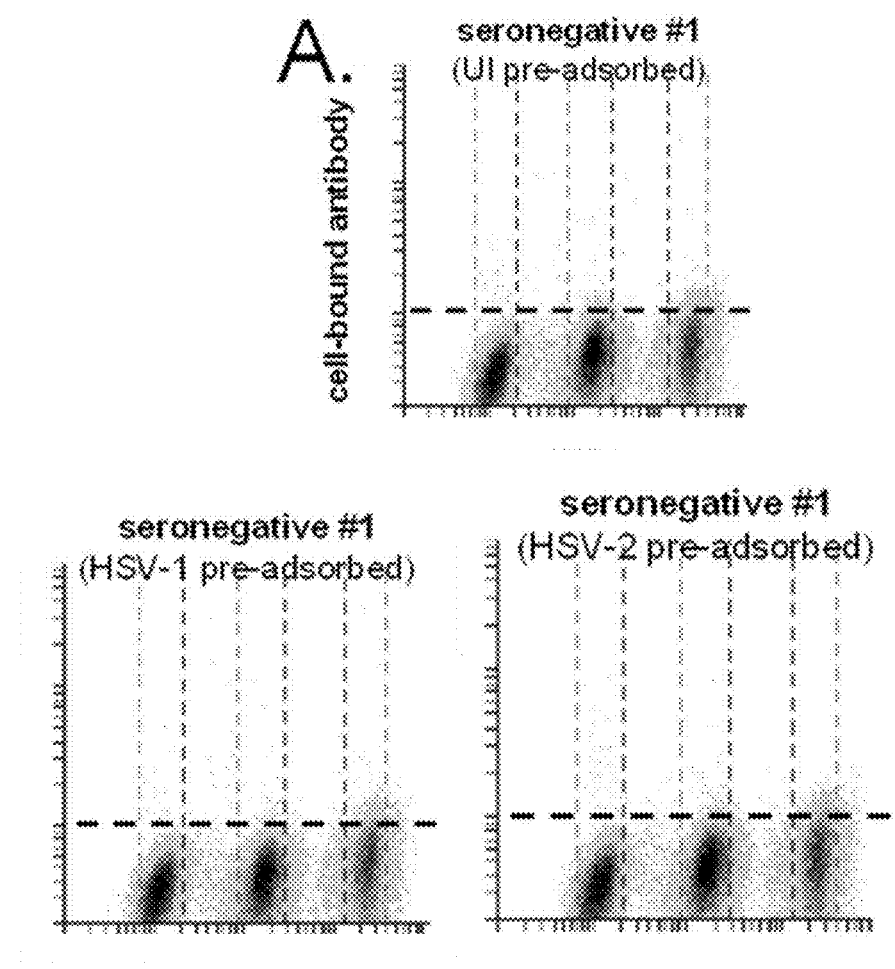
FIG. 15, in four panels as FIG. 15A, FIG. 15B, FIG. 15C, and FIG. 15D, establishes the background levels of antibody that bind the three populations of test cells from four different HSV-seronegative patients. For each patient's serum, there are three flow cytometry plots and these are from serum samples that were: (1) leftmost plot: preadsorbed to an uninfected (UI) antigen matrix, (2) center plot: preadsorbed to a HSV-1-infected (HSV-1+) antigen matrix, and (3) rightmost plot: preadsorbed to a HSV-2-infected (HSV-2+) antigen matrix.
Figure 15:
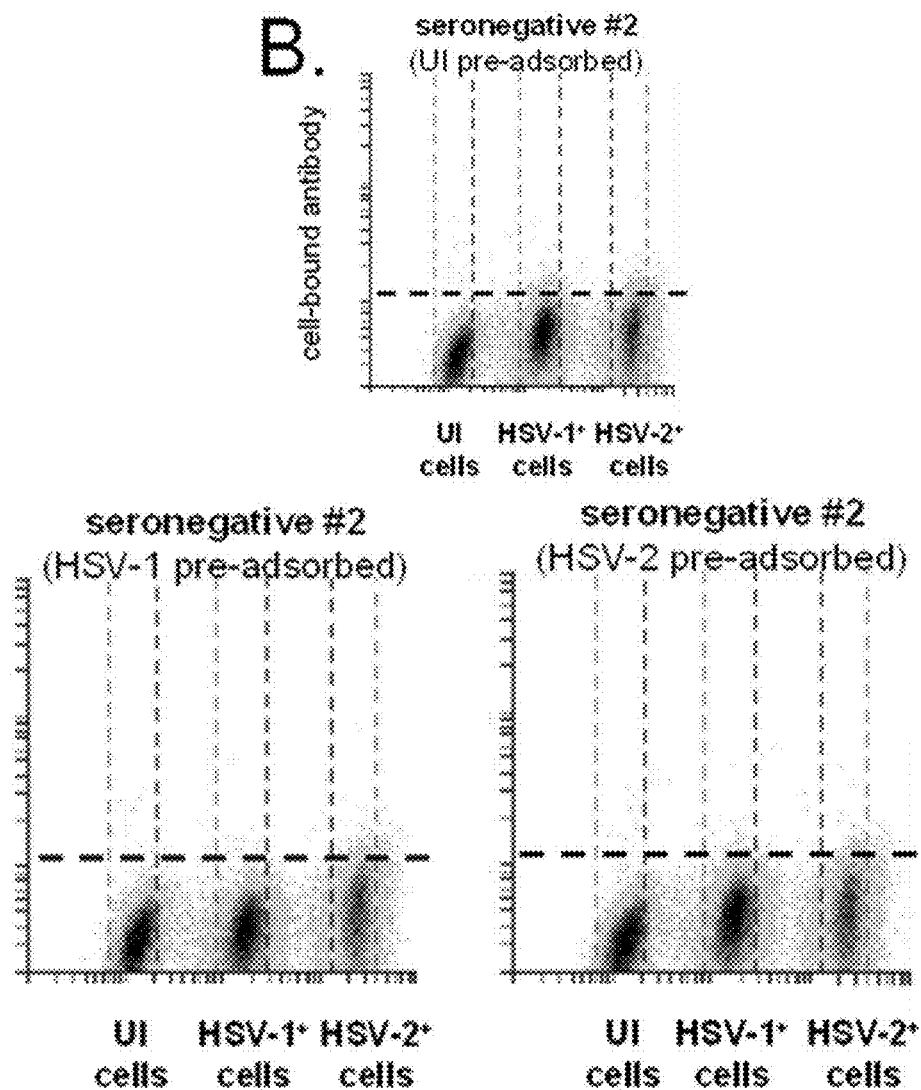
Figure 15:
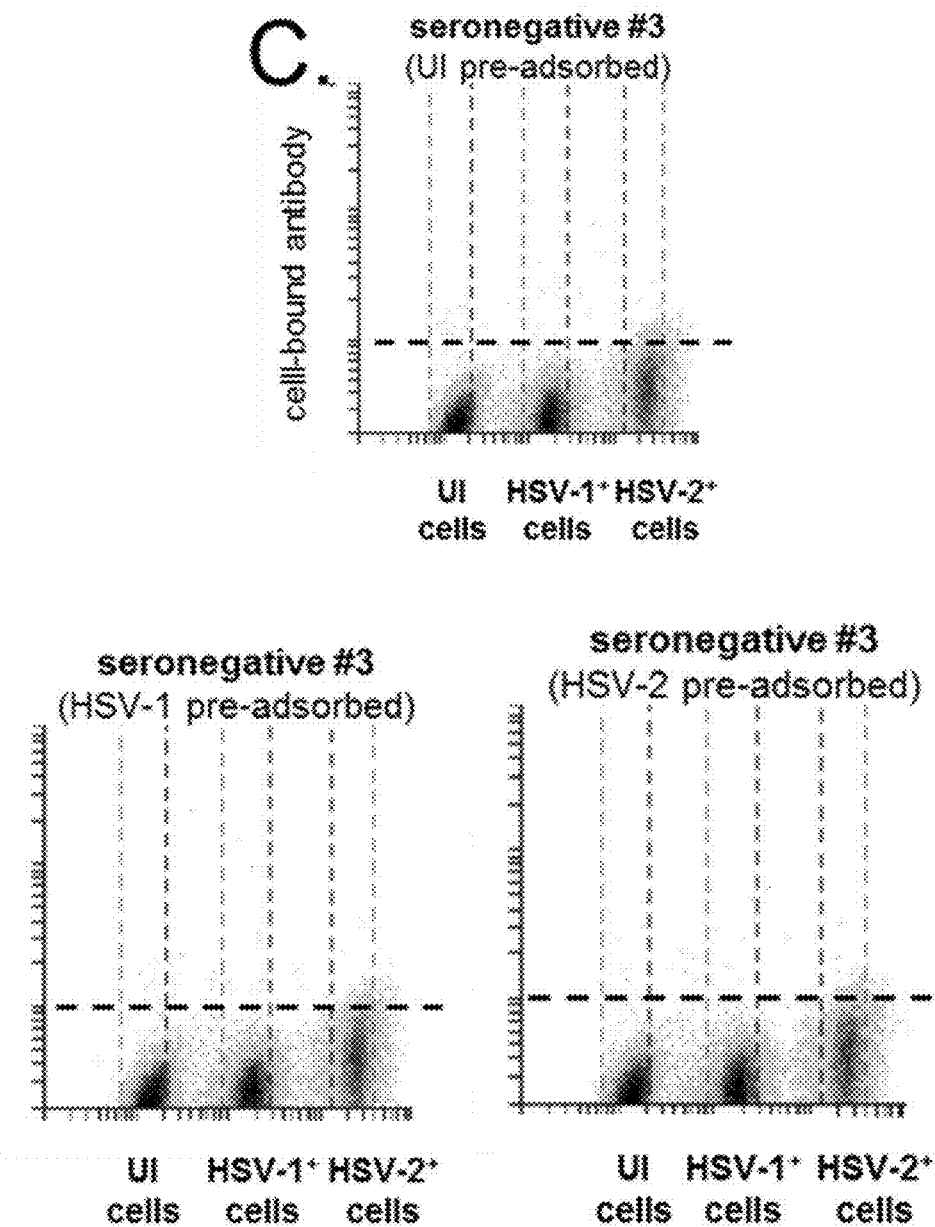

FIG. 15 illustrates the background amount of antibody-binding to HSV-1⁺ cells and HSV-2⁺ cells versus uninfected (UI) background control cells when these populations of test cells are combined with the serum of 4 individuals who are known to be HSV-seronegative (FIGS. 15A-15D).

Figure 21:
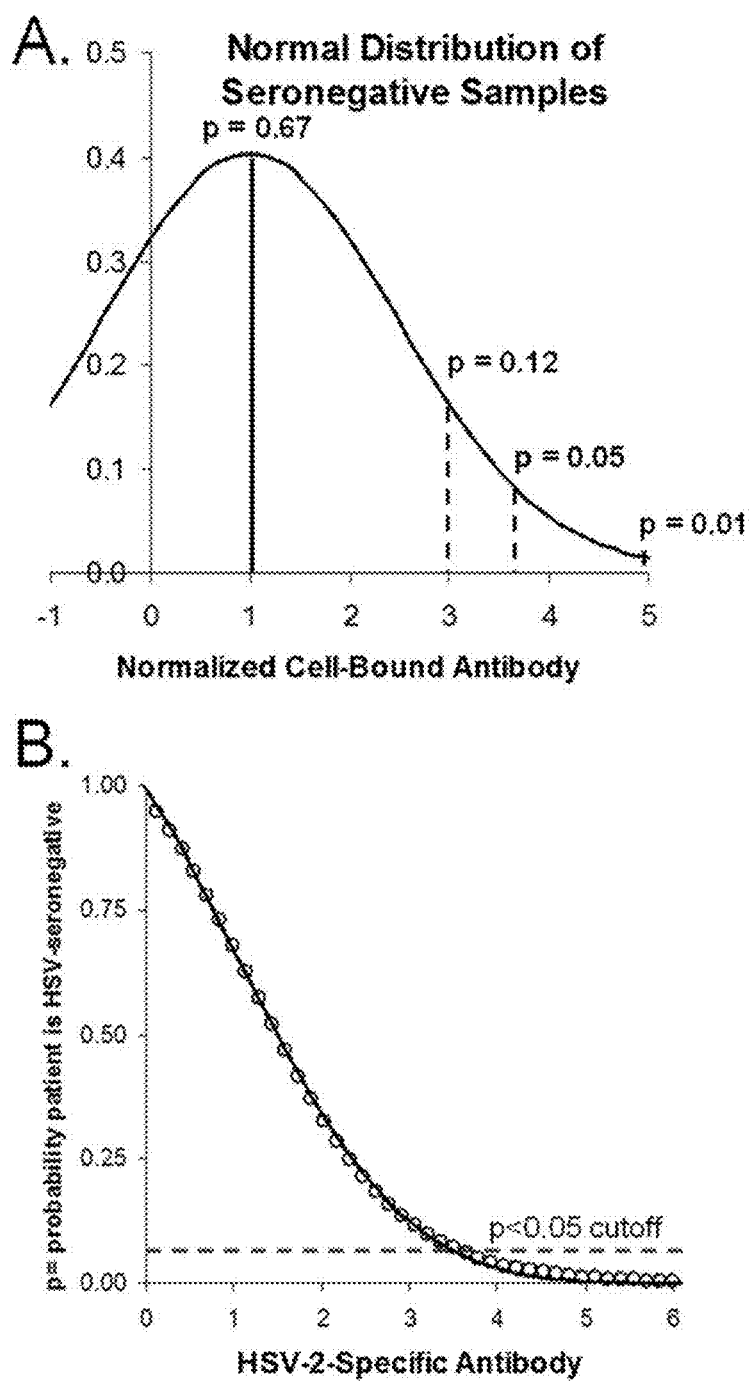
FIG. 21, in two panels as FIG. 21A and FIG. 21B, illustrate how the highly quantitative data provided by an assay of the invention can be statistically analyzed to assign probabilities to a patient's risk for being HSV-2$^+$.
Figure 22:
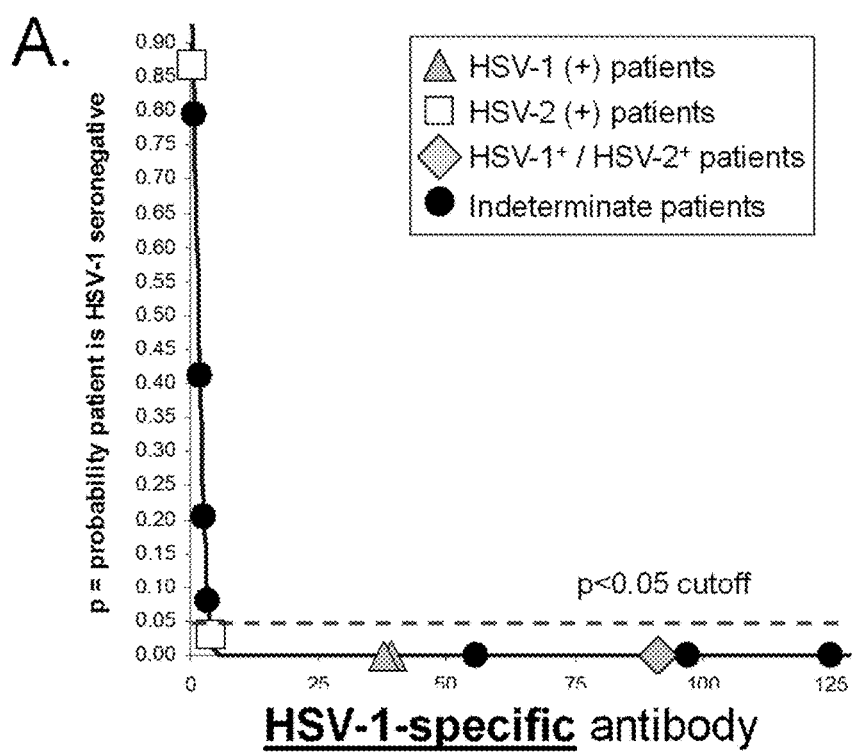
FIG. 22, in two panels as FIG. 22A and FIG. 22B, shows how the "Cell-Bound Antibody" levels of various patient samples can be used in an equation that describes the S-shaped curve in FIG. 21B to back-calculate the probability, p, that this sample is a seronegative sample.
Figure 22:
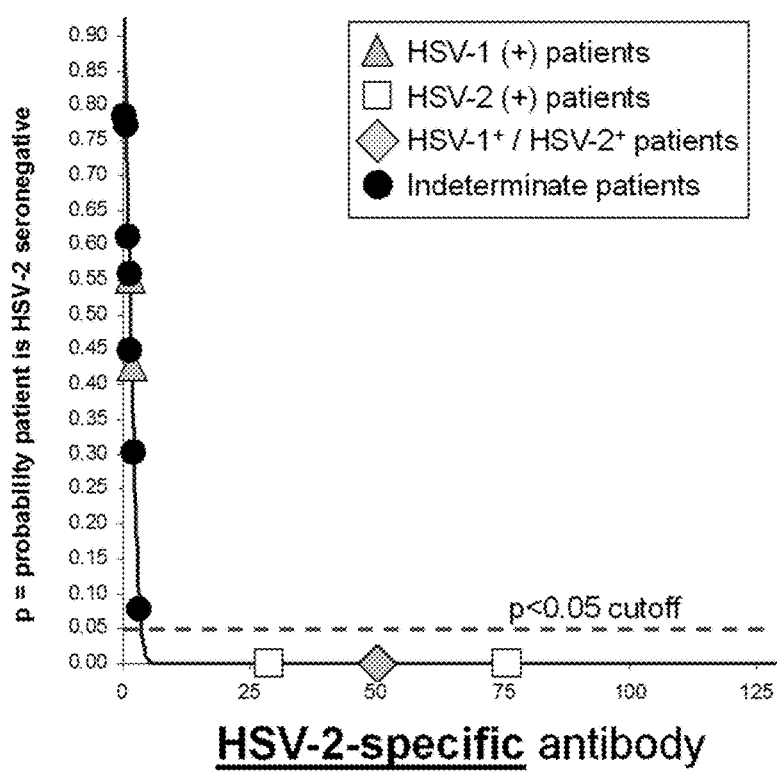

There are three important quantitative features that are unique to the flow cytometry-based embodiment of the type-specific ABVIC test and these are, as follows:

1. Estimates of "HSV-specific antibody" level are based on the difference in mean fluorescent intensity (ΔMFI) in the FL4 channel (y-axis) between n about 20,000 UI cells vs n about 20,000 HSV-1⁺ cells vs n about 20,000 HSV-2⁺ cells, which provides a high degree of confidence in quantitative estimates of HSV-specific antibody abundance in a patient's blood;

2. UI cells provide an internal control that defines the background of the assay, and hence the assay is insensitive to patients whose blood possesses antibodies that cause a higher background signal, which is a major variable that confounds the HerpeSelect® assay and Herpes Western Blots, and likely accounts for at least 50% of "Indeterminate" results that mislead many people to the erroneous conclusion that they are HSV-2 infected/HSV-2 seropositive; and 3. defining the mean and standard deviation of the $\Delta MFI_{HSV-1}$ associated with HSV-1⁺ cells ($MFI_{HSV-1}$-$MFI_{UI}$) and the mean and standard deviation of the $\Delta MFI_{HSV-2}$ associated with HSV-2⁺ cells ($MFI_{HSV-2}$-$MFI_{UI}$) creates the opportunity for statistical analysis of the probability that a given patient is HSV-1-seronegative or HSV-2 seronegative based on where their own $\Delta MFI_{HSV-1}$ or $\Delta MFI_{HSV-2}$ values fall on the normal distribution of $\Delta MFI_{HSV-1}$ or $\Delta MFI_{HSV-2}$ values for control HSV-seronegative samples (FIGS. 21 and 22). Based on these considerations, 1× background is set equal to the average of all $\Delta MFI_{HSV-1}$ and $\Delta MFI_{HSV-2}$ values in the HSV-seronegative controls.

Figure 16:
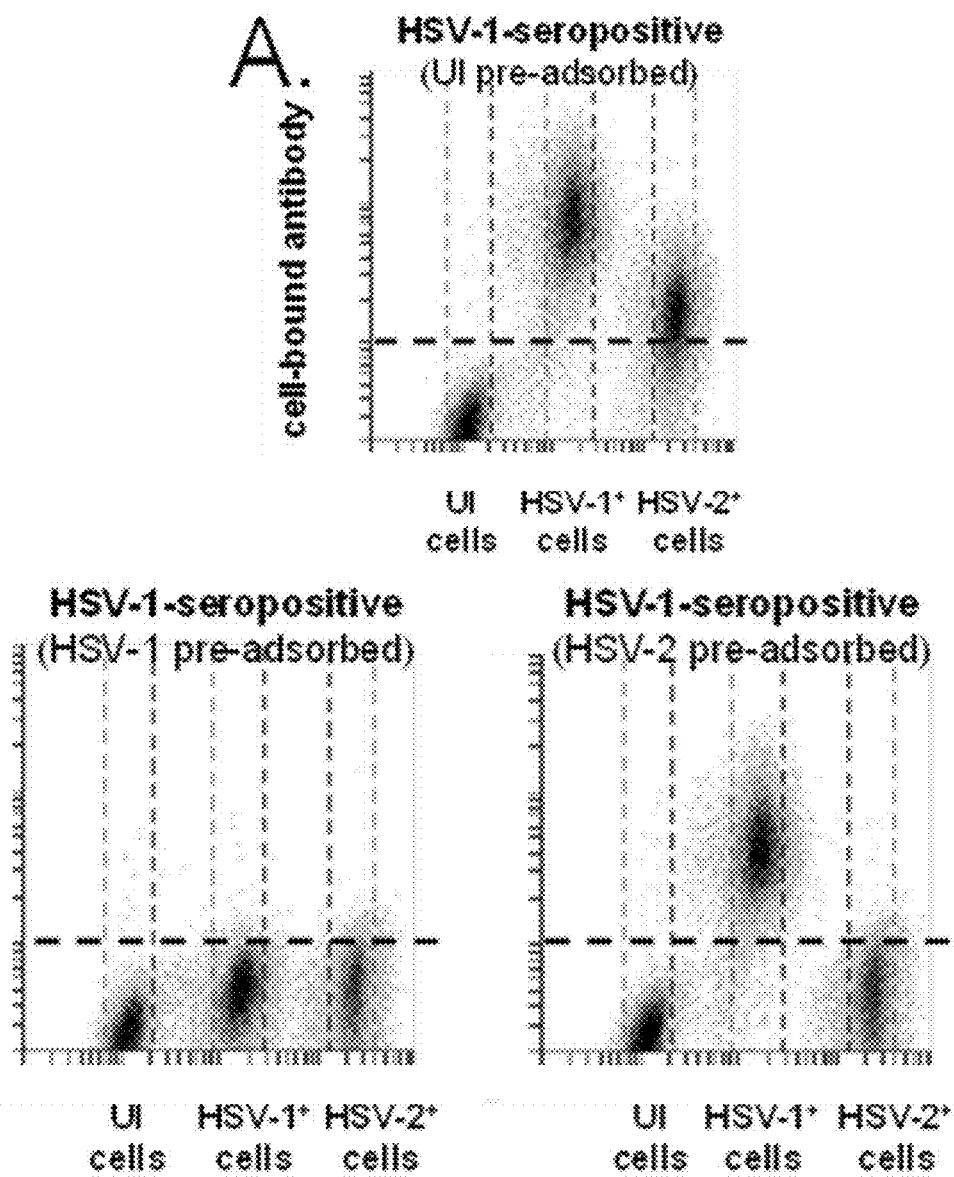
FIG. 16, in four panels as FIG. 16A, FIG. 16B, FIG. 16C, and FIG. 16D, is as described in FIG. 15, except the patient samples shown are a strongly HSV-1+ patient (FIG. 16A), a weakly HSV-2+ patient (FIG. 16B), a strongly HSV-2+ patient (FIG. 16C), and a strongly HSV-1+ and HSV-2+ patient (FIG. 16D).
Figure 16:
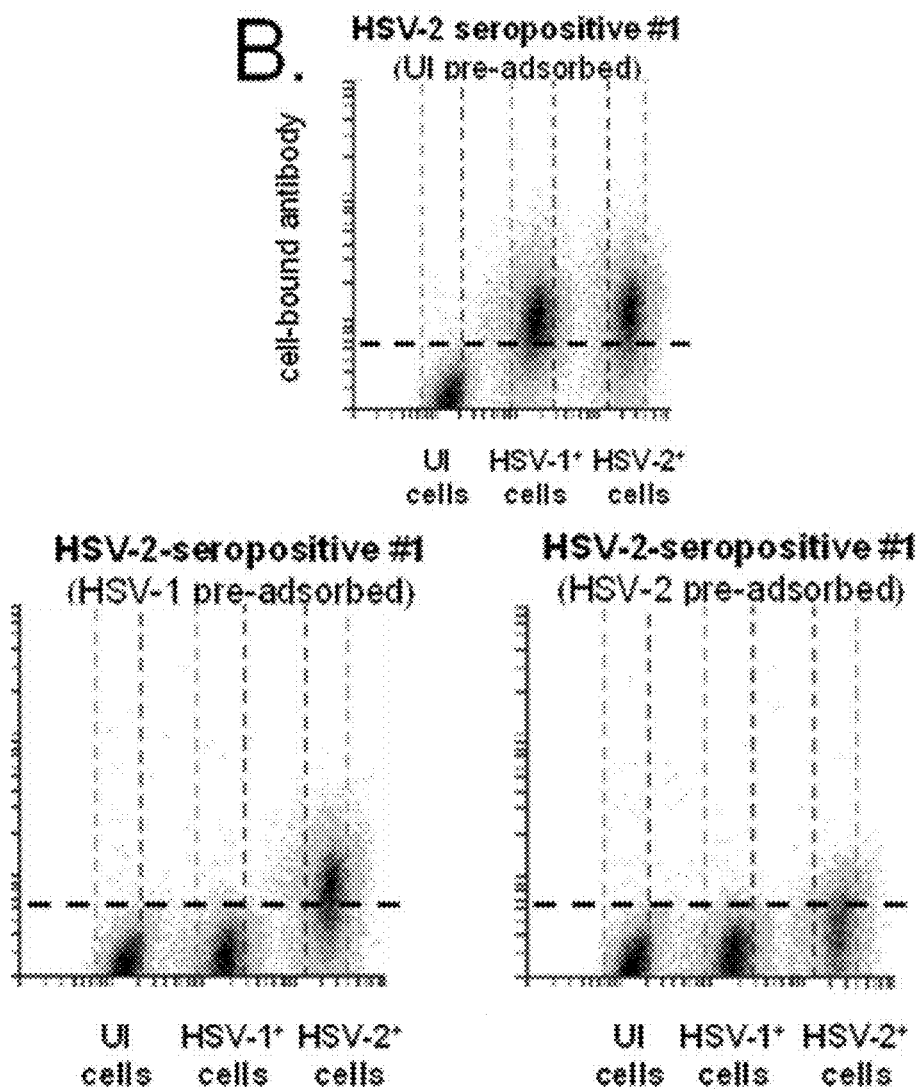
Figure 16:
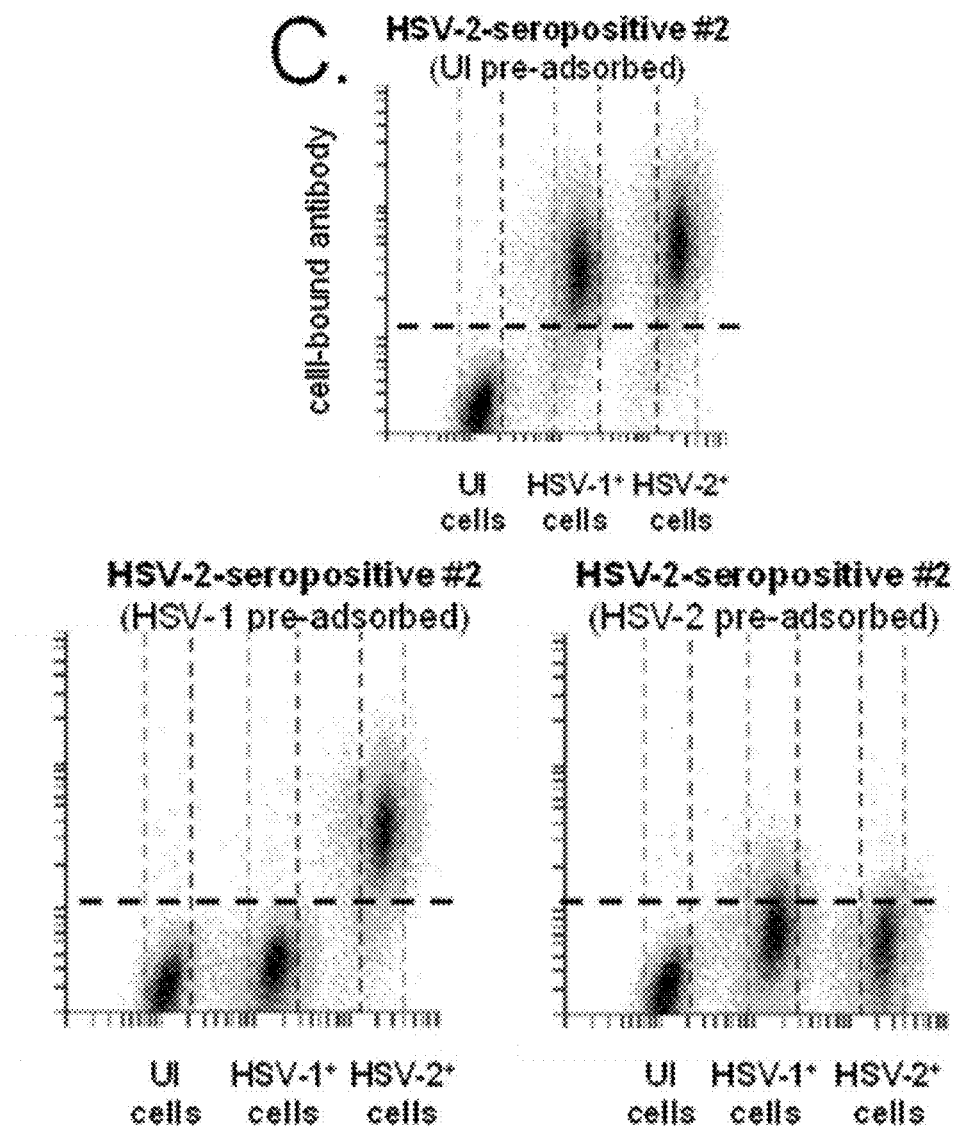
Figure 16:
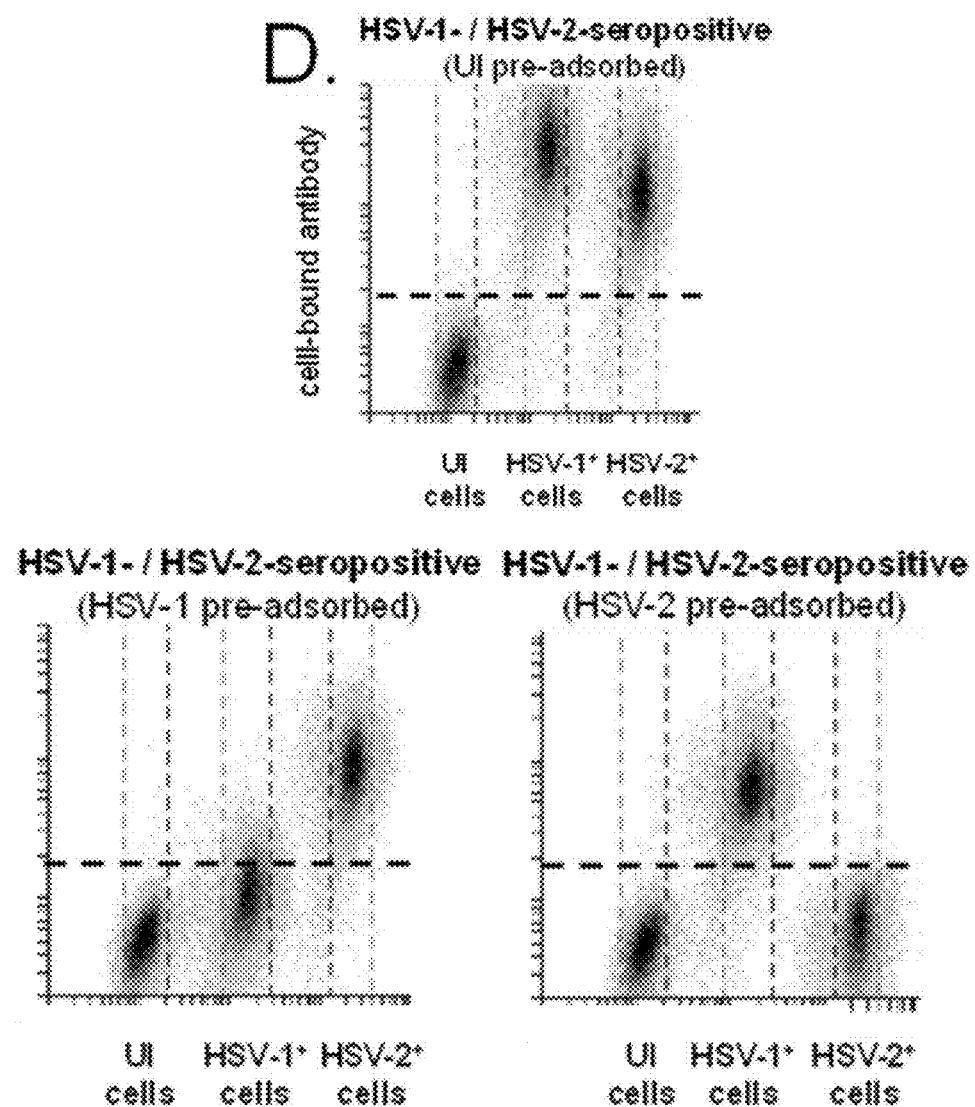
Figure 17:
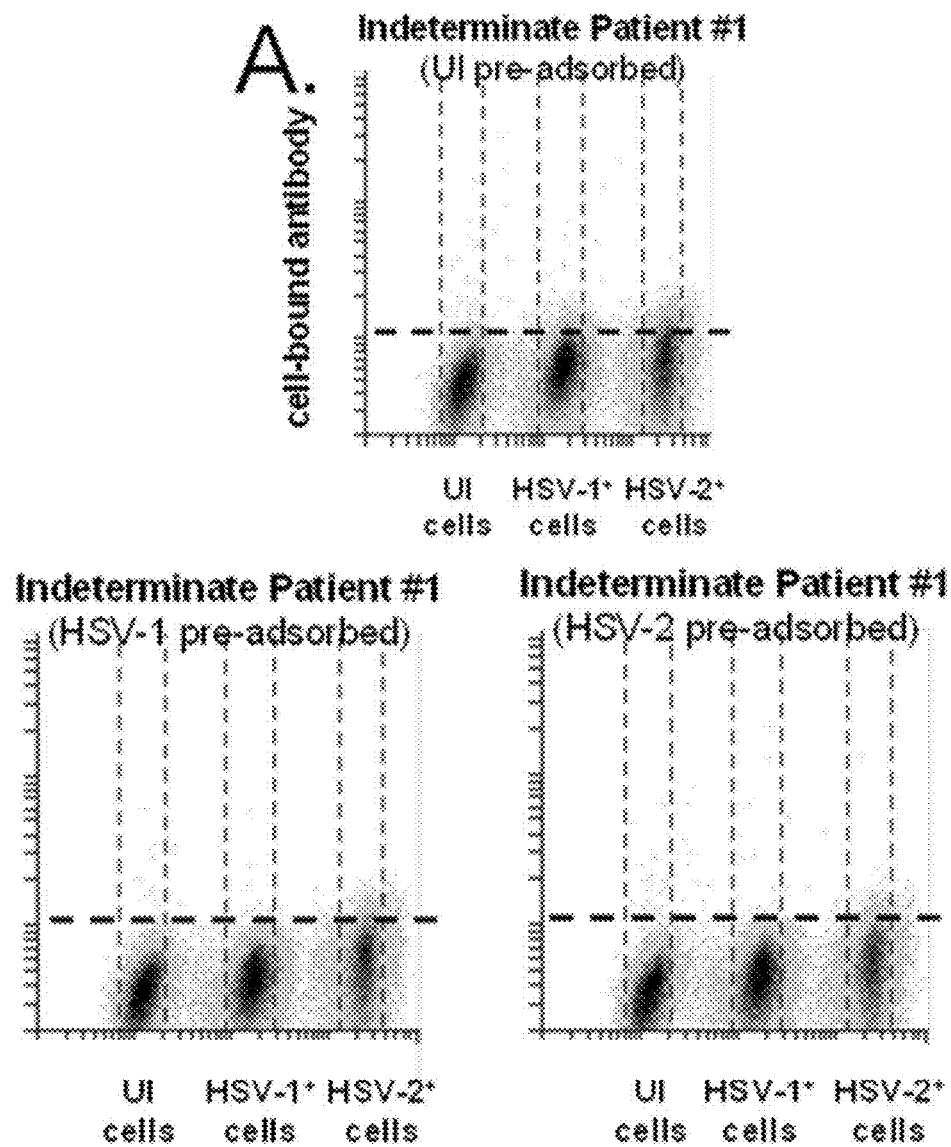
FIG. 17, in three panels as FIG. 17A, FIG. 17B, and FIG. 17C, is as described in FIGS. 15 and 16, except the patient samples are from three indeterminate patients who were classified by the Herpes Western Blot test as "HSV-2 Indeterminate.". None of these patients has HSV-2.
Figure 17:
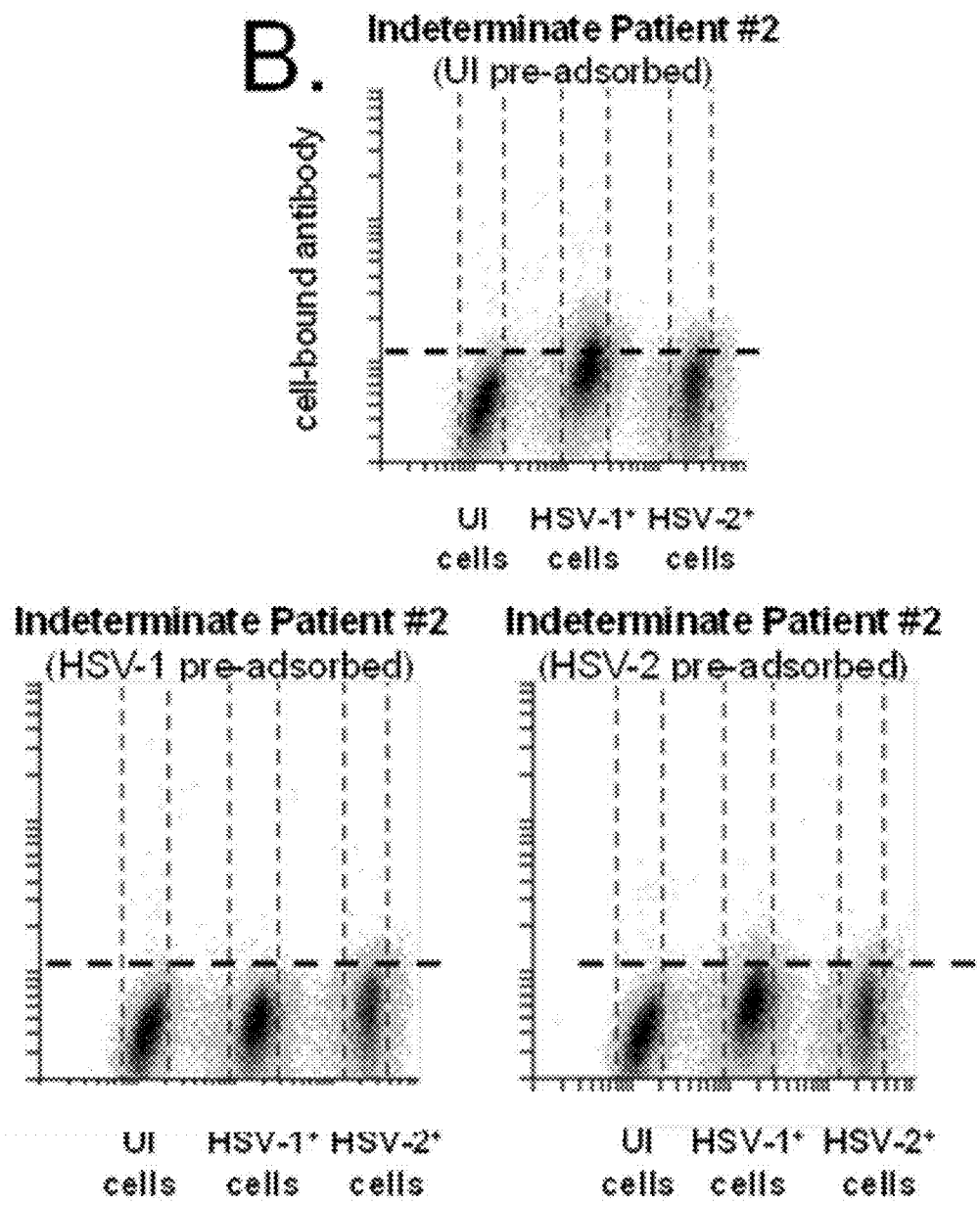
Figure 17:
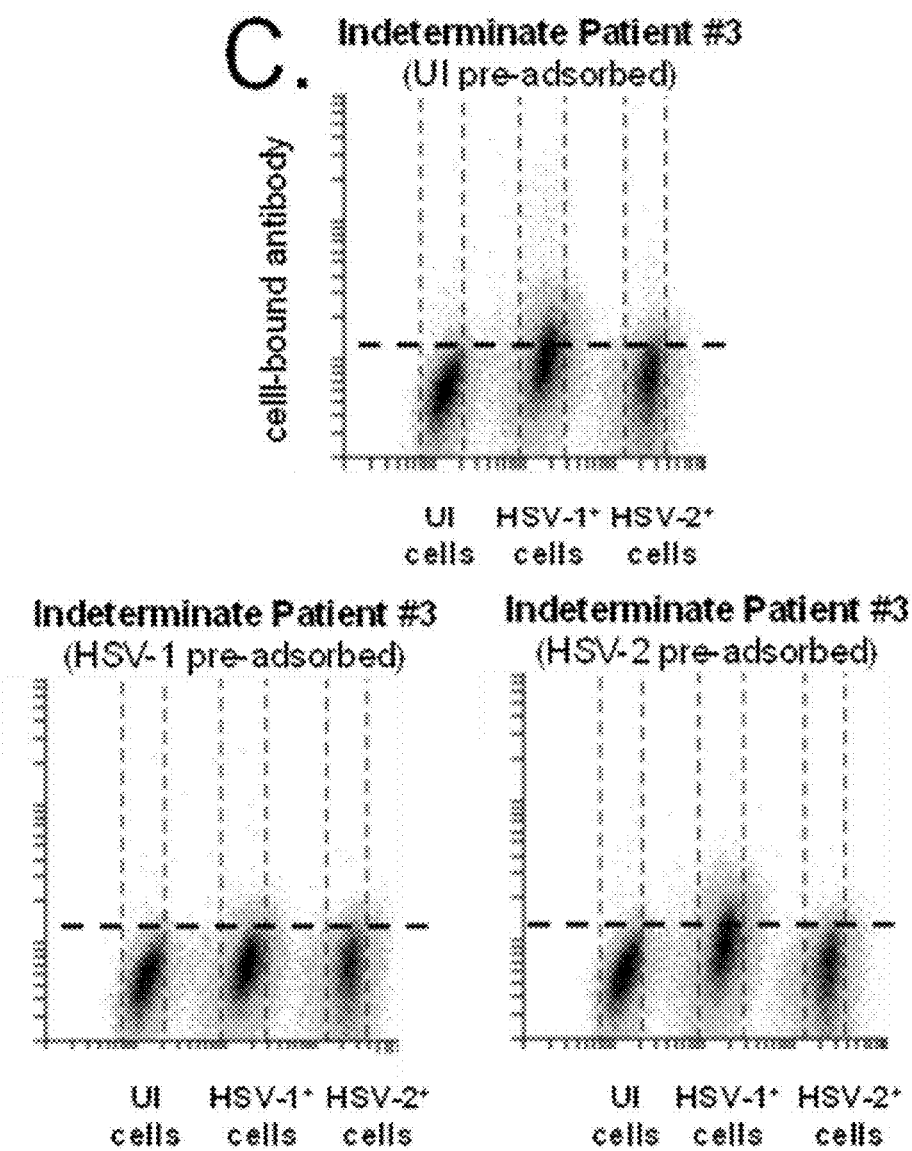
Figure 18:
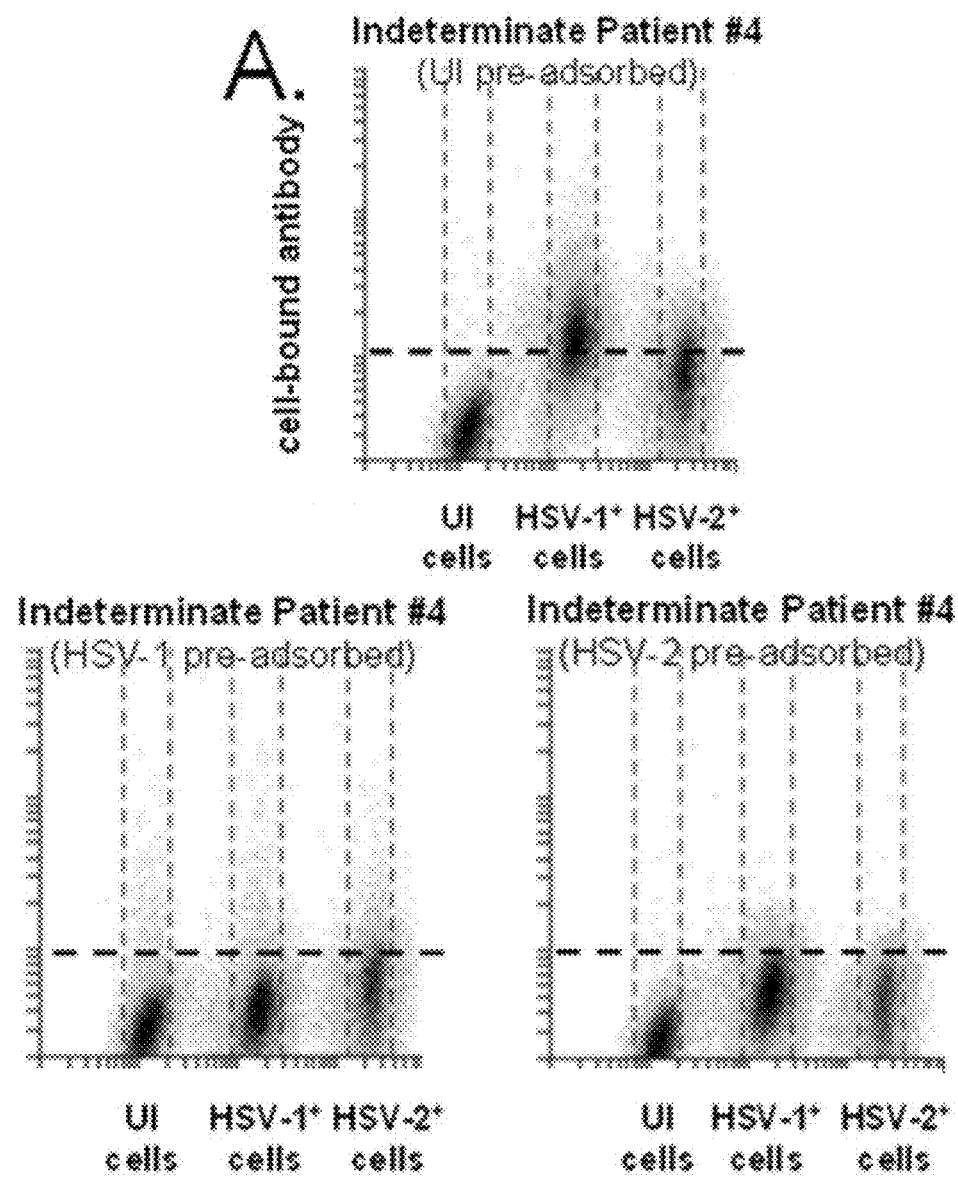
FIG. 18, in three panels as FIG. 18A, FIG. 18B, and FIG. 18C, is as described in FIGS. 15-17, except the patient samples are from three patients who were classified by the Herpes Western Blot test as "HSV-2 Indeterminate.". None of these patients has HSV-2.
Figure 18:
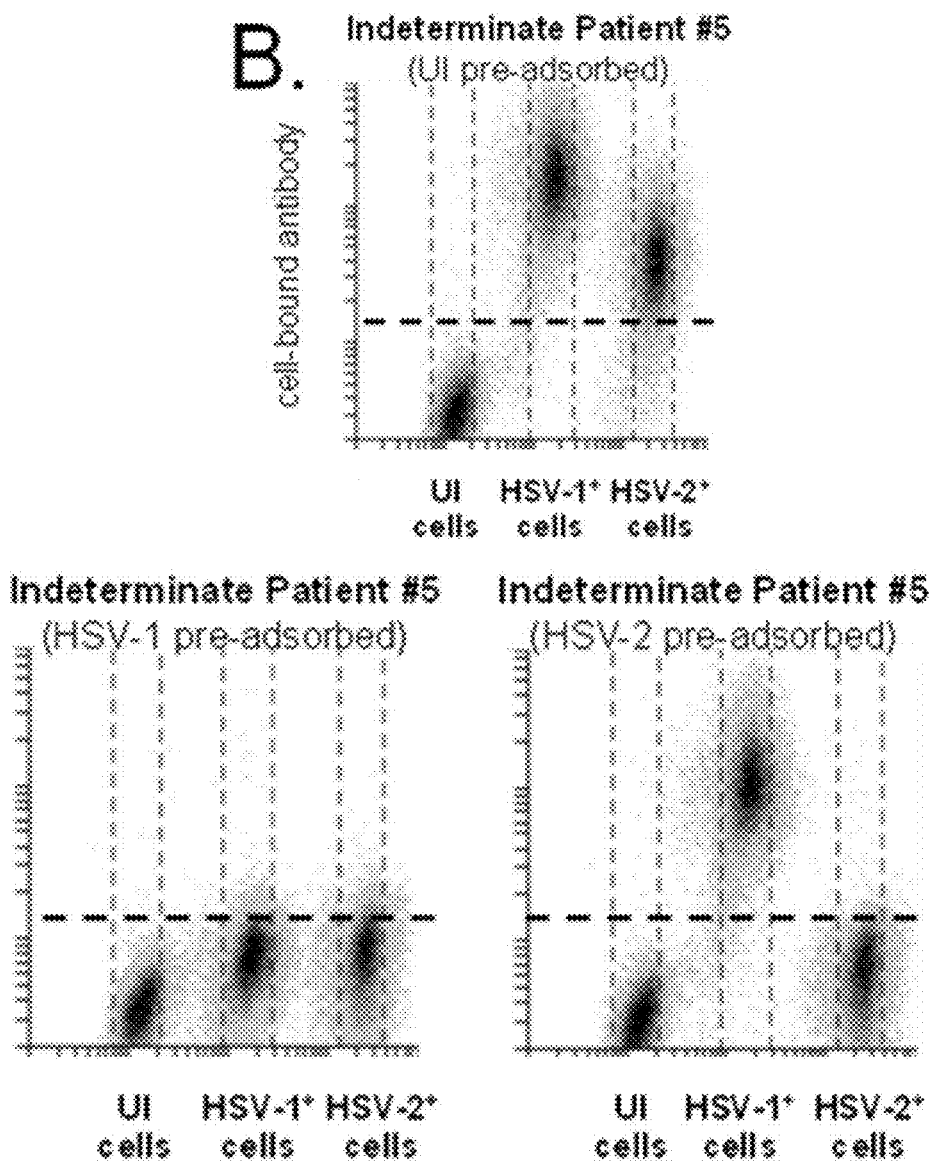
Figure 18:
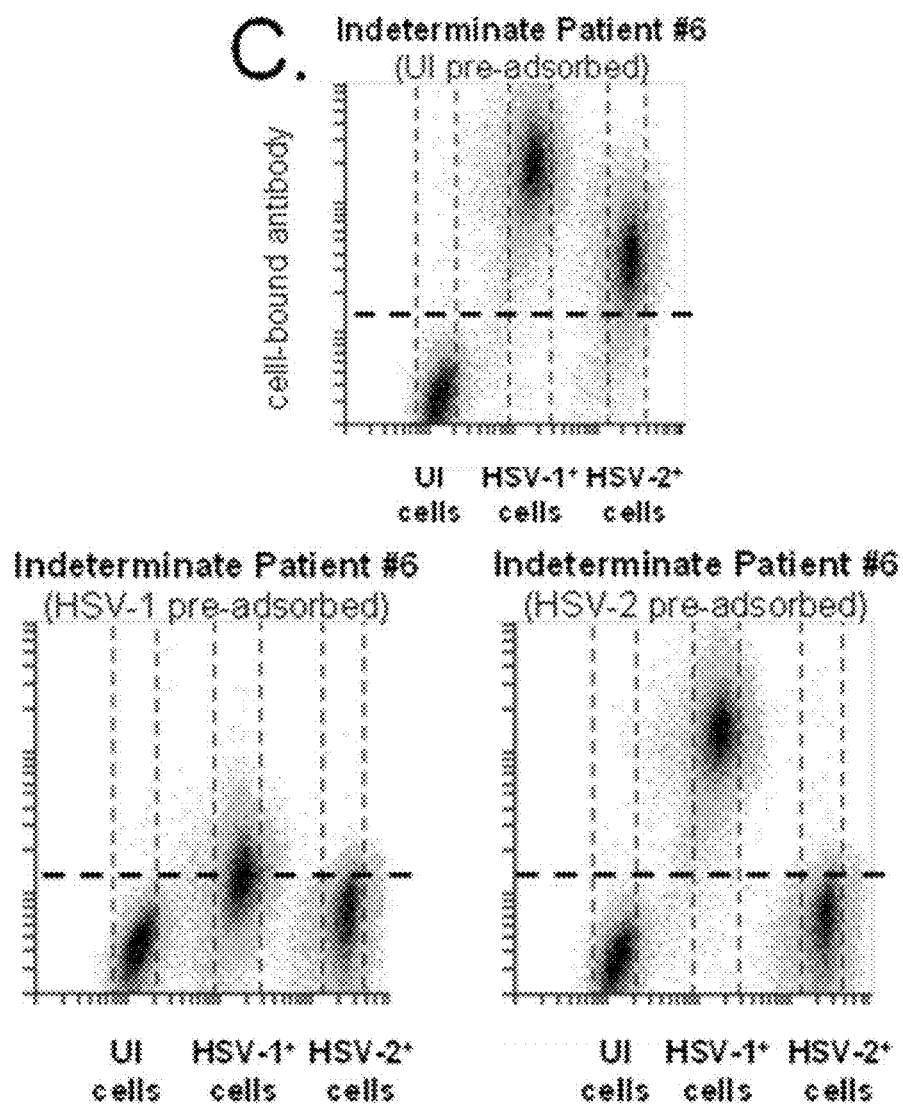

FIG. 16 illustrates the data produced by the flow cytometry-based embodiment of the type-specific ABVIC test with individuals who are known (based on Herpes Western blot) to be HSV-1-seropositive (FIG. 16A), weak HSV-2-seropositive (FIG. 16B), strongly HSV-2-seropositive (FIG. 16C), or HSV-1/HSV-2-double seropositive (FIG. 16D). Each type of individual is considered, as follows.

For individuals who are HSV-1 seropositive, the control "UI preadsorbed" serum sample (left panel in FIG. 16A) shows a $\Delta MFI_{HSV-1}$ that is 63-fold above background and a $\Delta MFI_{HSV-2}$ that is 11-fold above background. When the same serum sample is preadsorbed to a HSV-1-antigen matrix, type-common antibodies and HSV-1-specific antibodies are removed. Hence, in the center panel of FIG. 16A, the $\Delta MFI_{HSV-1}$ is reduced to 1.0-fold above background and the $\Delta MFI_{HSV-2}$ is reduced to about 1.4-fold above background, which indicates that this person does not possess HSV-2-specific antibodies. Finally, when the same serum sample is preadsorbed to a HSV-2-antigen matrix, type-common antibodies and HSV-2-specific antibodies are removed. Hence, in the rightmost panel of FIG. 16A, the $\Delta MFI_{HSV-1}$ is restored to 41-fold above background hence indicating this person has a high titer of HSV-1-specific antibodies.

Based on subsequent statistical considerations (FIGS. 21-22), one can arrive at the following mathematical conclusions about the individual whose blood was drawn for the analysis presented in FIG. 16A (referring to the patient that provided the serum sample as "patient 16A"):

HSV-1: The probability that patient 16A is HSV-1 seronegative is less than 0.01%.

HSV-2: The probability that patient 16A is HSV-2 seronegative is 55%.

Conclusion: Patient 16A is HSV-1 seropositive and HSV-2 seronegative.

For the individuals who are HSV-2 seropositive, the control "UI preadsorbed" serum sample (left panels in FIG. 16B and FIG. 16C) show $\Delta MFI_{HSV-1}$ that are 7 and 30-fold above background and show $\Delta MFI_{HSV-2}$ that are 8 and 47-fold above background, respectively. When these serum samples were preadsorbed to a HSV-1-antigen matrix (center panel of FIG. 16B and FIG. 16C) the $\Delta MFI_{HSV-1}$ is reduced to about 0.2 and 0.9-fold above background, respectively, whereas the $\Delta MFI_{HSV-2}$ is only reduced to 4- and 29-fold above background, which indicates both individuals appear to possess HSV-2-specific antibodies. Finally, when these same serum samples were preadsorbed to a HSV-2-antigen matrix (rightmost panel), the $\Delta MFI_{HSV-1}$ of Patient #1 is reduced to 0.3 indicating they are clearly HSV-1 seronegative (FIG. 16B), whereas the $\Delta MFI_{HSV-1}$ of Patient #2 remains 4.2-fold above background (FIG. 16C). Based on subsequent statistical considerations (FIGS. 21-22), one can arrive at the following mathematical conclusions about these individuals analyzed in FIG. 16B and FIG. 16C (as "patient 16B" also "Patient #1" and "patient 16C" also "Patient #2"):

HSV-1: The probability that patient 16B is HSV-1 seronegative is 87%.

HSV-2: The probability that patient 16B is HSV-2 seronegative is 0.1%.

Conclusion: Patient 16B is HSV-1 seronegative and HSV-2 seropositive.

HSV-1: The probability that patient 16C is HSV-1 seronegative is 3%.

HSV-2: The probability that patient 16C is HSV-2 seronegative is less than 0.01%.

Conclusion: Patient 16C is HSV-1 equivocal and is HSV-2 seropositive.

For the individual who is HSV-1-seropositive and HSV-2 seropositive, the control "UI preadsorbed" serum sample (left panel in FIG. 16D) shows a $\Delta MFI_{HSV-1}$ that is 290-fold above background and a $\Delta MFI_{HSV-2}$ that is 100-fold above background. When this serum sample was preadsorbed to a HSV-1-antigen matrix (center panel of FIG. 16D) the $\Delta MFI_{HSV-1}$ is reduced to 2-fold above background, whereas the $\Delta MFI_{HSV-2}$ is only reduced to 52-fold above background, which indicates this individual possesses HSV-2-specific antibodies. When this serum sample was preadsorbed to a HSV-2-antigen matrix (rightmost panel), the $\Delta MFI_{HSV-1}$ is only reduced to 95-fold above background indicating they are clearly HSV-1 seropositive (FIG. 16D). Based on subsequent statistical considerations (FIGS. 21-22), one can arrive at the following mathematical conclusions about this individual:

HSV-1: The probability that patient 16D is HSV-1 seronegative is less than 0.01%.

HSV-2: The probability that patient 16D is HSV-2 seronegative is less than 0.01%.

Conclusion: Patient 16D is HSV-1 seropositive and HSV-2 seropositive.

Preadsorption of Human Antibodies to Uninfected, HSV-1$^+$, or HSV-2$^+$ Antigen Matrices.

A. Preadsorption to CNBr-Activated Sepharose® 4B Matrix.

Examples of the use of cyanogen-bromide (CNBr)-activated Sepharose® 4B (GE Healthcare Life Sciences) as an UI, HSV-1, or HSV-2 cell antigen matrix for the preadsorption step in the type-specific ABVIC test are shown in FIGS. 23 and 24.

B. Preadsorption to Fixed Vero Cells Attached to a Solid Matrix.

Examples of the use of fixed and permeabilized Vero cells as an UI, HSV-1, or HSV-2 cell antigen matrix for the preadsorption step in the type-specific ABVIC test are shown in FIGS. 15, 16, 17 and 18. In this particular test, UI, HSV-1$^+$, or HSV-2$^+$ Vero cells were fixed to the substrate of the plastic dish in which they were cultured, and this served as the cell antigen matrix to which human serum was preadsorbed. Similarly, suspensions of UI, HSV-1$^+$, or HSV-2$^+$ Vero cells have been used as a cell antigen matrix for preadsorption of human serum prior to flow cytometry analysis of human antibody binding to test cells.

Fixed test cells or cell antigen matrices that are (i) uninfected, (ii) HSV-1$^+$, and/or (iii) HSV-2$^+$ are stable over time. The concept of fixation, as the term implies, involves "fixing" a biological tissue into a form that does not decay, and is thus stable over time. This is the basis of embalming humans for funeral preparations, which was practiced in ancient Egypt to produce preserved mummies. The use of fixatives such as formaldehyde, methanol, ethanol, acetone, etc. has been commonplace in biology since the 19$^{th}$ century. In studies in the inventor's laboratories, (1) suspensions of fixed uninfected, HSV-1$^+$, or HSV-2$^+$ Vero test cells or (2) uninfected, HSV-1$^+$, or (iii) HSV-2$^+$ cell antigen matrices are stable at 4° C. for at least 1 month.

The uninfected (UI) control antibody test is sufficient to distinguish HSV-seronegative from HSV-seropositive, but does not differentiate whether a person is infected with HSV-1, HSV-2, or both. The leftmost column of panels in FIG. 16D illustrate that all HSV-1-seropositive and HSV-2 seropositive individuals possess both type-common antibodies that cross-react with both HSV-1$^+$ and HSV-2$^+$ Vero test cells. Thus, in the absence of preadsorption or after preadsorption to UI cells, it is impossible to clearly differentiate whether a patient is infected with HSV-1 and/or HSV-2.

The presence of HSV-1-specific antibody in a subject's serum permits calculation of the probability that the subject was HSV-1 seronegative, and thus one could infer that a person is HSV-1 seropositive if their probability of being HSV-1 seronegative is less than 0.5%. Data that supports these points are presented in FIG. 16 (right-most column), FIGS. 19-20 (HSV-2 preadsorbed), and FIG. 22A.

The presence of HSV-2-specific antibody allows us to calculate the probability a person is HSV-2 seronegative, and thus we may infer a person is HSV-2 seropositive if their probability of being HSV-2 seronegative is less than 0.5%. Data that support these points are presented in FIG. 16 (center column), FIGS. 19-20 (HSV-1 preadsorbed), and FIG. 22B.

The Type-Specific ABVIC Asay combines the (i) uninfected control test, (ii) HSV-1-specific antibody test, and the (iii) HSV-2-specific antibody test. Data that support these points are presented in FIGS. 15-18 and FIGS. 23-24.

The Type-Specific ABVIC Assay is highly quantitative and permits statistical interpretation of the probability that a person is HSV-1 and/or HSV-2 seropositive. Data that supports these points are presented in FIGS. 21-22.

The quantitative and statistical power of the Type-Specific ABVIC Assay allows the test to resolve Indeterminate Test Results of Herpes Western Blot tests. Data that support these points are presented in FIGS. 17, 18, 20 and 22. All of the Indeterminate Patients under study were informed based on a prior Herpes Western Blot that they may be infected with HSV-2. The serum of n=7 Indeterminate Patients was analyzed in the type-specific ABVIC Assay (per FIGS. 21-22), and the raw data from 6 of those 7 are presented in FIGS. 17 and 18 and are statistically summarized for "patients 17A-17C" and "patients 18A-18C," as follows:

HSV-1: The probability that patient 17A is HSV-1 seronegative is 61%.

HSV-2: The probability that patient 17A is HSV-2 seronegative is 79%.

Conclusion: Patient 17A is HSV-1 seronegative and HSV-2 seronegative.

HSV-1: The probability that patient 17B is HSV-1 seronegative is 77%.

HSV-2: The probability that patient 17B is HSV-2 seronegative is 41%.

Conclusion: Patient 17B is HSV-1 seronegative and HSV-2 seronegative.

HSV-1: The probability that patient 17C is HSV-1 seronegative is 3%.

HSV-2: The probability that patient 17C is HSV-2 seronegative is 85%.

Conclusion: Patient 17C is HSV-1 equivocal and HSV-2 seronegative.

HSV-1: The probability that patient 18A is HSV-1 seronegative is 0.4%.

HSV-2: The probability that patient 18A is HSV-2 seronegative is 45%.

Conclusion: Patient 18A is weakly HSV-1 seropositive and HSV-2 seronegative.

HSV-1: The probability that patient 18B is HSV-1 seronegative is less than 0.01%.

HSV-2: The probability that patient 18B is HSV-2 seronegative is 8%.

Conclusion: Patient 18B is HSV-1 seropositive and HSV-2 seronegative.

HSV-1: The probability that patient 18C is HSV-1 seronegative is less than 0.01%.

HSV-2: The probability that patient 18C is HSV-2 seronegative is 30%.

Conclusion:. Patient 18C is HSV-1 seropositive and HSV-2 seronegative.

General Development

Development of the Two Cell Population ABVIC (Antibody Binding to Virus-Infected Cells) Assay Introduction There exists a need for a correlate of immunity to herpes simplex virus 2 (HSV-2) that can be used to differentiate whether a HSV-2 vaccine elicits robust or anemic protection against genital herpes.

It has been suggested that past difficulties in identifying a clinically useful correlate of immunity to HSV-2 may have stemmed from a failure to identify the correct parameter of the T-cell response that controls HSV-2 in vivo [Rouse and Kaistha, 2006]. However, there is a second possibility. Most attempts to identify a correlate of immunity to HSV-2 have focused on monovalent (gD-2) or bivalent (gB-2+gD-2) subunit vaccines that present less than 3% of HSV-2's 40,000 amino-acid proteome to the immune system [Shlapobersky et al., 2012; Bernstein et al., 2010; Bourne et al., 2005; Bernstein, 2005; Bourne et al., 2003; Khodai et al., 2011; Bernstein et al., 2011; Allen et al., 1990; Weir et al., 1989; Kuklin et al., 1997; Manickan et al., 1995; Eo et al., 2001; Natuk et al., 2006; Orr et al., 2007; Karem et al., 1997; Brans and Yao, 2010; Meigner et al., 1988]. This approach does not consider HSV-2's full complement of antigens; at least 20 viral proteins are known targets of the human B- and T-cell response to HSV-2 [Hosken et al., 2006; Laing et al., 2010; Gilman et al., 1981]. Therefore, it was postulated that a correlate of immunity might be more readily identified if: 1) animals were immunized with a polyvalent immunogen such as a live virus; and/or 2) the magnitude of the vaccine-induced immune response was gauged in terms of the IgG antibody response to all of HSV-2's antigens (pan-HSV-2 IgG).

The current study was initiated to test these predictions. A novel, flow cytometry-based assay was developed to measure pan-HSV-2 IgG levels. Using this assay, 117 naïve and immunized animals were analyzed to compare pre-challenge serum levels of pan-HSV-2 IgG to two measures of protection against HSV-2. Pre-challenge pan-HSV-2 IgG levels and protection against HSV-2 were compared in mice and/or guinea pigs immunized with a gD-2 subunit vaccine, wild-type HSV-2, or one of several attenuated HSV-2 ICP0$^-$ viruses (0Δ254, 0Δ810, 0ΔRING, or 0ΔNLS). These six HSV-2 immunogens elicited a wide range of pan-HSV-2 IgG levels spanning an about 500-fold range. For 5 of the 6 immunogens tested, pre-challenge levels of pan-HSV-2 IgG quantitatively correlated with reductions in HSV-2 challenge virus shedding and increased survival frequency following HSV-2 challenge. Collectively, the results suggest that pan-HSV-2 IgG levels may provide a simple and useful screening tool for evaluating the potential of a HSV-2 vaccine candidate to elicit protection against HSV-2 genital herpes.

Materials and Methods

Ethics Statement

Mice and guinea pigs were handled in accordance with the National Institutes of Health Guide for the Care and Use of Laboratory Animals. This study was approved by the Southern Illinois University School of Medicine Laboratory Animal Care and Use Committee, and was performed as described under approved protocol 205-08-019.

Cells and Viruses

Vero cells and U2OS cells were obtained from the American Type Culture Collection (Manassas, Va.), and ICP0-complementing L7 cells were kindly provided by Neal Deluca (University of Pittsburgh; Samaniego et al., 1998). All cells were propagated in Dulbecco's Modified Eagle's medium (DMEM) supplemented with 5% fetal bovine serum (FBS), 100 U/ml penicillin G, and 100 mg/ml streptomycin, hereafter referred to as "complete DMEM." Wild-type HSV-2 MS (ATCC) was propagated and titered on Vero cells. The HSV-2 ICP0$^-$ mutant viruses used in this study (HSV-2 0Δ810, 0Δ254, and 0ΔRING: Halford et al., 2010) were propagated in U2OS cells and titered in ICP0-complementing L7 cells.

HSV-2 Challenge Studies

Figure 2:
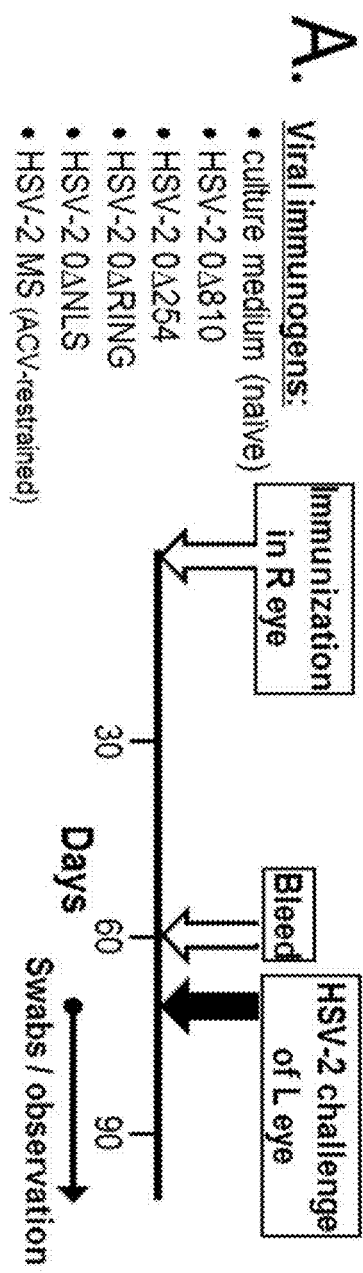
FIG. 2 shows that pan-HSV-2 IgG levels correlate with protection against ocular HSV-2 challenge in mice.
Figure 2:
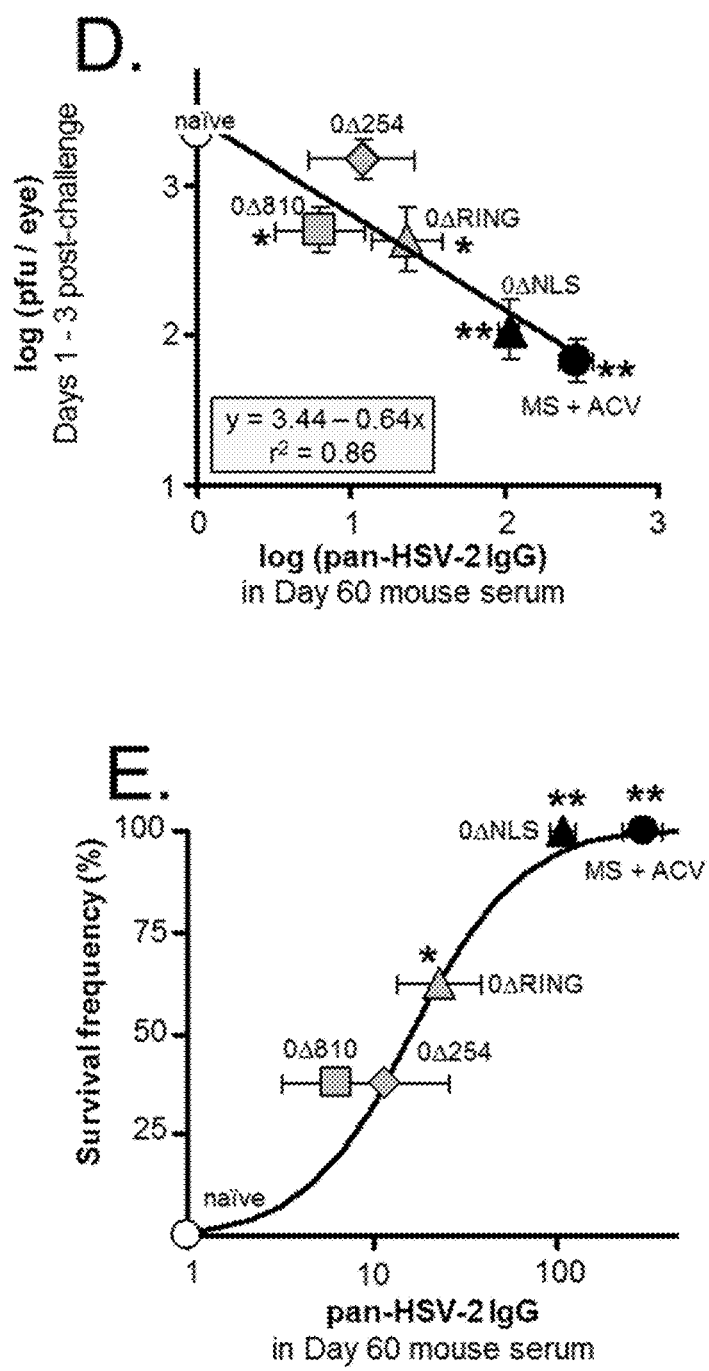
Figure 3:
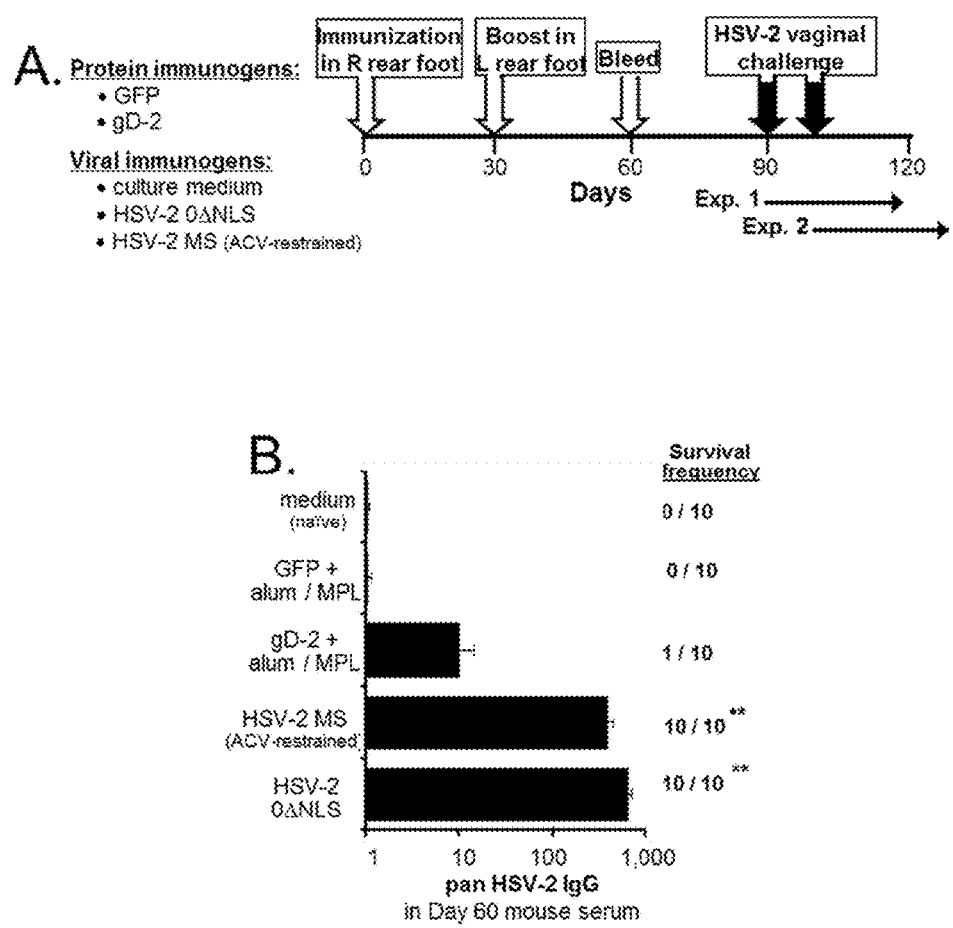
FIG. 3 shows that pan-HSV-2 IgG levels correlate with protection against vaginal HSV-2 challenge in mice.
Figure 3:
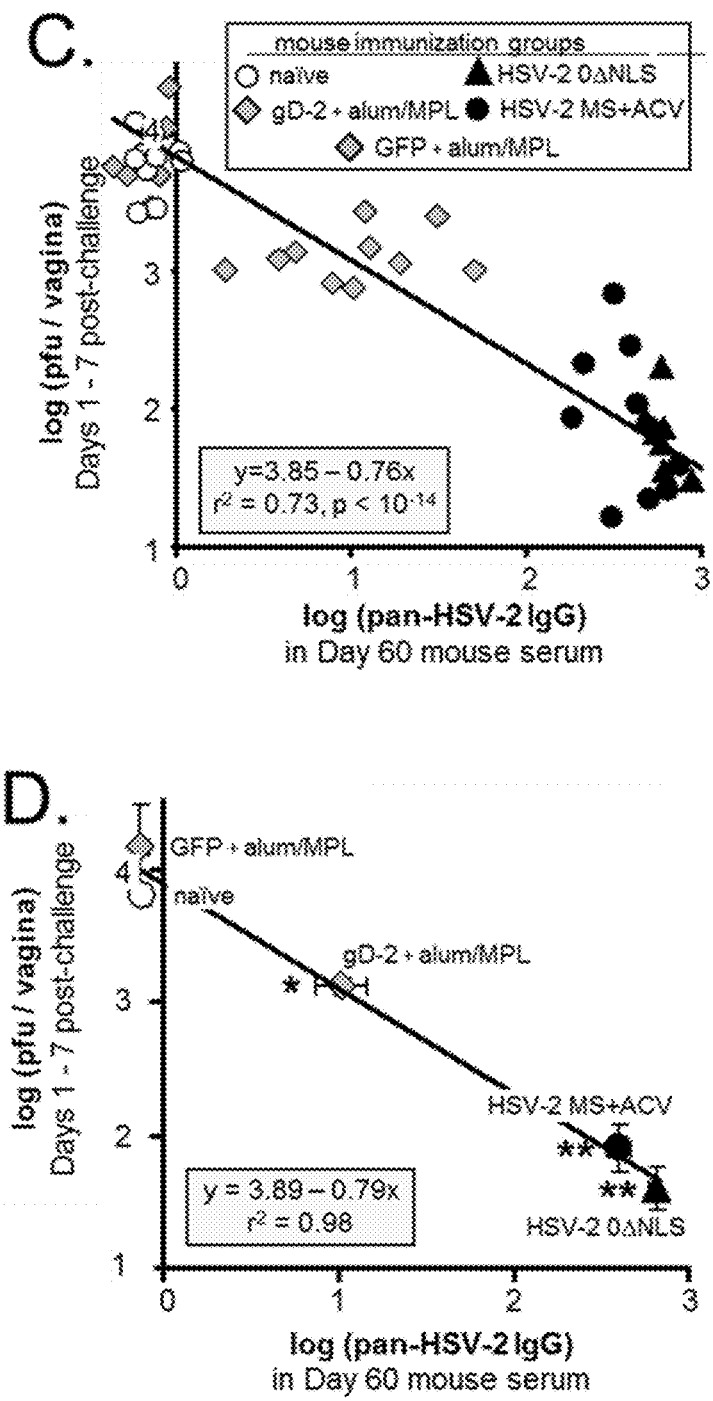

A retrospective analysis of serum obtained two years earlier was performed in the current study (FIGS. 2A and 3A). The details of these studies are described elsewhere [Halford et al., 2011; Halford et al., 2010]. Prospective vaccine-challenge studies in guinea pigs are described in detail, as follows.

Figure 4:
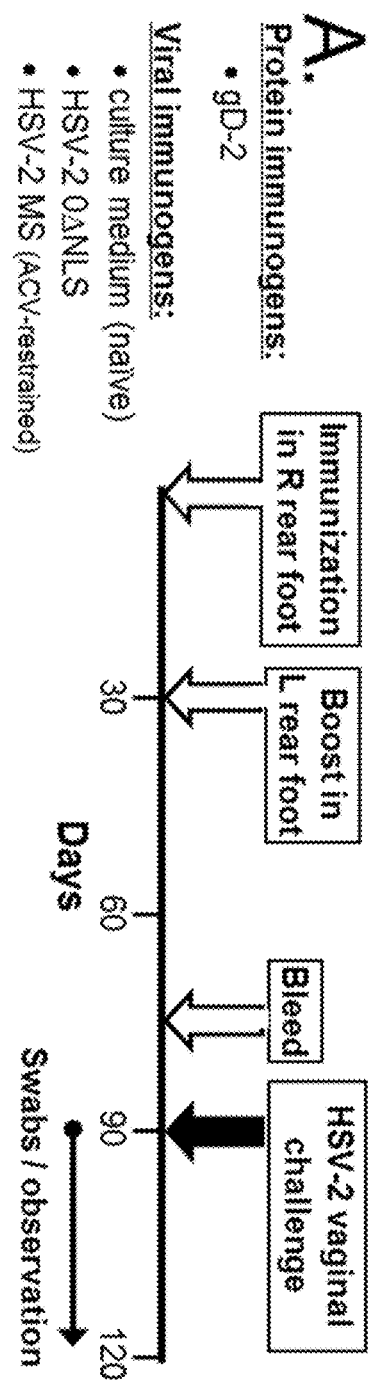
FIG. 4 shows that pan-HSV-2 IgG levels correlate with protection against vaginal HSV-2 challenge in guinea pigs.
Figure 4:
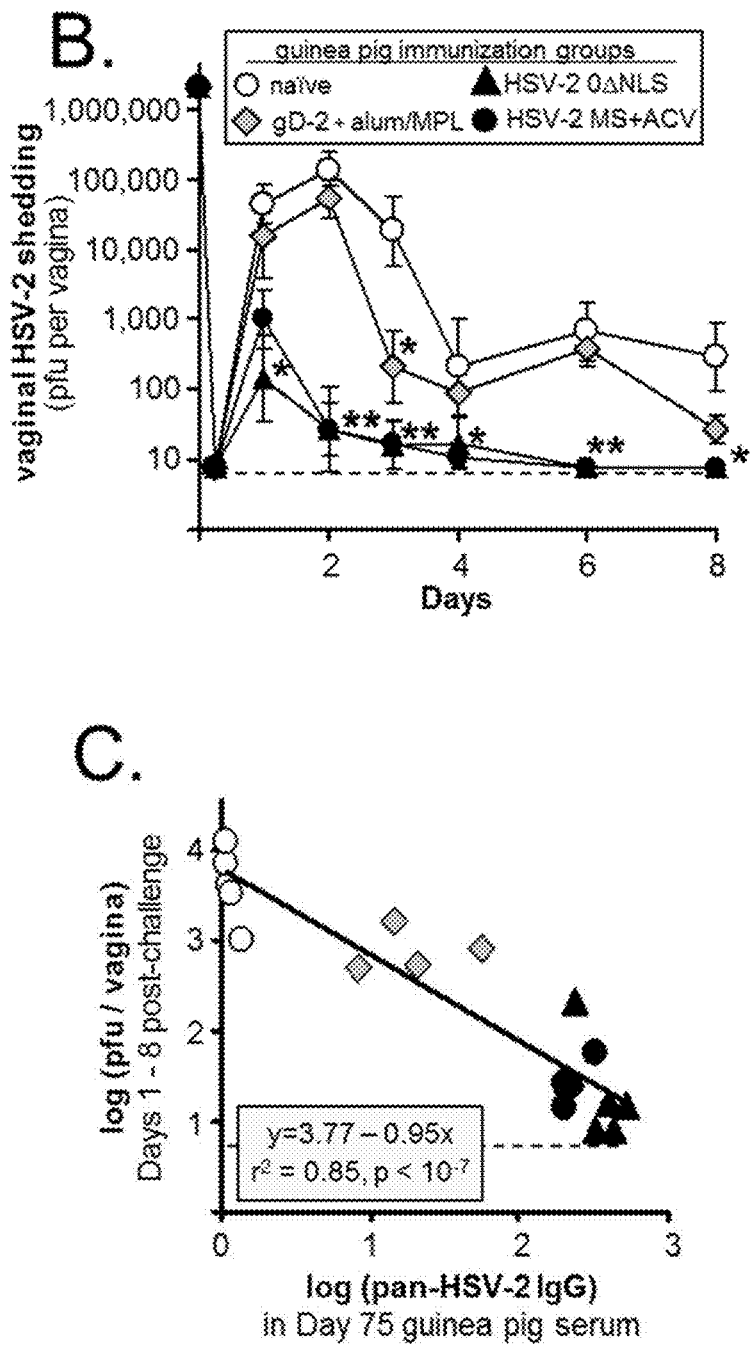

Female Hartley guinea pigs were obtained at an average weight of 250 g from Charles River (Wilmington, Mass.). On Day 0, guinea pigs were anesthetized by i.p. administration of xylazine (5 mg/kg) and ketamine (30 mg/kg), and were immunized via right, rear footpad injection of 100 µl containing: 1) complete DMEM (naïve); 2) 2×10$^6$ pfu HSV-2 0ΔNLS; 3) 2 ×10$^6$ pfu HSV-2 MS; or 4) 5 µg recombinant glycoprotein D-2 (gD-2) antigen+20 µg monophosphoryl lipid A (Avanti Polar Biolipids)+Imject® alum adjuvant (Thermo Scientific). The gD-2 antigen was expressed from a baculovirus vector [Nicola et al., 1996] and has been used as a vaccine antigen in numerous studies [Bernstein et al., 2010; Bernstein et al., 2011; Halford et al., 2011]. The details of purification of this His-tagged gD-2 protein are described elsewhere [Halford et al., 2011]. Guinea pigs immunized with HSV-2 MS received 1 mg/ml oral acyclovir in their drinking water between Days 0 and 20 post-immunization to limit viral pathogenesis; 100% of guinea pigs survived their primary exposure to HSV-2 MS without developing overt signs of disease. Guinea pigs received an equivalent immunization in their left, rear footpads on Day 30 (per design shown in FIG. 4A). HSV-2 MS-immunized guinea pigs were not treated with acyclovir at the time of the second, booster immunization. Guinea pigs were bled on Day 75 post-immunization by saphenous vein puncture with a 25 g needle and blood was collected with a heparinized, Natelson blood collecting tube. The serum fraction was collected and stored at −80° C.

All guinea pigs were challenged with HSV-2 MS on Day 90, as follows. Prior to viral inoculation, guinea pigs were anesthetized by i.p. administration of xylazine (5 mg/kg) and ketamine (30 mg/kg). Naïve and immunized guinea pigs were vaginally challenged with wild-type HSV-2 MS by: 1) first clearing the mucus plug from the vagina with a cotton swab; 2) twirling a second cotton swab inside the vaginal vault to further dry the walls of the vagina; and 3) instilling the vaginal vault with 40 µl complete DMEM containing 2×10$^6$ pfu of HSV-2 MS.

Viral titers in the vaginal vault of challenged guinea pigs were determined at 8 hours post-challenge (eclipse phase) and on Days 1, 2, 3, 4, 6, and 8 post-challenge by inserting and twirling a swab in the vaginal vault of guinea pigs, and transferring the tip into 0.4 ml complete DMEM. Viral titers were determined as described above. Guinea pigs were monitored daily, and animals that exhibited severe perivaginal ulceration were euthanized at the earliest possible time. The perivaginal region of all guinea pigs was photographed on Day 7 post-challenge. Surviving guinea pigs were euthanized on Day 30 post-challenge.

Adoptive Transfer of HSV-2 Antiserum to Inbred Strain 129 Mice

Female strain 129 mice were obtained at 6- to 8-weeks of age from Charles River (Wilmingtion, Mass.). On Days 0 and 30, n=10 mice were anesthetized by i.p. administration of xylazine (7 mg/kg) and ketamine (100 mg/kg), and were immunized via right and left rear footpad injection, respectively, of 50 µl containing 10$^6$ pfu HSV-2 0ΔNLS. On Day 85, n=5 HSV-2 0ΔNLS-immunized mice were sacrificed to harvest HSV-2 antiserum, and n=5 age-matched, naïve mice were sacrificed to harvest naïve serum. On Day 90, naïve mice received an adoptive transfer of 0.25 ml pooled HSV-2 antiserum or 0.25 ml pooled naïve serum. Immediately following adoptive transfer, these n=10 naïve mice were anesthetized by i.p. administration of xylazine (7 mg/kg) and ketamine (100 mg/kg), and were challenged with 100,000 pfu per eye of HSV-2 MS. Likewise, n=5 mice immunized with HSV-2 0ΔNLS (on Days 0 and 30) were anaesthetized and challenged at the same time with 100,000 pfu per eye of HSV-2 MS. HSV-2 MS shedding was monitored in these mice as described elsewhere [Halford et al., 2011].

Antibody Capture ELISA to Enumerate Pan-HSV-2 IgG Antibody Levels in Serum

High-binding EIA 96-well plates (Costar, Corning, N.Y.) were coated overnight (about 18 hours) at 4° C. with 100 µl per well of sodium carbonate buffer (pH 9.6) containing 0.2 µg per ml total HSV-2 antigens. Total HSV-2 antigen was isolated from HSV-2 infected Vero cells, as follows: five 100-mm dishes of Vero cells (8 million cells per dish) were inoculated with 3 pfu per cell of HSV-2 MS and incubated at 37° C. for 16 hours. Culture medium was aspirated from dishes, cells were rinsed with 5 ml PBS per dish, and cells were covered in 2 ml of sodium carbonate buffer (pH 9.6) per dish and frozen at −80° C. HSV-2 cell lysates were thawed and clarified by low-speed centrifugation to remove cell debris. The clarified supernatant had a protein concentration of 10 µg/ml, and was frozen in 0.2 ml aliquots. For each 96-well plate to be coated with HSV-2 antigen, a single aliquot of HSV-2 total antigen was diluted 1:50 (0.2 µg per ml) and used to coat a high-binding EIA plate. After overnight (about 18 hours) coating with total HSV-2 antigen, wells were blocked for 2 hours with 400 µl of 2% dry milk dissolved in phosphate-buffered saline (PBS)+0.02% Tween-20 (polyoxyethylene-20-sorbitan monolaurate), hereafter referred to as PBS-T buffer.

Each serum sample to be tested was diluted 2.5:250 in PBS+1% fetal bovine serum+0.02% Tween-20. After discarding blocking buffer from ELISA plates, duplicate 100-µl samples of diluted serum were added to total HSV-2 antigen-coated wells and were incubated for 2 hours.

ELISA plates were rinsed three times with an excess of PBS-T buffer prior to the addition of 100 µl secondary antibody diluted 1:1500 in PBS-T buffer; the secondary antibody was alkaline phosphatase-conjugated goat anti-mouse IgG Fc fragment (Rockland Immunochemicals, Gilbertsville, Pa.). After allowing 1 hour, secondary antibody was rinsed from plates seven times with PBS-T buffer, and 200 µl of p-nitrophenyl phosphate substrate (Sigma Chemical Co., St. Louis, Mo.) was added to each well, and colorimetric development ($OD_{405}$) was measured after a 30-minute incubation at room temperature. The quantitative relationship between abundance of log (pan-HSV-2 IgG) (x) and $OD_{405}$ (y) was defined using a 0.33-log dilution series of HSV-2 antiserum and a hyperbolic tangent-based standard curve (FIG. 9A). The abundance of log (pan-HSV-2 IgG) in each serum sample was derived from $OD_{405}$ values using a reciprocal hyperbolic arctangent equation of the form $$x = x_{50} + \Delta X \cdot \arctan\left(\frac{OD_{405} - y_{50}}{\Delta Y}\right),$$

as described elsewhere [Halford et al., 2010; Halford et al., 2005a].

Flow Cytometry Assay to Enumerate Pan-HSV-2 IgG Levels in Mouse and Guinea Pig Serum Single-cell suspensions of a mixture of HSV-2$^+$ cells and uninfected (UI) cells were generated, as follows. Twelve 100-mm dishes were seeded with $7 \times 10^6$ Vero cells per dish in complete DMEM, and six dishes were inoculated 6 hours later with 3 pfu per cell of HSV-2 MS. HSV-2$^+$ Vero cells were harvested 12 hours after inoculation, and UI Vero cells were harvested in parallel at the same time.

Both cell populations were dispersed by aspirating culture medium, rinsing each dish with 5 ml PBS, and adding 2 ml PBS+5 mM ethylene diamine tetraacetic acid (EDTA) pH 8.0. It should be noted that PBS+5 mM EDTA was sufficient to cause Vero cells to lift and detach from one another without the use of trypsin. In the case of HSV-2$^+$ cells, the PBS+5 mM EDTA solution was supplemented with 1 µM carboxyfluorescein diacetate, succinimidyl ester (CFSE; Anaspec, Fremont, Calif.) to label HSV-2$^+$ cells with a green fluorophore.

Cells were incubated at room temperature on a rocking platform for 10 minutes until cells began to lift, and were then dispersed by trituration with the aid of a P-1000 pipettor. All dispersed UI cells were placed in a single 50-ml conical, and all dispersed HSV-2$^+$ cells were placed in a second 50-ml conical, and both were centrifuged at 200× g for 5 minutes to pellet cells. Supernatants were decanted, cell pellets were resuspended in 12 ml PBS, and an equal volume of 2× fixative (7.4% formaldehyde+4% sucrose) was added.

Cells were incubated in 1× fixative for 20 minutes, centrifuged, and resuspended in 24 ml of 90% methanol to permeabilize the cells. After a 10 minute incubation, cells were centrifuged, resuspended in PBS+3% fetal bovine serum (PBS-F), and cell clumps were removed by passage through a 40 µM, nylon mesh cell strainer (BD Biosciences, San Jose, Calif.) followed by passage through a 25-gauge needle.

Cell density in single-cell suspensions of UI Vero cells and CFSE-labeled HSV-2$^+$ cells was determined, and UI cells and HSV-2$^+$ cells were combined in an approximate 2:1 ratio. Cells were centrifuged, resuspended at a concentration of $1.25 \times 10^6$ cells per ml in PBS-F-Ig block solution (i.e., PBS-F supplemented with 20 µg/ml each of donkey γ-globulin, goat γ-globulin, and human γ-globulin; Jackson Immunoresearch Laboratories, Inc., West Grove, Pa.).

Aliquots of UI and HSV-2$^+$ cells (400 µl; 500,000 cells) were placed in 1.7 ml microfuge tubes, and 2 µl of 1:30 diluted serum was added to each cell suspension to achieve a net serum dilution of 1:6,000. Cells were incubated at room temperature for four hours on a LabQuake® rotisserie hybridization rotator to keep cells in suspension by rotation (Barnstead International, Dubuque, Iowa), and primary antibody was removed by two, sequential 1.25 ml PBS-F rinses, where a swinging bucket centrifuge was used to pellet cells and rinse supernatant was aspirated.

To enumerate the amount of IgG antibody bound to HSV-2$^+$ versus UI cells, cells were incubated with a 1:1,000 dilution of APC-conjugated goat-anti mouse IgG Fc fragment or APC-conjugated donkey anti-guinea pig IgG (H+L) (Jackson Immunoresearch Laboratories, Inc.). After an 1-hour incubation, excess secondary antibody was removed by three, sequential 1.25 ml PBS-F rinses.

Cells were resuspended in a total volume of 0.2 ml PBS-F and analyzed by two-color flow cytometry in the FL1 and FL4 channels of an Accuri™ C6 flow cytometer using CFlow software (Accuri Cytometers, Inc., Ann Arbor, Mich.). On average, 125,000 events were recorded per sample; specifically, the flow cytometer was set to record events until 25,000 single HSV-2$^+$ cells were included in the data set. Pan-HSV-2 IgG levels in each serum sample were calculated based on the difference in mean fluorescent intensity (ΔMFI) of 25,000 HSV-2$^+$ cells versus ~50,000 UI cells (FIG. 1). Background fluorescence was defined as the average ΔMFI-value observed in cell suspensions incubated with naïve serum.

Mathematical and Statistical Analysis of Results

Unless otherwise specified, all values presented are the mean±standard error of the mean (sem) of replicate samples. Viral titers were determined by microtiter plaque assay and were statistically analyzed on a logarithmic scale (e.g., log [pfu/vagina]). Infectious virus was not detectable in some ocular or vaginal swabs of well-immunized animals. In such events, the sample was assigned a value of 8 pfu per swab (i.e., the lower-limit of detection of the assay), such that all samples could be analyzed on a logarithmic scale. The significance of differences in multiple group comparisons was compared by one-way analysis of variance (ANOVA) followed by Tukey's post hoc t-test using GraphPad Instat™ v3.10 software (GraphPad Software, Inc., La Jolla, Calif.). The significance of difference between two groups was performed using the "t-test assuming equal variances" function of Microsoft Excel. The significance of differences in survival frequency was determined by Fisher's Exact Test using freely available online software (Preacher and Briggs, 2001).

All data were statistically analyzed using logarithmic values. Linear regression analysis was performed by the method-of-least-squares using the "regression" analysis function in Microsoft Excel, and was used to calculate the goodness-of-fit ($r^2$-value) and the probability (p) that the y-variable did not change as a function of the x-variable.

The coefficient-of-variance values reported in FIG. 6 were calculated for each HSV-2 antiserum dilution by the formula, 100×(standard deviation of triplicate samples mean of triplicate samples). The reported values in FIG. 6 represent the mean±sem coefficient-of-variance for all HSV-2 antiserum dilutions in the linear range of the assay (i.e., 1:21-1:1,000 dilutions for the neutralization assay; 1:100-1:100,000 dilutions for the antibody capture ELISA; and 1:6,000-1:6,000,000 dilutions for the flow cytometry assay).

Results

A Flow Cytometry-Based Assay to Measure Pan-HSV-2 IgG Antibody Levels

The presence of serum IgG antibodies that bind total HSV-2 antigens (pan-HSV-2 IgG) may be qualitatively tested by immunofluorescent staining of HSV-2 plaques in fixed Vero cell monolayers (FIGS. 1A and 1B). A more quantitative, flow-cytometry-based variant of this assay was developed. Single-cell suspensions of HSV-2-infected (HSV-2$^+$) and uninfected (UI) Vero cells were obtained by dispersing culture monolayers, fixing and permeabilizing cells, and filtering through 40 μm mesh and a 25-g needle to remove cell clumps. To permit antibody staining of HSV-2$^+$ versus UI cells in a single reaction, HSV-2$^+$ cells were labeled with the green fluorophore carboxyfluorescein diacetate, succinimidyl ester (CFSE).

Suspensions of about 30% HSV-2$^+$ cells and about 70% UI cells were incubated with serum from naïve mice or HSV-2-immunized mice, and were fluorescently labeled with allophycocyanin (APC)-anti-mouse IgG Fc fragment secondary antibody. Antibody-labeled cells were analyzed by 2-color flow cytometry (FIGS. 1C and 1D). When cell suspensions were incubated with a 1:6,000 dilution of naïve mouse serum, similar levels of IgG antibody bound HSV-2$^+$ cells and UI cells ($HSV_{MFI}$=6,510; $UI_{MFI}$=7,970; FIG. 1C). In contrast, when cell suspensions were incubated with a 1:6,000 dilution of HSV-2 antiserum, the level of antibody bound to HSV-2$^+$ cells was much higher than UI cells ($HSV_{MFI}$=608,180; $UI_{MFI}$=29,420; FIG. 1D).

Mouse serum levels of "pan-HSV-2 IgG" antibody were estimated based on the difference in mean fluorescence intensity (ΔMFI) between HSV-2$^+$ cells versus UI cells. The resulting ΔMFI-value associated with each serum sample was normalized to a "fold-increase above background" by the following calculation: $\Delta MFI_{test\ sample}$÷average $\Delta MFI_{naïve\ sera}$. When this approach was applied, sera from n=6 naïve mice were estimated to possess pan-HSV-2 IgG levels that were 1.0±0.2 times background (FIG. 1E). In contrast, n=6 mice immunized with a live-attenuated HSV-2 0ΔNLS virus [Halford et al., 2011] possessed levels of pan-HSV-2 IgG that were 940±240 times background (FIG. 1E). Therefore, flow cytometry of antibody-stained HSV-2$^+$ versus UI cells provided a potential means to measure pan-HSV-2 IgG abundance in the serum of vaccinated animals.

Comparison of Methods for Enumerating Serum Levels of HSV-2-Specific Antibody

Flow cytometry-based measurements of pan-HSV-2 IgG abundance were compared to two more traditional assays; namely, a HSV-2 neutralization assay and an antibody-capture ELISA. For this comparison, an antiserum dilution series was constructed by diluting mouse HSV-2 antiserum into naïve serum in 0.33-log increments spanning a 4,640-fold range. The use of naïve mouse serum as a diluent ensured that serum protein concentration (e.g., IgG) remained constant while HSV-2 specific antibodies were selectively diluted out in 0.33-log increments.

Figure 8:
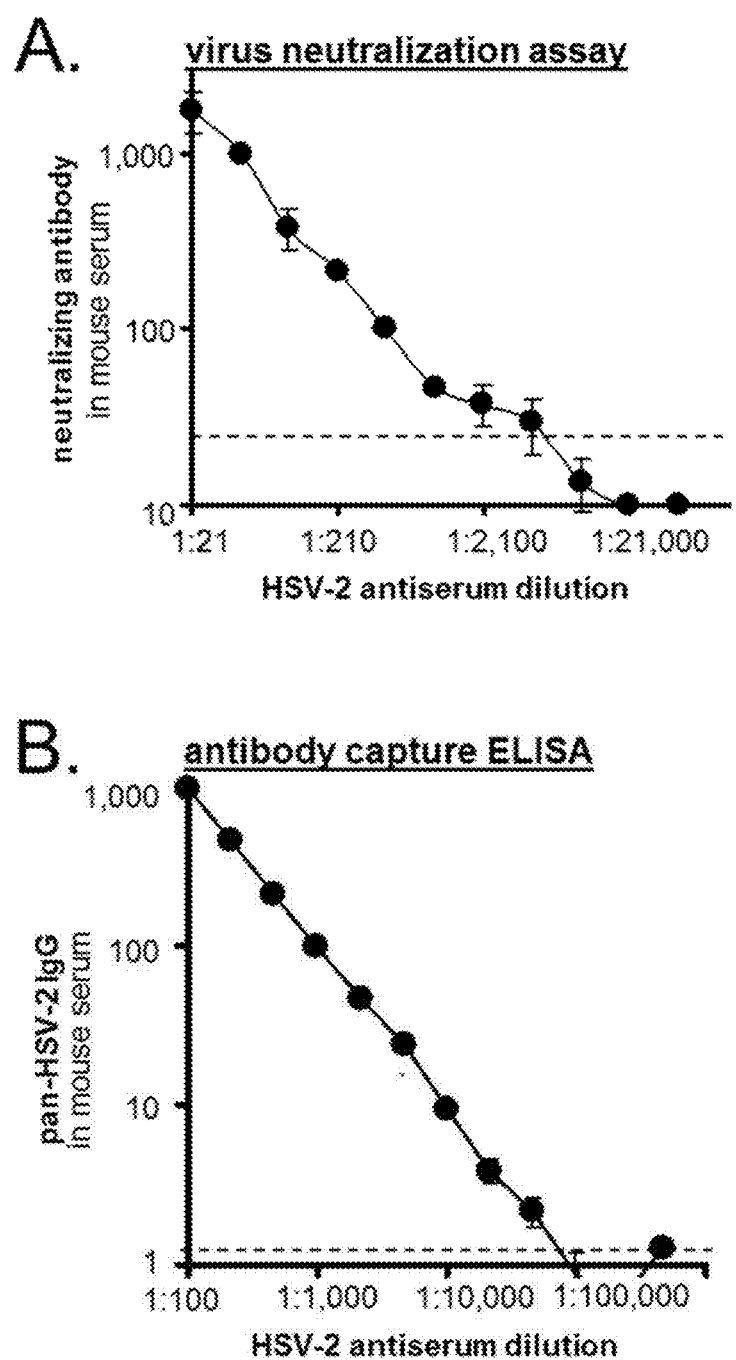
FIG. 8 shows a comparison of three methods to measure anti-HSV-2 antibody levels.
Figure 8:
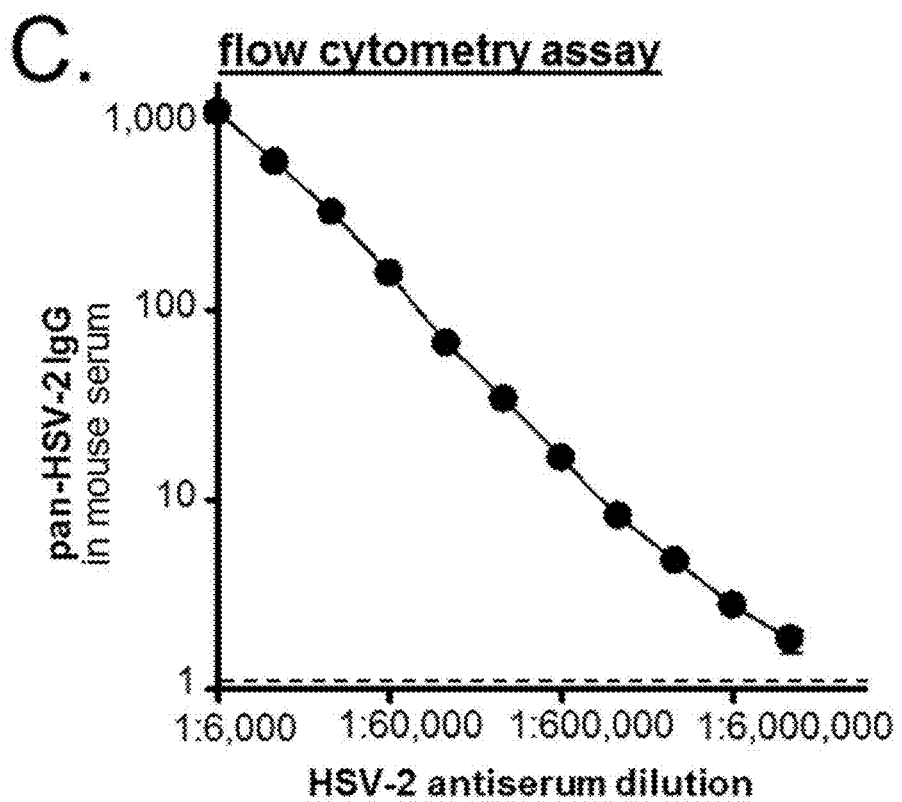

HSV-2 antiserum neutralized the infectivity of HSV-2 between dilutions of 1:21 and 1:1,000, and exhibited little to no neutralizing activity at 1:2,150 or greater dilutions (FIG. 8A). Thus, the dynamic range of the HSV-2 neutralization assay was 1:21 to 1:1,000, and the coefficient of variation of measurements was 16±8% within this range (FIG. 6).

HSV-2 antibody abundance in the antiserum dilution series was evaluated by antibody-capture ELISA using lysates of HSV-2-infected Vero cells as a coating antigen. Antibody capture-ELISA yielded significant conversion of para-nitrophenylphosphate substrate ($OD_{405}$) at serum dilutions between 1:100 and 1:100,000 (FIG. 8B). In this linear range, the coefficient of variation of ELISA-based measurement of pan-HSV-2 IgG levels was 13±3% (FIG. 6).

HSV-2 antibody abundance in the antiserum dilution series was evaluated by a novel, flow cytometry-based assay (FIG. 1). Flow cytometry of serum-stained test cells yielded a significant ΔMFI of IgG antibody-binding to HSV-2$^+$ cells versus UI cells between 1:6,000 and 1:6,000,000 dilutions of antiserum (FIG. 8C). In this linear range, the coefficient of variation of flow cytometry-based measurements of pan-HSV-2 IgG levels was 5±1% (FIG. 6).

All three assays yielded parallel estimates of pan-HSV-2 antibody abundance, but the flow cytometry-based assay was the most sensitive. Specifically, the flow assay had a lower limit-of-detection of 1:6,000,000 relative to HSV-2 antiserum, whereas the HSV-2 neutralization assay and antibody-capture ELISA had lower limits of 1:2,100 and 1:100,000, respectively (FIG. 6). In addition, the flow cytometry-based assay was the most precise, and exhibited a 2- to 3-fold lower coefficient of variation relative to the other assays (FIG. 6). Finally, the flow cytometry-based assay was unique in that the primary metric, ΔMFI, represented the average IgG antibody binding to 25,000 HSV-2$^+$ cells versus about 50,000 background control cells. This extensive replication in measurements accounted for the increased precision of the flow cytometry-based method.

Pan-HSV-2 IgG Correlates with Protection Against Ocular HSV-2 Challenge in Mice

Figure 5:
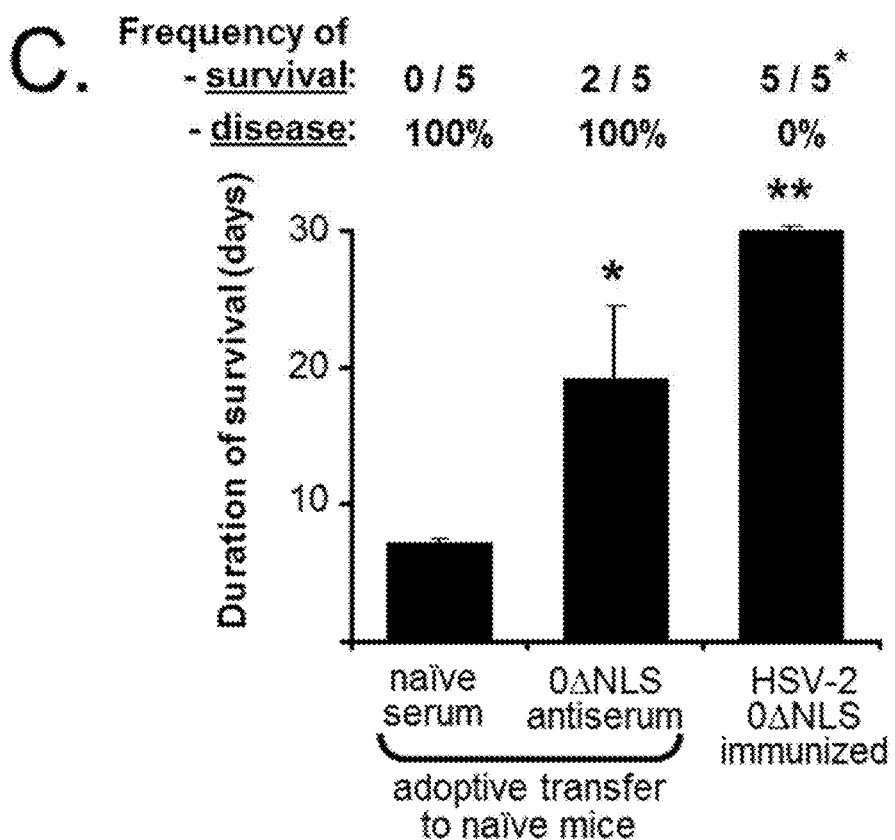
FIG. 5 shows that adoptive transfer of HSV-2 antiserum provides limited protection against ocular HSV-2 MS challenge. Female, age-matched strain 129 mice received either: 1) an adoptive transfer of 0.25 ml naïve serum prior to challenge; 2) an adoptive transfer of 0.25 ml HSV-2 antiserum just prior to challenge; or 3) active immunization with the live HSV-2 0ΔNLS virus 90 and 60 days prior to challenge. Mice were challenged in both eyes with 100,000 pfu per eye of HSV-2 MS, and challenge virus shedding and disease onset were recorded.

A retrospective analysis was performed on n=48 serum samples derived from mice used in a previously published ocular HSV-2 challenge experiment (FIGS. 5 and 6 in Halford et al., 2010). The goal of this analysis was to determine if pan-HSV-2 IgG levels in archived sera varied in proportion to the protection observed in mice ocularly challenged with HSV-2.

The design of the original experiment is reviewed. Five of 6 groups of mice were inoculated in the right eye with culture medium (naïve controls) or 100,000 pfu per right eye of the HSV-2 $ICP0^-$ mutant viruses HSV-2 0ΔNLS, 0Δ810, 0Δ254, or 0ΔRING (FIG. 2A). A sixth group was similarly inoculated with wild-type HSV-2 MS, but the pathogenesis of infection was restrained by treating mice with acyclovir (FIG. 2A). Blood was drawn on Day 60, and mice were challenged on Day 70 with 100,000 pfu per left eye of HSV-2 MS (FIG. 2A). The left eyes of these mice were swabbed daily between Days 1 and 3 post-challenge to monitor viral replication, and disease onset was observed over a 30 day-period (FIG. 2A).

Pre-challenge levels of pan-HSV-2 IgG in the immunization groups were determined and rank-ordered (FIG. 2B). Mice immunized with the HSV-2 0Δ810, 0Δ254, or 0ΔRING viruses possessed low to intermediate levels of pan-HSV-2 IgG that were an average 5- to 23-fold above background (FIG. 2B). In contrast, mice immunized with HSV-2 0ΔNLS or acyclovir-restrained HSV-2 MS possessed pan-HSV-2 IgG levels that were an average 110- and 290-fold above background, respectively (FIG. 2B).

Regression analysis was applied to determine if pre-challenge pan-HSV-2 IgG levels correlated with reduced HSV-2 shedding after ocular challenge. The null hypothesis predicted that the best-fit linear regression model (y=b+mx) for these 48 matched datum pairs would have a slope (m) of 0 (FIG. 2C). The probability that this null hypothesis was correct was $p<10^{-11}$. Rather, HSV-2 challenge virus shedding (y-variable) decreased an average 0.56 logarithms for every 1 logarithm that pan-HSV-2 IgG levels (x-variable) increased (black line in FIG. 2C).

The goodness-of-fit ($r^2$) value for the best-fit linear regression model was 0.65, which reflected the fact that the observed level of HSV-2 shedding in many mice did not conform perfectly to the quantity predicted by the equation y=3.35–0.56x (black line in FIG. 2C). However, the average level of ocular HSV-2 shedding decreased in direct proportion to pan-HSV-2 IgG levels in 5 of 6 immunization groups, within the standard error of the measurements (FIG. 2D; $r^2$=0.86). The exception to this trend was mice immunized with the HSV-2 0Δ254 virus, which elicited highly variable protection against HSV-2, and was thus rapidly eliminated from consideration as a viable live HSV-2 vaccine candidate [Halford et al., 2010].

The frequency with which immunized mice survived ocular HSV-2 challenge was plotted as a function of pre-challenge pan-HSV-2 IgG levels (FIG. 2E). Naïve mice had undetectable levels of pan-HSV-2 IgG, and none survived HSV-2 challenge (FIG. 2E). Mice immunized with HSV-2 0Δ810 or HSV-2 0Δ254 had the lowest levels of pan-HSV-2 IgG, and only 3 of 8 (43%) per group survived HSV-2 challenge (FIG. 2E). Mice immunized with HSV-2 0ΔRING had intermediate pan-HSV-2 IgG levels, and 5 of 8 survived HSV-2 challenge (FIG. 2E). Mice immunized with HSV-2 0ΔNLS or acyclovir-restrained MS had the highest pre-challenge levels of pan-HSV-2 IgG, and 100% survived ocular HSV-2 challenge (FIG. 2E). Collectively, these results indicated that pre-challenge pan-HSV-2 IgG levels correlated with vaccine-induced protection against HSV-2 in terms of: 1) reduced ocular shedding of the HSV-2 challenge virus; and 2) increased survival frequency.

ELISA Versus Flow Cytometry Estimates of Pan-HSV-2 IgG Levels

A test was conducted to determine if flow cytometry measurement of pan-HSV-2 IgG levels offered any practical advantage relative to antibody-capture ELISA. To this end, the same mouse serum samples considered above were re-analyzed by antibody-capture ELISA using HSV-2-infected cell lysates as coating antigen. A 0.33-log dilution series of HSV-2 antiserum was used to precisely define the sigmoidal relationship between $OD_{405}$ absorbance values and log (pan-HSV-2 IgG) levels using a hyperbolic tangent equation (FIG. 9A; $r^2$=1.00). Estimates of log (pan-HSV-2 IgG) levels for each serum sample were mathematically derived by fitting each serum sample's $OD_{405}$ absorbance values to this standard curve.

ELISA-based estimates of log (pan-HSV-2 IgG) correlated with decreased ocular HSV-2 shedding (black line in FIG. 9B; $r^2$=0.54). However, the goodness-of-fit of ELISA estimates of pan-HSV-2 IgG was less robust than the equivalent correlation with flow cytometry estimates of pan-HSV-2 IgG (FIG. 2C; $r^2$=0.65). In part, this was due to the 2.5-fold higher variance of ELISA-versus flow cytometry-based estimates of pan-HSV-2 IgG (FIG. 6).

The relative sensitivity of ELISA versus flow cytometry estimates of pan-HSV-2 IgG was graphically analyzed. ELISA estimates of log (pan-HSV-2 IgG) were plotted on the x-axis, whereas the corresponding flow cytometry estimates were plotted on the y-axis (FIG. 9C). If ELISA-versus flow cytometry-estimates were equally sensitive, then these n=48 datum points should graphically scatter around a '0 log' line-of-equivalence (FIG. 9C). However, 35 of 36 seropositive samples fell above the line-of-equivalence suggesting that flow cytometry yielded higher estimates of log (pan-HSV-2 IgG) than ELISA. In 6 of the 36 seropositive samples, flow cytometry yielded a more than +1 log-higher estimate of pan-HSV-2 IgG relative to ELISA (FIG. 9C). In these n=36 seropositive samples, flow cytometry yielded an average 5±1-fold higher estimate of pan-HSV-2 IgG level relative to ELISA. At the two extremes of pan-HSV-2 IgG levels, datum points clustered near the line of equivalence (FIG. 9C). However, in the low- to mid-range of sensitivity, the flow-cytometry assay was more sensitive than ELISA ($p<0.01$ for HSV-2 0ΔNLS, 0Δ810, 0Δ254, or 0ΔRING; paired t-test). Based on this and earlier analyses (FIG. 6), it was concluded that flow cytometry and ELISA yielded parallel estimates of pan-HSV-2 IgG levels, but the flow cytometry method offered improved precision and sensitivity.

Pan-HSV-2 IgG Correlates with Protection Against Vaginal HSV-2 Challenge in Mice A second, retrospective analysis was performed on mouse serum derived from a previously published experiment (FIG. 4 in Halford et al., 2011). The goal of this analysis was to determine if pan-HSV-2 IgG levels in archived sera varied in proportion to the protection observed in mice vaginally challenged with HSV-2.

The design of the original experiment is reviewed. Mice were immunized on Days 0 and 30 in their right and left rear footpads, respectively, with: 1) culture medium (naïve controls); 2) 2.5 μg green fluorescent protein (GFP) adjuvanted with alum and 10 μg MPL; 3) 2.5 μg $gD\text{-}2_{306t}$ [Nicola et al., 1996] adjuvanted with alum and 10 μg MPL; 4) $10^6$ pfu HSV-2 0ΔNLS; or 5) $10^6$ pfu wild-type HSV-2 MS where acyclovir was used to limit the pathogenesis of the primary exposure to MS (FIG. 3A; n=10 per group). Blood was drawn on Day 60 and mice were challenged on Days 90 or 100 with 500,000 pfu per vagina of HSV-2 MS. All n=50 mice were swabbed between Days 1 and 7 post-challenge to measure vaginal HSV-2 shedding and disease onset was observed over a 30 day-period (FIG. 3A).

Pan-HSV-2 IgG levels in the immunization groups were determined and rank-ordered (FIG. 3B). Naïve and GFP-immunized mice did not possess detectable pan-HSV-2 IgG, and none of these mice survived vaginal HSV-2 challenge (FIG. 3B). Mice immunized with gD-2 possessed pan-HSV-2 IgG that was an average 10-fold above background, and 1 of 10 survived vaginal HSV-2 challenge (FIG. 3B). Importantly, anti-gD-2-titers in gD-2-immunized mice were ~200,000 (FIG. 3C of Halford et al., 2011), which is comparable to other published studies [Bernstein et al., 2010; Bourne et al., 2005; Bourne et al., 2003]. Mice immunized with the live HSV-2 viruses MS or 0ΔNLS possessed pre-challenge pan-HSV-2 IgG levels that were an average 390- and 650-fold above background, respectively; 100% of these mice survived vaginal HSV-2 challenge without visible symptoms of disease (FIG. 3B).

Regression analysis was applied to determine if pre-challenge pan-HSV-2 IgG levels correlated with reduced HSV-2 shedding after vaginal challenge. The null hypothesis predicted that the best-fit linear regression model for these 50 matched datum pairs would have a slope (m) of 0 (FIG. 3C). The probability that this null hypothesis was correct was $p<10^{-14}$. Rather, HSV-2 challenge virus shedding (y) decreased an average 0.76 logarithms for every 1 logarithm that pan-HSV-2 IgG levels (x) increased (black line in FIG. 3C). The goodness-of-fit ($r^2$) for this regression line was 0.73, which reflected the fact that the observed level of HSV-2 shedding in many mice did not conform perfectly to the quantity predicted by the equation y=3.85−0.76x (black line in FIG. 3C). However, the average level of vaginal HSV-2 shedding decreased in direct proportion to pan-HSV-2 IgG levels in all 5 immunization groups within the standard error of the measurements (FIG. 3D; $r^2$=0.98). Therefore, pre-challenge pan-HSV-2 IgG levels correlated with vaccine-induced protection against HSV-2 in mice in terms of: 1) reduced vaginal shedding of the HSV-2 challenge virus; and 2) increased survival frequency.

Pan-HSV-2 IgG Correlates with Protection Against Vaginal HSV-2 Challenge in Guinea Pigs A third, prospective analysis was performed to determine if pre-challenge pan-HSV-2 IgG levels varied in proportion to protection against HSV-2 in a species other than mice. To address this question, groups of n=5 guinea pigs were immunized on Days 0 and 30 in their right and left rear footpads, respectively, with: 1) culture medium (naïve); 2) 5 μg gD-2 adjuvanted with alum and 20 μg MPL; 3) 2×10⁶ pfu HSV-2 0ΔNLS; or 4) 2×10⁶ pfu of wild-type HSV-2 MS where acyclovir was used to restrict the pathogenesis of the primary exposure to MS (FIG. 4A). Guinea pigs were bled on Day 75 and challenged on Day 90 with 2×10⁶ pfu HSV-2 MS per vagina (FIG. 4A). Unfortunately, one gD-2-immunized guinea pig was lost to an anesthetic overdose; thus, only n=4 gD-2-immunized guinea pigs were available following HSV-2 vaginal challenge. Naïve guinea pigs shed peak titers of about 200,000 pfu per vagina on Day 2 post-challenge (FIG. 4B). Guinea pigs immunized with gD-2 shed an average 5-fold less HSV-2 relative to naïve guinea pigs between Days 1 and 8 post-challenge (FIG. 4B). In contrast, guinea pigs immunized with HSV-2 MS or 0ΔNLS shed an average 150- and 200-fold less HSV-2, respectively, relative to naïve guinea pigs (FIG. 4B).

Regression analysis was applied to determine if pre-challenge pan-HSV-2 IgG levels in guinea pigs correlated with reduced HSV-2 shedding after vaginal challenge. The null hypothesis predicted that the best-fit linear regression model for these n=19 matched datum pairs would have a slope (m) of 0 (FIG. 4C). The probability that this null hypothesis was correct was $p<10^{-7}$. Rather, HSV-2 challenge virus shedding (y) decreased an average 0.95 logarithms for every 1 logarithm that pan-HSV-2 IgG levels (x) increased (black line in FIG. 4C). The goodness-of-fit ($r^2$) for this regression line was 0.85, which reflected the fact that the observed level of HSV-2 shedding in many guinea pigs did not conform perfectly to the quantity predicted by the equation y=3.77−0.95x (FIG. 4C). However, the average level of vaginal HSV-2 shedding decreased in direct proportion to pan-HSV-2 IgG levels in all four immunization groups, within the standard error of the measurements (FIG. 4D; $r^2$=0.98).

Regarding disease progression, naïve guinea pigs uniformly developed florid perivaginal disease and had to be sacrificed on or before Day 11 post-challenge (FIG. 4E). Guinea pigs immunized with gD-2 possessed low pan-HSV-2 IgG levels, and three of four developed florid perivaginal disease that required their sacrifice on or before Day 11 post-challenge (FIG. 4E). In contrast, guinea pigs immunized with the live HSV-2 viruses MS or 0ΔNLS possessed high pre-challenge pan-HSV-2 IgG levels, and 100% of these guinea pigs survived vaginal HSV-2 challenge without developing any visible symptoms of disease (FIG. 4E).

The results of vaginal HSV-2 challenge experiments in mice and guinea pigs was compared (FIG. 7). In both species, immunization with gD-2 elicited a significant increase in pan-HSV-2 IgG that was an average 10- to 20-fold above background, and which correlated with partial protection against vaginal HSV-2 challenge (FIG. 7). In contrast, mice or guinea pigs immunized with the live HSV-2 viruses MS or 0ΔNLS mounted pan-HSV-2 IgG antibody responses that were 30- to 40-fold greater than gD-2 immunized animals (FIG. 7). Likewise, mice or guinea pigs immunized with MS or 0ΔNLS shed an average 20- to 35-fold less HSV-2 per vagina relative to gD-2 immunized animals (FIG. 7). Collectively, these results indicated that increased pan-HSV-2 IgG levels in immunized mice and guinea pigs correlated with increased vaccine-induced protection against HSV-2 in terms of: 1) reduced vaginal shedding of the HSV-2 challenge virus; and 2) increased survival frequency.

HSV-2 Antiserum Alone Offers Weak Protection Against HSV-2 MS Challenge

High levels of pan-HSV-2 IgG antibodies correlated with robust protection against HSV-2 MS challenge in mice immunized with several live HSV-2 vaccines. A final experiment was conducted to determine if adoptive transfer of HSV-2 antiserum recapitulated the level of protection against HSV-2 observed in mice immunized with the HSV-2 0ΔNLS virus.

To this end, strain 129 mice (n=10) were immunized in their right and left rear footpads with 10⁶ pfu of HSV-2 0ΔNLS on Days 0 and 30, respectively. On Day 85, five immunized mice were sacrificed to collect HSV-2 antiserum, and naïve serum was harvested at this time from age-matched controls. On Day 90, naïve mice received an adoptive transfer of 0.25 ml pooled naïve serum or HSV-2 antiserum (n=5 per group), and were then challenged with 100,000 pfu per eye of HSV-2 MS. Likewise, n=5 mice immunized with HSV-2 0ΔNLS were also challenged with 100,000 pfu per eye of HSV-2 MS.

Ocular shedding of HSV-2 MS was compared. On Day 1 post-challenge, mice treated with naïve serum shed an average 3,000 per eye of HSV-2 MS, whereas mice treated with HSV-2 antiserum shed an average 16-fold less HSV-2 and this difference was significant (FIG. 5A). However, HSV-2 antiserum-treated mice and naïve serum-treated mice shed high and equivalent levels of HSV-2 on Day 3 post-ocular challenge (FIG. 5B). In contrast, mice immunized with HSV-2 0ΔNLS shed an average 300- and 60-fold less HSV-2 MS on Days 1 and 3, respectively, relative to naïve serum-treated mice (FIGS. 5A and 5B).

Adoptive transfer of HSV-2 antiserum delayed, but did not prevent, the progression of HSV-2-induced pathogenesis. Specifically, 100% of naïve serum-treated mice succumbed to ocular HSV-2 challenge on Days 7 or 8 post-challenge (FIG. 5C).

Two of 5 HSV-2 antiserum-treated mice survived ocular HSV-2 challenge, and as a group these mice survived for 19±5 days post-challenge (FIG. 5C). Although mice treated with HSV-2 antiserum survived significantly longer, these animals were not well protected.

Specifically, 100% of HSV-2 antiserum-treated mice developed overt periocular fur loss and disease between Days 10 and 14 post-challenge, and 60% of these mice succumbed to challenge (FIG. 5C). In contrast, 100% of HSV-2 0ΔNLS-immunized mice survived without any overt signs of disease for 30 days post-challenge (FIG. 5C). Therefore, although pan-HSV-2 IgG antibody levels correlated with vaccine-induced protection against HSV-2 (FIGS. 2, 3, and 4), it is unlikely than anti-HSV-2 antibodies alone were the sole mediators of vaccine-induced protection against HSV-2 challenge.

Discussion

General Discussion

The current study demonstrates that bloodstream levels of pan-HSV-2 IgG antibody in vaccinated mice and guinea pigs correlated with protection against HSV-2. It has not been determined in this study if other components of the adaptive immune response would also correlate with vaccine-induced protection against HSV-2. For example, HSV-2-specific T-cell frequency [Laing et al., 2010; St leger et al., 2011; Posavad et al., 2010] or anti-HSV-2 IgA abundance in the vaginal mucosa [Tirabassi et al., 2011] may provide better correlates of immunity for a HSV-2 vaccine. However, it should be noted that the utility of a correlate of immunity is not dependent on its role in mediating protection. Rather, a correlate of immunity is a screening tool whose utility lies solely in its ability to gauge the magnitude of vaccine-induced protection against a microbial pathogen. It remains to be determined if pan-HSV-2 IgG levels would be useful in gauging HSV-2 vaccine efficacy in human clinical trials.

Relevance of Humoral Versus Cellular Immunity in Vaccine-Induced Protection Against HSV-2

The relevance of humoral versus cell-mediated immunity in vaccine-induced protection against HSV-2 remains incompletely defined. What is evident from decades of studies dating back to Oakes, 1975 is that adoptively transferred anti-HSV antibodies or B-cells alone are not sufficient to prevent peripheral HSV-1 infection from progressing to fatal disease in immunodeficient nude or SCID mice [Nagafuchi et al., 1979; Halford et al., 2005b]; whereas, adoptively transferred T-cells are sufficient to allow immunodeficient animals to survive peripheral infection with low virulence strains of HSV-1 [Nagafuchi et al., 1979; Halford et al., 2005b]. Moreover, T-cells play a direct role in controlling HSV-1 and HSV-2 infections in sensory ganglia [Divito et al., 2006; Khanna et al., 2003; Knickelbein et al., 2008; Theil et al., 2003; Liu et al., 2000; Simmons and Tscharke, 1992; Zhu et al., 2007]. Thus, vaccine-induced protection against HSV-2 will almost certainly be dependent upon the T-cell response to HSV-2 antigens [Koelle and Corey, 2008; Johnston et al., 2012; Laing et al., 2012; Dudek and Knipe, 2006; Morrison, 2002].

Complete, vaccine-induced protection against HSV-2 genital herpes lesions will most likely be dependent upon a balanced B-cell (antibody) and T-cell response to HSV-2's antigens. Two lines of evidence support this hypothesis. First, SCID mice reconstituted with both B- and T-cells control HSV-1 infection significantly more rapidly than SCID mice reconstituted with T-cells alone (FIG. 1C in Halford et al., 2005b); numerous investigators have reported similar findings with HSV-1 or HSV-2 [Morrison et al., 2001; Chu et al., 2008; Staats et al., 1991]. Second, T-cells alone are slow to infiltrate sites of HSV-1 or HSV-2 challenge unless chemokines [Shin and Iwasaki, 2012] or inflammatory stimuli [Mackay et al., 2012] are used to artificially increase the rate of T-cell recruitment. In contrast, antibodies are ~100 billion-fold smaller than T-cells, and may rapidly enter virus-infected tissues; hence, antibodies may act during the first 24 hours to restrict HSV-2 replication and/or spread (FIG. 5A).

Against this background, a logical function for anti-HSV-2 antibodies would be to serve as the first line of adaptive immune defense that triggers the pro-inflammatory events (e.g., complement cascade) that promote the rapid recruitment of T-cells into virus-infected tissues at the portal of HSV-2 entry (e.g., the vagina).

Correlates of Immunity to HSV-2: Current Study Versus Earlier Findings

Previous attempts to identify correlates of immunity to HSV-2 have focused on immune responses to the immunogens under study; namely, gB and/or gD [Shlapobersky et al., 2012; Bernstein et al., 2010; Bourne et al., 2005; Bernstein, 2005; Bourne et al., 2003; Khodai et al., 2011; Bernstein et al., 2011; Natuk et al., 2006; Chentoufi et al., 2010]. These approaches do not consider HSV-2's full complement of antigens. At least 20 viral proteins are known targets of the human B- and T-cell response to HSV-2 [Hosken et al., 2006; Laing et al., 2010; Gilman et al., 1981]. Such glycoprotein-focused studies have not adequately considered that viral antigens other than gB-2 and gD-2 may also contribute to immunity to HSV-2.

Glycoprotein-centric correlates of immunity suggest that gB-2 and/or gD-2 subunit vaccines should be sufficient to prevent HSV-2 genital herpes in humans [Bernstein et al., 2010; Bourne et al., 2005; Bernstein, 2005; Bourne et al., 2003]. This prediction has not been borne out by the data from human clinical trials spanning the last 23 years [Belshe et al., 2012; Stanberry et al., 2002; Straus et al., 1997; Corey et al., 1999; Straus et al., 1994; Mertz et al., 1990]. The pan-HSV-2 IgG metric is a more realistic correlate of immunity because it weighs the relative abundance of IgG antibodies against all of HSV-2's antigens, and thus is not contingent upon an assumption that the immune response to 1 or 2 specific proteins will necessarily provide an accurate gauge of immunity to HSV-2.

The results of the current two cell study demonstrate that immunization with a gD-2 vaccine elicits a significant pan-HSV-2 IgG antibody response and a significant reduction in vaginal HSV-2 shedding (FIG. 7). However, animals immunized with polyvalent HSV-2 viruses mount an about 30-fold greater pan-HSV-2 IgG response than gD-2-immunized animals, and likewise exhibit about 25-fold lower vaginal HSV-2 shedding after challenge (FIG. 7). These results raise the possibility that, in addition to gD-2, immune responses directed against HSV-2's other 20 antigens may also contribute to the protective efficacy of a live HSV-2 vaccine.

Use of Regression Analysis to Detect a Correlate of Immunity to HSV-2

Several HSV-2 vaccine-challenge studies have attempted to measure protection against HSV-2 in terms of disease scores, survival, or weight gain after HSV-2 challenge [Khodai et al., 2011; McClements et al., 1996; Pyles et al., 2002]. Non-parametric statistics (i.e., disease and survival) or tangential parameters (i.e., weight gain) are likely weak measures of the primary variable under study, protection against HSV-2. In contrast, reductions in HSV-2 challenge virus shedding are a precise measure of protection against HSV-2, and vary over an about 500-fold range. The use of this robust measure of protection allowed linear regression analysis to be applied in the current study to determine if increased pan-HSV-2 IgG levels (x) correlated with protection against HSV-2 (y), as gauged by reductions in ocular or vaginal HSV-2 shedding (FIGS. 2C, 3C, and 4C).

Linear regression analysis is one of the most powerful statistical tools available to determine if a correlation exists between two variables. It is believed that the current study is the first to apply regression analysis to detect a correlation between a parameter of the adaptive immune response and protection against HSV-2. This innovation was critical to the success of the current study. The ability to detect a correlation between two parameters by regression analysis is dependent on three variables. Variable 1 is the number of matched x, y datum pairs in the data set. Variable 2 is the precision of measurements of the x- and y-variables. Variable 3 is the range of Δx and Δy over which a correlation may be observed.

Regarding Variable 2, the flow cytometric assay introduced herein improved the precision and sensitivity of estimates of pan-HSV-2 IgG levels (FIGS. 6 and 9C), and thus improved the $r^2$-value of the correlation relatie to antibody-capture ELISA. This technical innovation enhanced the ability to detect a correlation between pan-HSV-2 IgG (x-variable) and reductions in HSV-2 challenge Nirus shedding (y-variable).

Regarding Variable 3, if the current study had focused exclusively on one vaccine modality such as the HSV-2 0ΔNLS vaccine, then the observed range of pan-HSV-2 IgG levels (Δx) would have been too narrow (about 5-fold) to detect a meaningful correlation (FIGS. 3C and 4C). However, by employing six HSV-2 immunogens in three independent challenge experiments, the study was able to expand the range of observed pan-HSV-2 IgG levels to an about 500-fold range (FIGS. 2C, 3C, and 4C). Thus, the success of the current study was highly dependent on the use of a total n=117 animals which collectively offered a 500-fold range of pan-HSV-2 IgG levels (Δx) over which the study could test for proportional decreases in HSV-2 challenge virus shedding (y).

CONCLUSION

The current studies illustrate that the disclosed demonstrates that in vaccinated mice and guinea pigs, the pan-HSV-2 IgG antibody response to several vaccines varies in proportion to protection against HSV-2. It is possible that this same approach may provide a useful screening tool in human clinical trials of a HSV-2 vaccine. Based on the results, a HSV-2 vaccine formulation that elicits the most potent and durable pan-HSV-2 IgG antibody response in humans should elicit the greatest protection against HSV-2 genital herpes. However, the proposed utility of pan-HSV-2 IgG as a potential correlate of vaccine-induced protection against HSV-2 remains to be tested in humans. Therefore, it will be of interest to test this prediction in coming years, and determine if pan-HSV-2 IgG levels provide a useful correlate of vaccine-induced protection against HSV-2 in humans.

Citations

Allen et al., (1990). Role of coexpression of IL-2 and herpes simplex virus proteins in recombinant vaccinia virus vectors on levels of induced immunity. *Viral Immunol* 3:207-215.

Belshe et al. (2012). Efficacy results of a trial of a herpes simplex vaccine. *N Engl J Med* 366:34-43.

Bernstein (2005). Glycoprotein D adjuvant herpes simplex virus vaccine. *Expert Rev Vaccines* 4:615-627.

Bernstein et al. (2010). The adjuvant CLDC increases protection of a herpes simplex type 2 glycoprotein D vaccine in guinea pigs. *Vaccine* 28:3748-3753.

Bernstein et al. (2011). Effects of herpes simplex virus type 2 glycoprotein vaccines and CLDC adjuvant on genital herpes infection in the guinea pig. *Vaccine* 29:2071-2078.

Bourne et al. (2003). Herpes simplex virus (HSV) type 2 glycoprotein D subunit vaccines and protection against genital HSV-1 or HSV-2 disease in guinea pigs. *J Infect Dis* 187:542-549.

Bourne et al. (2005). Impact of immunization with glycoprotein D2/AS04 on herpes simplex virus type 2 shedding into the genital tract in guinea pigs that become infected. *J Infect Dis* 192:2117-2123.

Brans et al. (2010). Immunization with a dominant-negative recombinant Herpes Simplex Virus (HSV) type 1 protects against HSV-2 genital disease in guinea pigs. *BMC Microbiology* 10:163.

CDC (2010). Seroprevalence of herpes simplex virus type 2 among persons aged 14-49 years—United States, 2005-2008. *MMWR Morb Mortal Wkly Rep* 59:456-459.

Chentoufi et al. (2010). A novel HLA (HLA-A*0201) transgenic rabbit model for preclinical evaluation of human CD8+ T cell epitope-based vaccines against ocular herpes. *J Immunol* 184:2561-2571.

Chu et al. (2008). Antibody-mediated protection against genital herpes simplex virus type 2 disease in mice by Fc gamma receptor-dependent and -independent mechanisms. *J Reprod Immunol* 78:58-67.

Corey et al. (1999). Recombinant glycoprotein vaccine for the prevention of genital HSV-2 infection: two randomized controlled trials. Chiron HSV Vaccine Study Group. *JAMA* 282:331-340.

Corey et al. (2004). Once-daily valacyclovir to reduce the risk of transmission of genital herpes. *N Engl J Med* 350:11-20.

DeJesus et al. (2003). Valacyclovir for the suppression of recurrent genital herpes in human immunodeficiency virus-infected subjects. *J Infect Dis* 188:1009-1016.

Divito et al. (2006). A triple entente: virus, neurons, and CD8+ T cells maintain HSV-1 latency. *Immunol Res* 36:119-126.

Dudek et al. (2006). Replication-defective viruses as vaccines and vaccine vectors. *Virology* 344:230-239.

Eo et al. (2001). Prime-boost immunization with DNA vaccine: mucosal route of administration changes the rules. *J Immunol* 166:5473-5479.

Gilman et al. (1981). Antibody responses in humans to individual proteins of herpes simplex viruses. *Infect Immun* 34:880-887.

Golden et al. (2005). HSV-2 Western blot confirmatory testing among men testing positive for HSV-2 using the focus enzyme-linked immunosorbent assay in a sexually transmitted disease clinic. *Sex Transm Dis* 32:771-777.

Gupta et al. (2007). Genital herpes. *Lancet* 370:2127-2137.

Halford et al. (2005a). Mathematical analysis demonstrates that interferons-beta and -gamma interact in a multiplicative manner to disrupt herpes simplex virus replication. *J Theor Biol* 235:439-454.

Halford et al. (2005b). Re-evaluating the role of natural killer cells in innate resistance to herpes simplex virus type 1. *Virol J* 2:56.

Halford et al. (2010). Herpes simplex virus 2 ICP0 mutant viruses are avirulent and immunogenic: implications for a genital herpes vaccine. *PLoS ONE* 5:e12251.

Halford et al. (2011). A live-attenuated HSV-2 ICP0 virus elicits 10 to 100 times greater protection against genital herpes than a glycoprotein D subunit vaccine. *PLoS ONE* 6:e17748.

Halford et al. (2013). Pan-HSV-2 IgG antibody in vaccinated mice and guinea pigs correlates with protection against herpes simplex virus 2. *PLoS ONE.* 8:e65523.

Handsfield et al. (2007). Suppressive therapy with valacyclovir in early genital herpes: a pilot study of clinical efficacy and herpes-related quality of life. *Sex Transm Dis* 34:339-343.

Hoskin et al. (2006). Diversity of the CD8+ T-cell response to herpes simplex virus type 2 proteins among persons with genital herpes. *J Virol* 80:5509-5515.

Johnston et al. (2012). HSV-2: in pursuit of a vaccine. *J Clin Invest* 121:4600-4609.

Karem et al. (1997). Protective immunity against herpes simplex virus (HSV) type 1 following oral administration of recombinant *Salmonella typhimurium* vaccine strains expressing HSV antigens. *J Gen Virol* 78(Pt 2):427-434.

Khanna et al. (2003). Herpes simplex virus-specific memory CD8(+) T cells are selectively activated and retained in latently infected sensory ganglia. *Immunity* 18:593-603.

Khodai et al. (2011). Single and combination herpes simplex virus type 2 glycoprotein vaccines adjuvanted with CpG oligodeoxynucleotides or monophosphoryl lipid A exhibit differential immunity that is not correlated to protection in animal models. *Clin Vaccine Immunol* 18:1702-1709.

Knickelbein et al. (2008). Noncytotoxic lytic granule-mediated CD8+ T cell inhibition of HSV-1 reactivation from neuronal latency. *Science* 322:268-271.

Koelle et al. (2008). Herpes simplex: insights on pathogenesis and possible vaccines. *Annu Rev Med* 59:381-395.

Kuklin et al. (1997). Induction of mucosal immunity against herpes simplex virus by plasmid DNA immunization. *J Virol* 71:3138-3145.

Laing et al. (2010). Diversity in CD8(+) T cell function and epitope breadth among persons with genital herpes. *J Clin Immunol* 30:703-722.

Laing et al. (2012). Immunology in the Clinic Review Series; focus on host responses: T cell responses to herpes simplex viruses. *Clin Exp Immunol* 167:47-58.

Lingappa et al. (2007). Clinical and therapeutic issues for herpes simplex virus-2 and HIV co-infection. *Drugs* 67:155-174.

Liu et al. (2000). CD8(+) T cells can block herpes simplex virus type 1 (HSV-1) reactivation from latency in sensory neurons. *J Exp Med* 191:1459-1466.

Mackay et al. (2012). Long-lived epithelial immunity by tissue-resident memory T (TRM) cells in the absence of persisting local antigen presentation. *Proc Natl Acad Sci USA* 109:7037-7042.

Manickan et al. (1995). Vaccination with recombinant vaccinia viruses expressing ICP27 induces protective immunity against herpes simplex virus through CD4+ Th1+ T cells. *J Virol* 69:4711-4716.

McClements et al. (1996). Immunization with DNA vaccines encoding glycoprotein D or glycoprotein B, alone or in combination, induces protective immunity in animal models of herpes simplex virus-2 disease. *Proc Natl Acad Sci USA* 93:11414-11420.

Meignier et al. (1988). In vivo behavior of genetically engineered herpes simplex viruses R7017 and R7020: construction and evaluation in rodents. *J Infect Dis* 158:602-614.

Mertz et al. (1990). Double-blind, placebo-controlled trial of a herpes simplex virus type 2 glycoprotein vaccine in persons at high risk for genital herpes infection. *J Infect Dis* 161:653-660.

Morrison (2002). Vaccines against genital herpes: progress and limitations. *Drugs* 62:1119-1129.

Morrison et al. (2001). Vaccine-induced serum immunoglobin contributes to protection from herpes simplex virus type 2 genital infection in the presence of immune T cells. *J Virol* 75:1195-1204.

Nagafuchi et al. (1979). Mechanism of acquired resistance to herpes simplex virus infection as studied in nude mice. *J Gen Virol* 44:715-723.

Natuk et al. (2006). Recombinant vesicular stomatitis virus vectors expressing herpes simplex virus type 2 gD elicit robust CD4+ Th1 immune responses and are protective in mouse and guinea pig models of vaginal challenge. *J Virol* 80:4447-4457.

Ng'ayo et al. (2011). Performance of HSV-2 type specific serological tests in men in Kenya. *J Virol Methods* 163:276-281.

Nicola et al. (1996). Structure-function analysis of soluble forms of herpes simplex virus glycoprotein D. *J Virol* 70:3815-3822.

Norrild et al. (1981). Immunological reactivity of herpes simplex virus 1 and 2 polypeptides electrophoretically separated and transferred to diazobenzyloxymethyl paper. *Infect Immun* 31:660-667.

Oakes (1975). Role for cell-mediated immunity in the resistance of mice to subcutaneous herpes simplex virus infection. *Infect Immun* 12:166-172.

Orr et al. (2007). Cutting Edge: Recombinant *Listeria monocytogenes* expressing a single immune-dominant peptide confers protective immunity to herpes simplex virus-1 infection. *J Immunol* 178:4731-4735.

Paz-Bailey et al. (2007). Herpes simplex virus type 2: epidemiology and management options in developing countries. *Sex Transm Infect* 83:16-22.

Posavad et al. (2010). Detailed characterization of T cell responses to herpes simplex virus-2 in immune seronegative persons. *J Immunol* 184:3250-3259.

Preacher et al. (2001). Calculation for Fisher's Exact Test: An interactive calculation tool for Fisher's exact probability test for 2×2 tables. [Computer software]. Available from http://quantpsy.org.

Pyles et al. (2002). Use of immunostimulatory sequence-containing oligonucleotides as topical therapy for genital herpes simplex virus type 2 infection. *J Virol* 76:11387-11396.

Rana et al. (2006). Sexual behaviour and condom use among individuals with a history of symptomatic genital herpes. *Sex Transm Infect* 82:69-74.

Rattray et al. (1978). Recurrent genital herpes among women: symptomatic v. asymptomatic viral shedding. *Br J Vener Dis* 54:262-265.

Roizman et al. (1984). Identification and preliminary mapping with monoclonal antibodies of a herpes simplex virus 2 glycoprotein lacking a known type 1 counterpart. *Virology* 133:242-247.

Rouse et al. (2006). A tale of 2 alpha-herpesviruses: lessons for vaccinologists. *Clin Infect Dis* 42:810-817.

Samaniego et al. (1998). Persistence and expression of the herpes simplex virus genome in the absence of immediate-early proteins. *J Virol* 72:3307-3320.

Sanchez-Martinez et al. (1991). Evaluation of a test based on baculovirus-expressed glycoprotein G for detection of herpes simplex virus type-specific antibodies. *J Infect Dis* 164:1196-1199.

Shin et al. (2012). A vaccine strategy that protects against genital herpes by establishing local memory T cells. *Nature* 491:463-467.

Shlapobersky et al. (2012). Vaxfectin(R)-adjuvanted plasmid DNA vaccine improves protection and immunogenicity in a murine model of genital herpes infection. *J Gen Virol* 93:1305-1315.

Simmons et al. (1992). Anti-CD8 impairs clearance of herpes simplex virus from the nervous system: implications for the fate of virally infected neurons. *J Exp Med* 175:1337-1344.

Sperling et al. (2008). The effect of daily valacyclovir suppression on herpes simplex virus type 2 viral shedding in HSV-2 seropositive subjects without a history of genital herpes. *Sex Transm Dis* 35:286-290.

St Leger et al. (2011). Defining the herpes simplex virus-specific CD8+ T cell repertoire in C57BL/6 mice. *J Immunol* 186:3927-3933.

Staats et al. (1991). Anti-glycoprotein D monoclonal antibody protects against herpes simplex virus type 1-induced diseases in mice functionally depleted of selected T-cell subsets or asialo GM1+ cells. *J Virol* 65:6008-6014.

Stanberry et al. (2002). Glycoprotein-D-adjuvant vaccine to prevent genital herpes. *N Engl J Med* 347:1652-1661.

Straus et al. (1994). Placebo-controlled trial of vaccination with recombinant glycoprotein D of herpes simplex virus type 2 for immunotherapy of genital herpes. *Lancet* 343:1460-1463.

Straus et al. (1997). Immunotherapy of recurrent genital herpes with recombinant herpes simplex virus type 2 glycoprotein D and B: results of a placebo-controlled vaccine trial. *J Infect Dis* 176:1129-1134.

Theil et al. (2003). Latent herpesvirus infection in human trigeminal ganglia causes chronic immune response. *Am J Pathol* 163:2179-2184.

Tirabassi et al. (2011). A mucosal vaccination approach for herpes simplex virus type 2. *Vaccine* 29:1090-1098.

Tronstein et al. (2011). Genital shedding of herpes simplex virus among symptomatic and asymptomatic persons with HSV-2 infection. *JAMA* 305:1441-1449.

Vergidis et al. (2009). Meta-analytical studies on the epidemiology, prevention, and treatment of human immunodeficiency virus infection. *Infect Dis Clin North Am* 23:295-308.

Wald et al. (2000). Reactivation of genital herpes simplex virus type 2 infection in asymptomatic seropositive persons. *N Engl J Med* 342:844-850.

Wald et al. (2001). Effect of condoms on reducing the transmission of herpes simplex virus type 2 from men to women. *JAMA* 285:3100-3106.

Warren (2002). Getting tested for herpes. *FDA Consum* 36:40.

Warren et al. (2005). Counseling the patient who has genital herpes or genital human papillomavirus infection. *Infect Dis Clin North Am* 19:459-476.

Warren et al. (2011). Availability of serologic and virologic testing for herpes simplex virus in the largest sexually transmitted disease clinics in the United States. *Sex Transm Dis* 38:267-269.

Weir et al. (1989). Recombinant vaccinia virus expressing the herpes simplex virus type 1 glycoprotein C protects mice against herpes simplex virus challenge. *J Gen Virol* 70(Pt 10):2587-2594.

Whittington et al. (2001). Use of a glycoprotein G-based type-specific assay to detect antibodies to herpes simplex virus type 2 among persons attending sexually transmitted disease clinics. *Sex Transm Dis* 28:99-104.

Xu et al. (2006). Trends in herpes simplex virus type 1 and type 2 seroprevalence in the United States. *JAMA* 296:964-973.

Zhu et al. (2007). Virus-specific CD8+ T cells accumulate near sensory nerve endings in genital skin during subclinical HSV-2 reactivation. *J Exp Med* 204:595-603.

Each of the patents, patent applications and articles cited herein is incorporated by reference. The use of the article "a" or "an" is intended to include one or more.

Although several particular embodiments of the present serological assay have been described herein, it will be appreciated by those skilled in the art that changes and modifications may be made thereto without departing from the invention in its broader aspects and as set forth in the following claims.

What is claimed is:

1. A serological assay method for determining whether a subject is infected with one, both or neither of herpes simplex-1 (HSV-1) and herpes simplex-2 (HSV-2) viruses, comprising:
   a) individually admixing at least three serum subsamples obtained from a serum sample of the subject, wherein the serum sample comprises antibodies from the subject, with one of
      (i) cell antigens from cells uninfected with HSV-1 and HSV-2 immobilized on a physical matrix;
      (ii) cell antigens from HSV-1-infected cells immobilized on a physical matrix, and
      (iii) cell antigens from HSV-2-infected cells immobilized on a physical matrix,
   to form at least three serum subsample antibody-cell antigen admixtures, and maintaining each of said admixtures for a time period sufficient for the antibodies to bind to said cell antigens to form admixtures comprising matrix-bound antibodies and at least three preadsorbed serum subsamples comprising antibodies;
   b) removing the matrix-bound antibodies from the at least three preadsorbed serum subsamples comprising antibodies;

c) separately admixing each of said separated preadsorbed serum subsamples comprising antibodies with a mixture comprising three fixed and permeabilized cell populations including:
   (i) fixed and permeabilized cells uninfected by either HSV-1 or HSV-2;
   (ii) fixed and permeabilized cells infected by HSV-1; and
   (iii) fixed and permeabilized cells infected by HSV-2,
   and maintaining said admixtures for a time period sufficient to permit the antibodies present within each preadsorbed subsample to bind to the cell antigens on one or more of the fixed and permeabilized cell populations wherein the fixed and permeabilized cell populations are distinguishable from each other by fluorescence emissions when irradiated; and
d) measuring the amount of binding of the antibodies present within each preadsorbed subsample to the antigens in each of the fixed and permeabilized cell populations using flow cytometry to determine whether the subject was infected by one, both, or neither of HSV-1 and HSV-2.

2. The method according to claim 1, wherein the cell antigens immobilized on the physical matrix of a)(i), (ii) and (iii) comprise fixed and permeabilized uninfected cells, fixed and permeabilized HSV-1-infected cells, and fixed and permeabilized HSV-2-infected cells, respectively.

3. The method according to claim 1, wherein the fixed and permeabilized uninfected cells, fixed and permeabilized HSV-1-infected cells, and fixed and permeabilized HSV-2-infected cells are distinguishable from each other by fluorescence emission when irradiated with wavelengths of light that excite an exogenously-introduced fluorescent colorant.

4. The method according to claim 3, wherein the exogenously-introduced fluorescent colorant comprises a dye.

5. The method according to claim 3, wherein the exogenously-introduced fluorescent colorant comprises an intracellularly-expressed fluorescent protein.

6. The method according to claim 3, wherein said exogenously-introduced fluorescent colorant comprises an intracellularly-expressed protein.

7. The method according to claim 3, wherein said exogenously-introduced fluorescent colorant forms a covalent linkage with the cell antigens contained on the fixed and permeabilized cell.

8. The method according to claim 4, wherein the cell antigens contained on the fixed and permeabilized cells which bind the preadsorbed subsample antibodies are measured by incubating said antigens that are bound to antibodies with labeled anti-human antibodies to form labeled antigens-antibodies complexes.

9. The method according to claim 8, wherein said labeled anti-human antibodies are labeled with a compound whose fluorescence emission spectrum is distinguishable from the fluorescence emission spectrum of any other fluorophores utilized in the assay.

10. The method according to claim 8, wherein the label of said labeled anti-human antibodies comprises an antibody-linked fluorescent molecule or fluorophore.

11. A serological assay kit for determining whether a subject is infected with one, both, or neither of herpes simplex virus type-1 (HSV-1) and herpes simplex virus type-2 (HSV-2) by the method of claim 1, comprising:
a) three separate vessels that respectively comprise one of;
   (i) cell antigens from uninfected cells immobilized on a physical matrix,
   (ii) cell antigens from HSV-1-infected cells immobilized on a physical matrix, and
   (iii) cell antigens from HSV-2-infected cells immobilized on a physical matrix; and
b) a fourth vessel comprising a mixture comprising three fixed and permeabilized cell populations including: cells uninfected by either HSV-1 or HSV-2, cells infected by HSV-1, and cells infected by HSV-2, wherein the fixed and permeabilized cell populations are distinguishable from each other by fluorescence emission when irradiated.

12. The serological assay kit according to claim 11, further including a fifth vessel comprising labeled anti-human antibodies.

13. The serological assay kit according to claim 12, wherein the label of said labeled anti-human antibodies comprises a compound that when irradiated provides a fluorescence emission spectrum distinguishable from that of any other fluorophores utilized in the assay.

14. The serological assay kit according to claim 11, wherein the cell antigens immobilized on the physical matrix of a)(i), (ii), and (iii) comprise fixed and permeabilized uninfected cells, fixed and permeabilized HSV-1 cells, and fixed and permeabilized HSV-2 cells, respectively.

15. The serological assay kit according to claim 11, wherein the fixed and permeabilized cells of said fourth vessel further include an exogenously-introduced fluorescent colorant by which the three fixed and permeabilized cell populations are distinguishable from each other according to the intensity of fluorescence in a defined emission spectrum, which is distinguishable from the fluorescence emission spectrum of other fluorophores in the assay.

16. A serological assay method for determining whether a subject is infected with one, both or neither of herpes simplex-1 (HSV-1) and herpes simplex-2 (HSV-2) viruses, comprising:
a) individually admixing at least three serum subsamples obtained from a serum sample of the subject, wherein the serum sample comprises antibodies from the subject, with one of:
   (i) cell lysates from cells uninfected with HSV-1 and HSV-2 immobilized on a physical matrix,
   (ii) cell lysates from HSV-1-infected cells immobilized on a physical matrix, and
   (iii) cell lysates from HSV-2-infected cells immobilized on a physical matrix,
to form at least three serum subsample-cell lysate admixtures,
b) maintaining each of said admixtures for a time period sufficient for the antibodies to bind to said cell lysates to form admixtures comprising matrix-bound antibodies and at least three preadsorbed serum subsamples comprising antibodies;
c) removing the matrix-bound antibodies from the at least three preadsorbed serum subsamples comprising antibodies;
d) separately admixing each of said separated preadsorbed serum subsamples comprising antibodies with a mixture comprising cell lysates immobilized on a physical matrix, including:
   (i) cell lysates from cells uninfected by either HSV-1 or HSV-2 immobilized on a physical matrix,
   (ii) cell lysates from cells infected by HSV-1 immobilized on a physical matrix, and (iii) cell lysates from cells infected by HSV-2 immobilized on a physical matrix, and maintaining each of said admixtures for a time period sufficient for the antibodies to bind to the cell lysates immobilized on the physical matrices, wherein the cell lysates on the physical matrices are distinguishable from each other by fluorescence emissions when irradiated; and e) measuring the amount of binding of the antibodies present within each preadsorbed subsample to the cell lysates on the physical matrices to determine whether the subject from whom the serum sample was obtained was infected by one, both or neither of HSV-1 and HSV-2.

17. A serological assay kit for determining whether a subject is infected with one, both or neither of herpes simplex virus type-1 (HSV-1) and herpes simplex virus type-2 (HSV-2) by the method of claim 16, comprising:

a) three separate vessels that respectively comprise:
(i) cell lysates comprising antigens from cells uninfected with HSV-1 and HSV-2 immobilized on a physical matrix,
(ii) cell lysates comprising antigens from HSV-1-infected cells immobilized on a physical matrix, and
(iii) cell lysates comprising antigens from HSV-2-infected cells immobilized on a physical matrix; and b) a fourth vessel comprising:
(i) cell lysates comprising antigens from cells uninfected by either HSV-1 or HSV-2 immobilized on a physical matrix,
(ii) cell lysates comprising antigens from cells infected by HSV-1 immobilized on a physical matrix, and
(iii) cell lysates comprising antigens from cells infected by HSV-2 immobilized on a physical matrix.

18. The method according to claim 1, wherein the cell antigens immobilized on the physical matrix of a)(i), (ii) and (iii) comprise fixed and permeabilized uninfected cells, fixed and permeabilized HSV-1-infected cells, and fixed and permeabilized HSV-2-infected cells, respectively, and wherein the cells are all of the same cell type.

19. The method according to claim 4, wherein the exogenously-introduced fluorescent colorant comprises carboxyfluorescein succinimidyl ester (CFSE).

20. The serological assay kit according to claim 11, wherein the cell antigens immobilized on the physical matrix of a)(i), (ii), and (iii) comprise fixed and permeabilized uninfected cells, fixed and permeabilized HSV-1 cells, and fixed and permeabilized HSV-2 cells, respectively, and wherein the fixed and permeabilized cells are of the same cell type.

* * * * *